US010045820B2

United States Patent
Youngquist et al.

(10) Patent No.: US 10,045,820 B2
(45) Date of Patent: Aug. 14, 2018

(54) INTERNET CONNECTED DERMATOLOGICAL DEVICES AND SYSTEMS

(71) Applicant: CHANNEL INVESTMENTS, LLC, Tampa, FL (US)

(72) Inventors: David Youngquist, San Jose, CA (US); Tobin C. Island, Oakland, CA (US); Harvey I-Heng Liu, Fremont, CA (US); John P. Beale, Mountain View, CA (US)

(73) Assignee: CHANNEL INVESTMENTS, LLC, Tampa, FL (US)

( * ) Notice: Subject to any disclaimer, the term of this patent is extended or adjusted under 35 U.S.C. 154(b) by 0 days.

(21) Appl. No.: 14/625,594

(22) Filed: Feb. 18, 2015

(65) Prior Publication Data

US 2015/0230863 A1    Aug. 20, 2015

Related U.S. Application Data

(60) Provisional application No. 61/941,057, filed on Feb. 18, 2014, provisional application No. 61/941,975, (Continued)

(51) Int. Cl.
*A61B 18/20* (2006.01)
*A61B 18/00* (2006.01)

(52) U.S. Cl.
CPC .... *A61B 18/203* (2013.01); *A61B 2018/0047* (2013.01); *A61B 2018/00642* (2013.01); *A61B 2018/202* (2013.01); *A61B 2018/2085* (2013.01)

(58) Field of Classification Search
CPC ............ A61B 18/203; A61B 2018/202; A61B 2018/2085; A61B 2018/00642
See application file for complete search history.

(56) References Cited

U.S. PATENT DOCUMENTS 7,250,045 B2    7/2007    Island et al. .................... 606/17
7,452,356 B2    11/2008   Grove et al. ..................... 606/9
(Continued)

FOREIGN PATENT DOCUMENTS

AU    2013201634 A1    4/2013    ............... A61B 6/00

OTHER PUBLICATIONS

International Search Report and Written Opinion, Application No. PCT/US2015/016446, 11 pages, dated May 4, 2015.
(Continued)

*Primary Examiner* — Adam J Eiseman
*Assistant Examiner* — Patrick Fernandes
(74) *Attorney, Agent, or Firm* — Slayden Grubert Beard PLLC

(57) ABSTRACT

A dermatological treatment and analysis system includes a handheld treatment device having a handheld body, a treatment radiation source that delivers a dermatological treatment to the skin, and skin sensor(s) configured to generate signals indicative of one or more skin properties. A wireless transmitter is integrated in the handheld treatment device or in a docking/charging station that receives the handheld treatment device. The wireless transmitter is configured to receive skin-related data comprising the signals from the at least one skin sensor and/or information derived from such signals, and to wirelessly transmit the received skin-related data for analysis of the skin-related data by a remote data analysis system, which may analyze the received skin-related data to generate skin analysis data, and communicate the skin analysis data as feedback to the user of the handheld treatment device, e.g., via a website or application hosted on an internet-connected device of the user.

17 Claims, 33 Drawing Sheets

Related U.S. Application Data filed on Feb. 19, 2014, provisional application No. 61/941,961, filed on Feb. 19, 2014, provisional application No. 61/951,139, filed on Mar. 11, 2014, provisional application No. 62/003,855, filed on May 28, 2014, provisional application No. 62/003,927, filed on May 28, 2014.

(56) References Cited

U.S. PATENT DOCUMENTS

| | | | |
|---|---|---|---|
| 2006/0253176 A1* | 11/2006 | Caruso | A61B 18/203 607/88 |
| 2007/0225779 A1* | 9/2007 | Hantash | A61L 27/3804 607/89 |
| 2008/0188847 A1 | 8/2008 | Gustavsson | 606/33 |
| 2008/0194928 A1* | 8/2008 | Bandic | A61B 5/411 600/306 |
| 2010/0063365 A1* | 3/2010 | Pisani | A61B 5/0002 600/301 |
| 2010/0185064 A1* | 7/2010 | Bandic | A61B 5/0059 600/306 |
| 2010/0222845 A1* | 9/2010 | Goetz | A61N 1/37252 607/59 |
| 2011/0301441 A1* | 12/2011 | Bandic | A61B 5/0059 600/306 |
| 2012/0226268 A1* | 9/2012 | Liu | A61B 18/203 606/9 |
| 2012/0239016 A1 | 9/2012 | Liu et al. | 606/9 |
| 2012/0283709 A1* | 11/2012 | Reichert | A61B 18/203 606/9 |
| 2012/0283710 A1* | 11/2012 | Liu | A61B 18/203 606/9 |
| 2012/0283711 A1* | 11/2012 | Liu | A61B 18/203 606/9 |
| 2012/0283712 A1* | 11/2012 | Youngquist | A61B 18/203 606/9 |
| 2012/0283803 A1* | 11/2012 | Liu | A61B 18/203 607/89 |
| 2012/0289948 A1 | 11/2012 | Youngquist | 606/9 |
| 2013/0030423 A1* | 1/2013 | Reichert | A61N 5/0616 606/9 |
| 2013/0096405 A1* | 4/2013 | Garfio | A61B 5/6826 600/340 |
| 2013/0103017 A1* | 4/2013 | Weckwerth | A61B 18/203 606/9 |
| 2013/0253487 A1 | 9/2013 | Liu et al. | 606/9 |
| 2013/0322711 A1 | 12/2013 | Schultz et al. | 382/128 |
| 2014/0039473 A1* | 2/2014 | Liu | A61B 18/18 606/9 |
| 2015/0057725 A1* | 2/2015 | Weckwerth | A61N 5/0616 607/90 |

OTHER PUBLICATIONS

International Standard IEC 60825.1, Safety of Laser Products—Part 1: Equipment Classification, Requirements and User's Guide, Editon 1.2, 121 pages, 2001.

* cited by examiner

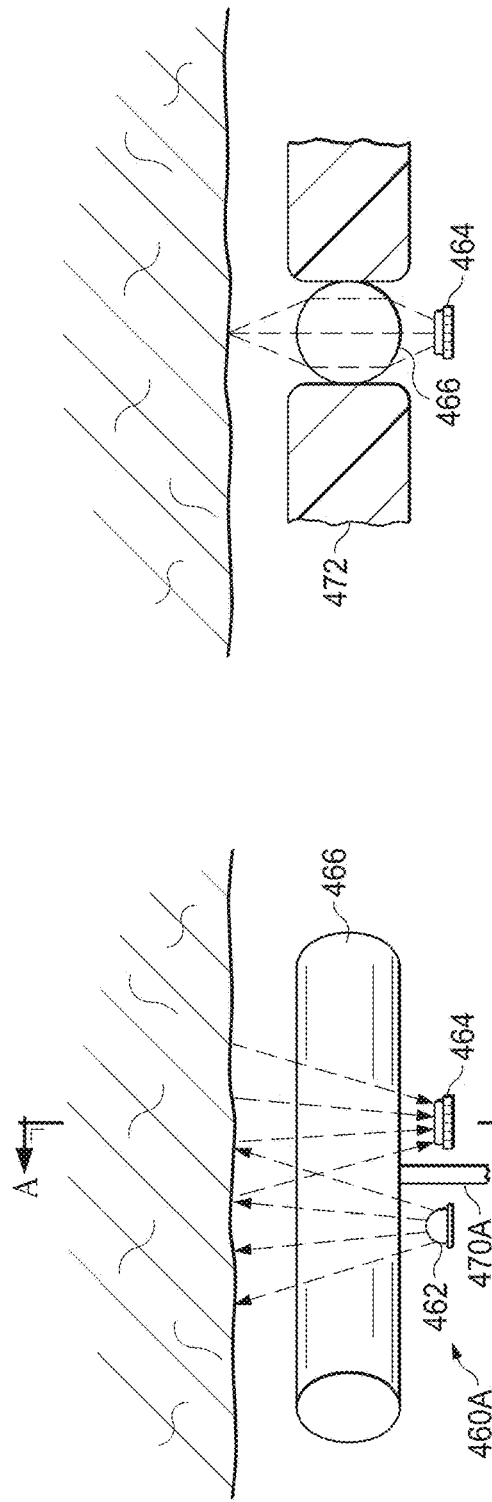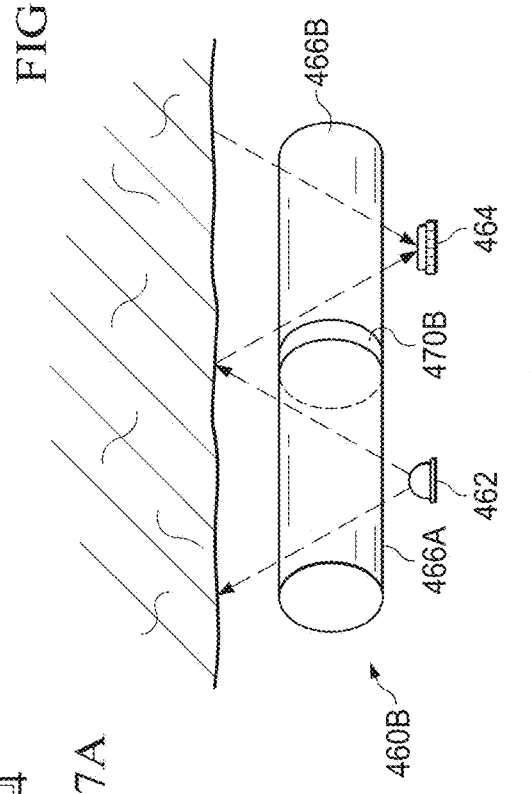

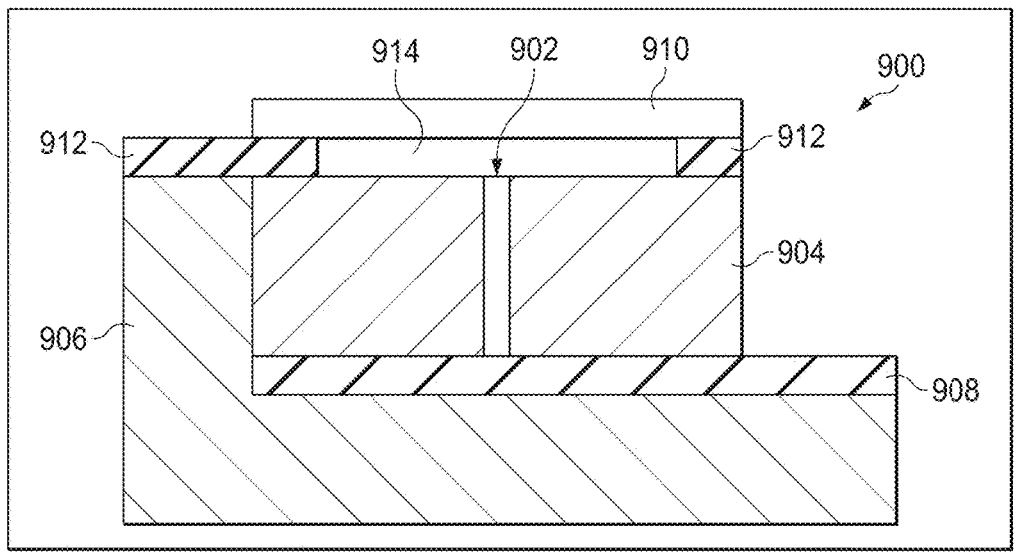
FIG. 34
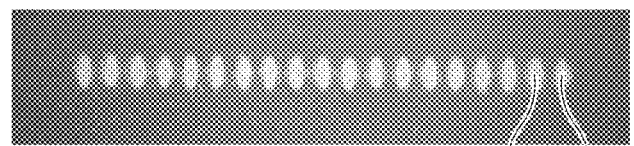
FIG. 35    70  70

INTERNET CONNECTED DERMATOLOGICAL DEVICES AND SYSTEMS

CROSS-REFERENCE TO RELATED APPLICATIONS

This application claims the benefit of U.S. Provisional Application No. 61/941,057 filed on Feb. 18, 2014; U.S. Provisional Application No. 61/941,975 filed on Feb. 19, 2014; U.S. Provisional Application No. 61/941,961 filed on Feb. 19, 2014; U.S. Provisional Application No. 61/951,139 filed on Mar. 11, 2014; U.S. Provisional Application No. 62/003,855 filed on May 28, 2014; and U.S. Provisional Application No. 62/003,927 filed on May 28, 2014, all of which applications are herein incorporated by reference in their entirety.

TECHNICAL FIELD

The present invention is related to radiation-based dermatological treatment systems and methods, in particular, to internet-connected systems for providing user feedback regarding a dermatological treatment by a radiation-based treatment device, e.g., a laser-based device for providing a fractional treatment.

BACKGROUND

Light-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering light or laser radiation to an area of tissue on a person's body, e.g., the skin or internal tissue, to treat the tissue in a photochemical, photobiological, thermal, or other manner, which can be ablative or non-ablative, among other properties, depending on the particular application. Light-based treatment devices include various types of radiation sources, such as lasers, LEDs, flashlamps, etc. For example, laser diodes are particularly suitable for certain light-based treatments and devices for providing such treatments.

One shortcoming of skin care routines practiced at home, including light-based treatments using home consumer devices, is the inability to objectively visualize or analyze the efficacy of a treatment over time, particularly where the results of the treatment are gradual over a period of weeks or even months. Light-based skin treatments using home consumer devices typically routines have slow and small incremental changes that can only be observed over a period of weeks or months. The only feedback that most people get is their daily look on their mirrors or their own tactile sensation. The relative results are difficult to assess, especially when previous reference is based on memory. Thus, users may become discouraged by the lack of objective feedback, and may thus prematurely terminate a treatment regimen.

SUMMARY

As discussed above, one common drawback of skin treatments using home consumer devices is the lack of objective feedback regarding the effectiveness of the treatment. However, electronics controlled cosmetic devices offer a new opportunity to solve this problem and provide a path to optimize the skin care routine's effectiveness.

Recent advances in chip module for wireless internet connectivity, e.g., via WiFi or Bluetooth communications, have provided an opportunity to integrate the feature of wireless internet connectivity into portable devices for data communication. When applied to an electronics controlled cosmetic device, the integrated wireless communication feature can be used to upload to web data servers device internal usage and smart sensor data for user feedback and routine optimization suggestion. The treatment usage data can be used to encourage device use compliance and correct use techniques. The smart skin sensor data can be used to track treatment/routine results and establish correlation with treatment/routine. Internet connectivity and simplified data trend visualization will enable users to optimize their routine based on their treatment and results statistics.

A further advancement that adds to the success of this vision is a set of skin quality sensors that are positively correlated with the intended treatment or skin health results. Major quality factors include skin tone, texture, wrinkles, redness, tactile roughness and hardness, and moisture, for example. Further, in some embodiments, there is no need for absolute calibration for the sensor measurement. Rather, correlation to positive results are the only requirement. This may greatly simplify the sensor design and make it possible to incorporate multiple sensor numbers and types for redundancy and individualized correlation.

Known commercial internet-connected health related devices, e.g. activity wrist band (Fitbit, FuelBand), WiFi blood pressure monitor, and WiFi scale, are mainly designed for diagnostic purposes. In contrast, the present disclosure provides an internet enabled skin care device that combines treatment with individualized results feedback and routine optimization suggestions. For a home use device intended to be used repeatedly according to a treatment regimen, each subsequent treatment offers an opportunity to evaluate the results from the previous effort. Therefore the result sensor integration and data trend tracking make provide valuable objective feedback for users.

Some embodiments provides a smart dermatological treatment device or system that can objectively determine key skin quality parameters. This is especially valuable in home use environment, where the users have little direct knowledge about the treatment mechanism and expert usage coaching can add significantly to treatment outcome. Automatic skin quality sensing feedback and the subsequent statistical trending analysis based on data collected over the treatment period may be effective for improving usage routine and correcting misuse. Some embodiments present a user with a complex set of device usage and skin quality statistical data with simple visualization in an individualized adaptive way.

Conventional home use devices typically trade off treatment source energy/power level for safety margin. This also results in slower acting efficacy and requiring more frequent and routine treatment sessions comparing to professional treatment. In order to motivate and provide useful usage and routine guidance to the user, treatment devices can be equipped with WiFi or Bluetooth module, as discussed above, to upload real-time usage and skin quality data in a relational database. Correlation and trending results can then be analyzed and presented in a simple visualization for users to take positive steps for improving the overall efficacy. The quality result trending and historical reference may provide a significant motivating factor for users to continue their routines. In addition, some embodiments make the device data collection and analysis effortless to the user and thus becomes an integral part of the regular treatment, e.g., using a handheld home-use treatment and analysis device.

In some embodiments the data analysis module is adaptive and provides feedback (e.g., scoring) that is individualized to each user. Further, the trending may be self-calibrated relative to the starting point for each user, with the final target goal established based on the historical trend for that user.

Thus, based on the above, some embodiments of the present disclosure are related to internet-connected systems for providing user feedback regarding a dermatological treatment by a radiation-based dermatological treatment device, e.g., a laser-based devices for providing a fractional treatment. The internet-connected system may include a dermatological treatment device that senses data (e.g., regarding a user's skin and/or a treatment using the dermatological treatment device) and communicates the sensed data via the internet to a remote data analysis system, which analyzes the data and provides feedback (e.g., regarding the user's skin and/or dermatological treatment) accessible to the user via the internet, e.g., such that the user can objectively monitor his or her skin and/or the effectiveness of a dermatological treatment (e.g., a fractional treatment) over time.

Some embodiments provide a dermatological treatment and analysis system, comprising a handheld treatment device including a handheld body, a treatment radiation source housed in the handheld body, electronics configured to control the treatment radiation source to deliver radiation to the skin to provide a dermatological treatment, and at least one skin sensor housed or integrated in the handheld body and configured to generate signals indicative of one or more properties of the skin; and a wireless transmitter integrated in the handheld treatment device or in a docking station or charging station configured to physically receive handheld treatment device, wherein the wireless transmitter is configured to receive skin-related data comprising the signals from the at least one skin sensor and/or information derived from such signals, and to wirelessly transmit the received skin-related data for remote analysis of the skin-related data.

In a further embodiment, the dermatological treatment and analysis system further includes a remote data analysis system configured to receive the skin-related data transmitted by the wireless transmitter via a communications network, analyze the received skin-related data to generate skin analysis data, and communicate the skin analysis data to a user via the communications network.

In a further embodiment, the remote data analysis system is configured to: identify previously received skin-related data associated with the same treatment device or user as the currently received skin-related data; analyze the currently received skin-related data and previously received skin-related data to generate skin-related trend data associated with the treatment device or user, the skin-related trend data indicating trends in one or more skin-related parameter over time; and communicate the skin-related trend data to the user via the communications network.

In a further embodiment, the remote data analysis system is configured to identify previously received device usage data associated with the same treatment device or user as the currently received device usage data; analyze the currently received device usage data and previously received device usage data to generate device usage trend data associated with the treatment device or user, the device usage trend data indicating trends in the usage of the treatment device over time; and communicate the device usage trend data to the user via the communications network.

In a further embodiment, the handheld treatment device further includes electronics configured to generate device usage data related to the usage of the handheld treatment device by a user; the wireless transmitter is further configured to wirelessly transmit the device usage data to the communications network; and the remote data analysis system configured to receive the device usage data transmitted by the wireless transmitter via the communications network; analyze the received device usage data to generate device usage analysis data; and communicate the device usage analysis data to the user via the communications network.

In a further embodiment, the dermatological treatment and analysis system further includes a user device comprising a display and configured to receive the skin analysis data transmitted by the remote data analysis system via the communications network, and display the skin analysis data to a user via the display.

In a further embodiment, the handheld treatment device, remote data analysis system, and user device are configured to cooperate such that the skin analysis data is displayable via the user device in real time or substantially in real time (a) during a treatment session using the handheld treatment device, or (b) upon the completion of a treatment session using the handheld treatment device.

In a further embodiment, the handheld treatment device, remote data analysis system, and user device are configured to cooperate such that the skin analysis data is displayable via the user device in real time or substantially in real time upon a docking of the handheld treatment device in a docking station or charging station.

In a further embodiment, the handheld treatment device, remote data analysis system, and user device are configured to cooperate such that the device usage analysis data is displayable via the user device in real time or substantially in real time (a) during a treatment session using the handheld treatment device, (b) upon the completion of a treatment session using the handheld treatment device, or (c) in an embodiment in which the wireless transmitter is provided in a docking station or charging station, upon the handheld treatment device being removably connected to the docking station or charging station.

Another embodiment provides a dermatological treatment and analysis system, comprising a handheld treatment device, a wireless transmitter, and a remote data analysis system. The handheld treatment device includes a handheld body, a treatment radiation source housed in the handheld body, electronics configured to control the treatment radiation source to deliver radiation to the skin to provide a dermatological treatment, and at least one skin sensor housed or integrated in the handheld body and configured to generate signals indicative of one or more properties of the skin. The wireless transmitter is configured to receive skin-related data comprising the signals from the at least one skin sensor and/or information derived from such signals, and to wirelessly transmit the received data to a communications network. The remote data analysis system is configured to receive the skin-related data transmitted by the wireless transmitter via the communications network, analyze the received skin-related data to generate skin analysis data, and communicate the skin analysis data to a user via the communications network.

In a further embodiment, the wireless transmitter is integrated in the handheld treatment device. In a further embodiment, the wireless transmitter is provided in a docking station or charging station to which the handheld treatment device can be temporarily and removably connected.

In a further embodiment, the dermatological treatment and analysis system further includes a user device comprising a display and configured to receive the skin analysis data transmitted by the remote data analysis system via the communications network, and display the skin analysis data to a user via the display.

In accordance with the above, some particular embodiments provide a portable internet-connected skin care device in which a WiFi or Bluetooth chip module is either embedded within the portable device or a charging cradle for the portable device. A main microcontroller of the portable device collects and processes real-time treatment usage and sensor feedback data. With each treatment, the portable device broadcasts the use data to a smart phone, tablet, or local computer through Bluetooth or to a home WiFi hotspot. These data are then transmitted to a web data server and time stamped. The collected data are aggregated and analyzed for trending feedback and skin care routine optimization, and related feedback is provided via the internet, e.g., at a website, hosted application, via emails, text messages, or in any other manner.

The portable skin-care device may include one or more radiation sources that radiate energy in the form of one or more beams to produce one or more irradiated areas on the skin that provide a dermatological treatment. As used herein, "radiation" may include any radiative energy, including electromagnetic radiation, UV, visible, and IP light, radio frequency, ultrasound, microwave, etc. A radiation source may include any suitable device for radiating one or more coherent or incoherent energy beams, e.g., a laser, LED, flashlamp, ultrasound device, RF device, microwave emitter, etc. Energy beams may be generated in any suitable manner, such as pulsed, continuous wave (CW), or otherwise (depending on the particular embodiment, application, or device setting), and then scanned by an automated scanning system to deliver a scanned array of output beams to the skin. In some embodiments, the radiation source is a laser, e.g., an edge emitting laser diode, laser diode bar, HeNe laser, YAG laser, VCSEL laser, or other types of laser, that generates one or more laser beams that are scanned and delivered to the skin to effect a treatment.

In some embodiments, the device provides automatically scanned and/or pulsed energy beams to the skin to provide a fractional dermatological treatment, e.g., skin resurfacing, skin rejuvenation, wrinkle treatment, removal or reduction of pigmentation, treatment of coarse skin caused by photodamage, etc. In embodiments that provide a fractional treatment, each delivered beam forms an irradiated treatment spot (or "treatment spot") on the surface of the skin, and a three-dimensional volume of thermally damaged (or otherwise influenced, such as photochemically) skin extending below the surface of the skin, referred to herein as a micro thermal zone (MTZ). As used herein, "fractional" treatment means treatment in which individual treatment spots generated on the skin surface are physically separated from each other by areas of non-irradiated (or less irradiated) skin (such that the MTZs corresponding to such treatment spots are generally physically separated from each other). In other words, in a fractional treatment, adjacent treatment spots (and thus their corresponding MTZs) do not touch or overlap each other.

In some embodiments, the device provides eye safe radiation, e.g., by delivering a substantially divergent energy beam (e.g., using an edge emitting laser diode with no downstream optics), and/or using an eye safety control system including one or more sensors, and/or by any other suitable manner. In some laser-based embodiments or settings, the device meets the Class 1M or better (such as Class 1) eye safety classification per the IEC 60825-1.

In some embodiments, the device may be suitable for providing a fractional treatment using a home-use treatment plan that includes treatment sessions of a few minutes or less, once or twice a day. In some embodiments, a treatment session of 4 minutes, for example, may allow an effective treatment of about 300 cm$^2$ (about 4 in$^2$), e.g., for a full-face treatment. Further, certain embodiments permits the use a small battery, and allow for thermal control without any fan(s). For example, in some embodiments, a small cylindrical block of copper can absorb the waste heat from a laser during a treatment session, preventing excessive temperature rise of the diode without the use of a fan. Other embodiments may include at least one fan for increased cooling of the device components.

BRIEF DESCRIPTION OF THE DRAWINGS

Some embodiments of the disclosure may be understood by referring, in part, to the following description and the accompanying drawings wherein:

FIGS. 17A and 17B show a side view and cross-sectional view, respectively, of a first configuration of a skin color/tone sensor including a cylindrical lens, according to an example embodiment;

FIG. 18 shows a second configuration of a skin color/tone sensor including a cylindrical lens having two sections separated by an opaque barrier, according to an example embodiment;

FIG. 34 illustrates an example laser package including a GaAs laser diode bar for use in a portable dermatological treatment device; and FIG. 35 illustrates an example pattern of treatment spots formed on the skin by a single pulse of the laser shown in FIG. 34, with the laser in close proximity to the skin, according to an example embodiment.

DETAILED DESCRIPTION OF THE DRAWINGS

Some embodiments of the disclosure may be understood by referring, in part, to the following description and the accompanying drawings, in which like reference numbers refer to the same or like parts.

Figure 1:
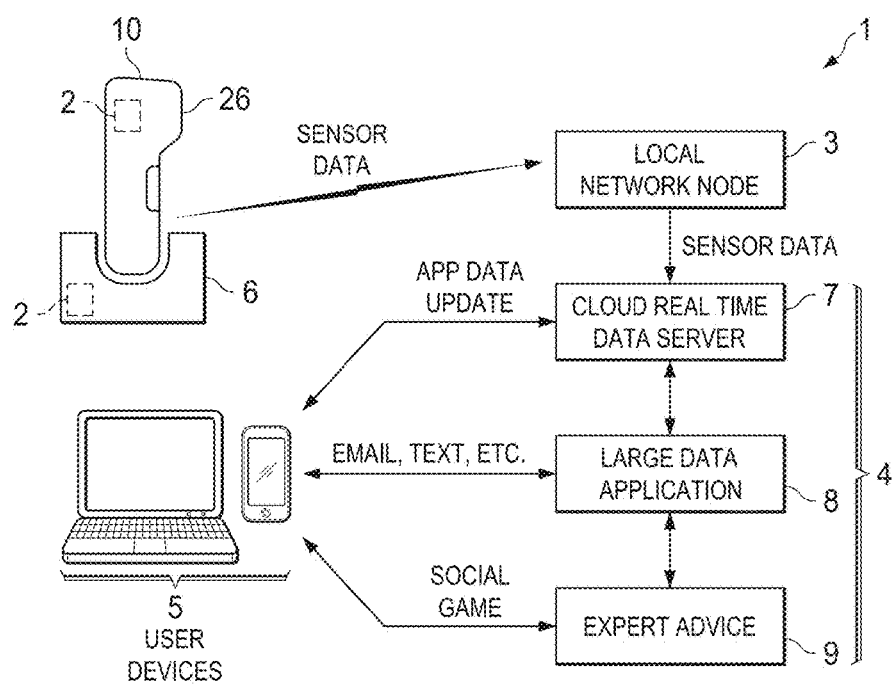
FIG. 1 illustrates an example system architecture for an internet-connected system for providing user feedback regarding a dermatological treatment provided by a portable radiation-based treatment device, e.g., a laser-based device for providing a fractional treatment, according to certain embodiments.

FIG. 1 illustrates an example system architecture for an internet-connected system 1 for providing user feedback regarding a dermatological treatment provided by a portable radiation-based treatment device 10, e.g., a laser-based device for providing a fractional treatment, according to certain embodiments. As shown, internet-connected system 10 may include portable treatment device 10, which includes an internal processor for collecting device usage data and various sensors 26 for collecting sensor data (e.g., regarding the usage of device 10 and/or characteristics of the user's skin) and an associated wireless transmitter device 2 for short-distance wireless communication of the data collected by device 10 to an internet-connected local network node 3. The internet-connected local network node 3 is configured to forward the collected data via the internet or other network to a remote data analysis system 4, which time stamps the received collected data, analyzes the collected data, and generates and communicates feedback (e.g., regarding the usage of device 10 and/or characteristics of the user's skin) via the internet or other network to any suitable user device 5, e.g., smartphone, tablet, computer, etc. In some embodiments, remote data analysis system 4 may be configured to provide feedback to the user in real-time upon receiving the collected data from device 10, e.g., upon the end of a treatment session or even in real-time during a treatment session, depending on the operational configuration of wireless transmitter device 2.

Remote data analysis system 4 may include any data servers, analysis tools, applications, and/or any other suitable components for providing feedback to device users, which components may be co-located or geographically distributed. In the illustrated embodiment, remote data analysis system 4 includes a web data server 7, a large data application 8, and an expert device module 9. Web data server 7 may be configured to update user-accessible web pages, e.g., in real-time, based on the collected data from device 10. Large data application 8 is configured to aggregate and analyze collected data from many users, e.g., for providing large-scale trending feedback and skin care routine optimization suggestions through apps, emails, and messages.

Wireless transmitter device 2 may comprise a short-distance wireless transmitting device, such as a WiFi or Bluetooth chip module, for example, configured to wirelessly transmit sensor data to the internet-connected local network node 3, which may comprise a WiFi hotspot or other internet-connected devices such as a smartphone, tablet, or smartphone, for example. Wireless transmitter device 2 may either be integrated in the portable treatment device 10, or may be provided in a docking station or charging cradle 6 for device 10. Device 10 may include a microcontroller or other processing device 144 (shown in FIG. 12) that collects and processes real-time device usage data and sensor data from sensors 26. In embodiments in which wireless transmitter device 2 is integrated in the portable treatment device 10, device 10 may transmit collected data via wireless transmitter 2 in real time, including during a treatment session, such that remote analysis system 4 may provide feedback in real-time or within seconds of device 10 collecting the data. In embodiments in which wireless transmitter device 2 is provided in a docking station or device cradle 6, device 10 may transmit collected data to wireless transmitter 2 upon being placed in the docking station/cradle 6, e.g., after each treatment session, upon which wireless transmitter 2 may then transmit the collected data (to local network node 3, which forwards the data to remote analysis system 4), such that remote analysis system 4 may provide feedback in real-time or within seconds of the user placing device 10 in the docking station/cradle 6.

Learning from many consumer survey studies regarding home-use cosmetic devices (e.g., light-based devices) indicates that correct device usage technique and treatment routine compliance continue to be a major challenge for sophisticated cosmetic devices, especially those requiring dose control and equipped with safety and use sensors. Thus, system 1 may be configured for logging usage data and providing meaningful technique or usage routine feedback to improve usage technique and compliance by device users, which in effect may be similar to having an expert personal trainer.

Some possible usage data parameters include: Total treatment session time; Effective treatment time; Session effective treatment dose; Treatment completion percent relative to IFU (Instruction for Use); Treatment use sensors trigger statistics; Safety sensors trigger statistics; Treatment level use statistics; Treatment frequency statistics; and Charging frequency statistics.

Data Visualization and Feedback

In some embodiments, system 1 provides feedback to users in the form of data visualization, e.g., via one or more user devices 5. Each internet-connected skin care device 10 in system 1 may have numerous, e.g., more than several dozens, usage and results parameters. Thus, to provide simplified, useful data visualization feedback to users, system 1 may present a simple data trend of one or more parameters that is individualized, relative, and actionable. A data trend presented to the user may define a target based on the individual user's relative trend and projected potential, rather than defining an absolute target value.

One way to achieve this goal is to collect (at remote data analysis system 4) both device usage data and skin sensor data from device 10 over time, and initially use the device usage data set as the primary trend generator to suggest and encourage more aggressive device usage and compliance, while the skin quality sensor results data statistics are developing. A results tracking algorithm may then identify from multiple types of skin quality sensor feedback one or more types that are most correlated with the usage pattern and then project a final target goal within a treatment period based on the correlation factor. This trending factor may be a single relative target composed of multiple usage and skin quality parameters that are individualized to the user. The parameter mix can also be changed at different treatment stage depending on the relative correlation strength.

Skin Quality Sensors

Each device 10 may include various sensors 26, including one or more "skin quality sensors." Device sensors 26 are discussed in more detail below with reference to FIG. 13. The function of each skin quality sensor is to provide a positive correlation to a set of specific skin quality characteristics, such as tone, texture, wrinkle, redness, thickness, firmness, and moisture, for example. Thus, in some embodiments there is no need for absolute calibration of such sensors. Device 10 may integrate multiple skin sensor types that detect data that can be correlated to device/topical routine treatment results, wherein the correlation strength can be individualized to the specific user. For a home-use device 10, the sensors are typically used in a routine repeated fashion. Unlike a scientific instrument or a medical diagnostic device, each individual measurement accuracy or repeatability is not as critical; rather, a correlation pattern is established by hundreds or thousands of data points over time. Each device 10 may include one or more of the following types of skin quality sensors.

Skin moisture sensor.

Skin tone and redness sensor.

Skin texture and wrinkle sensor.

Skin thickness, firmness, and aging sensor.

Each of these sensors is discussed in greater detail below, beginning with the discussion of skin quality sensors 218 shown in FIG. 12.

In some embodiments, device 10 is a fractional laser skin treatment anti-aging device 10 including multitude skin quality sensors, e.g., one or more of the sensor types discussed above, and having internet connectivity (e.g., according to the architecture shown in FIG. 1), such that data collected by the device sensors can be transmitted for remote processing and user feedback at a user device 5. The collected usage and result trend data may provide feedback for enhancing usage technique by the user, as well as defining achievable individualized goals for the user, which work in combination to encourage good and healthy skin care routine.

Figure 2:
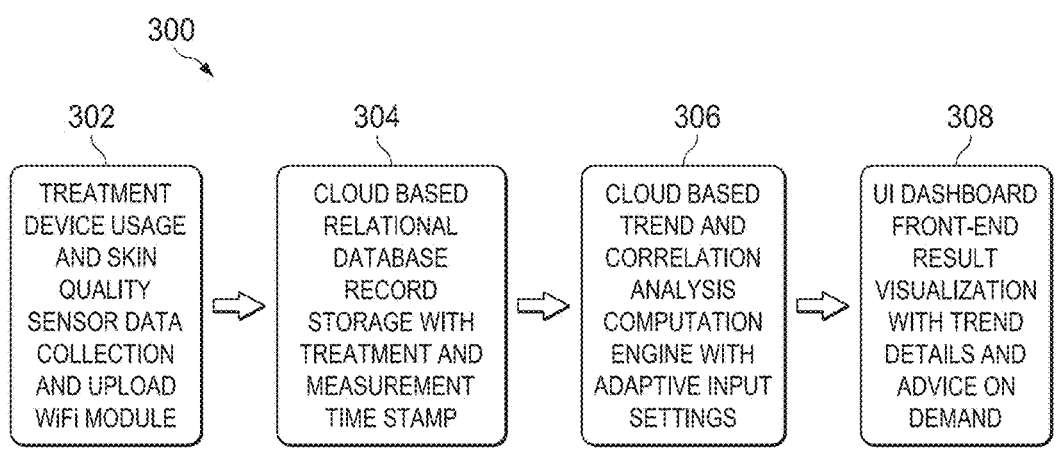
FIG. 2 illustrates an example process flow for providing real-time data collection and feedback regarding device usage and/or skin quality using the internet-connected system of FIG. 1, according to an example embodiment.

FIG. 2 illustrates an example process flow 300 for providing real-time data collection and feedback regarding device usage and/or skin quality via the internet-connected system 1, according to an example embodiment.

With reference to FIGS. 1 and 2, at step 302, treatment device usage data and skin quality data measured by the integrated skin sensors 26 of the device 10 are collected and automatically uploaded through a wireless transmission device 2 (e.g., WiFi or Bluetooth module) and corresponding local network node 3 (e.g., WiFi hotspot or internet-connected computer shpartphone, etc.) to a cloud based server 7. In some embodiment, the data collection is performed throughout the treatment session and the data uploading is performed at the end of each session. In another embodiment, the data collection and data uploading are both performed in real-time throughout the treatment session. The data collection and uploading is an automated, integral part of a normal treatment routine, such that no extra effort is required from the user to initiate the process.

As shown at 304, the collected treatment device usage and skin quality sensor data may be uploaded and organized in a cloud-based relational database 7, such as an SQL database. Uploaded data sets may be time stamped for each treatment session and/or exact time within the respective treatment session and can be cross-correlated with each other in the subsequent trend analysis. It is also possible to integrate into the same database 7 additional skin quality data such as images taken from the same treatment device 10 or other companion accessory devices, e.g., to generate on-demand before-and-after images for additional motivation to the user.

At 306, a back-end cloud based computation engine/application server may perform the core trend and treatment correlation analysis for the data stored in the relational database. The stored data may have device specific calibration parameters to compute absolute results based on the collected sensor data. These absolute result data can be used for relative comparison to other users' results in a broader database, e.g., large data server 8 shown in FIG. 1. For personal adaptive UI feedback, the trend computation engine may apply adaptive weighting factors obtained from initial personal settings to different measured score parameters, such that results are completely personalized. An example of the personal setting file is shown below. The detailed personal setting parameters can be obtained from a one-time device activation process for device 10, e.g., through a combination of interview questions and device initial data reference.

ADLTreatmentAnalyzerConfig

[ADL Treatment Analyzer Version]

program ID = 72
major version = 1
dot version = 7
version text = "72-1.007"
[ADL Treatment Analyzer Config]

config date = "2014-04-07"
config author = "Harvey I. Liu"
device model = "TRIA ADL"
device serial ID "510231076"
default username = "harveyliu"

ADLTreatmentAnalyzerConfig

[ADL Usage SQL Database Config]

database name = "TRIA Connect ADL Usage"
config table name = "thingspeak_data_miner_config"
result table name = "thingspeak_data_miner_results"
analysis short term period (weeks) = 1
analysis long term period (weeks) = 12
session treatment on time minimum (sec) = 5
[ADL Skin Quality Image Meter SQL Database Config]

database name = "TRIA Connect Skin Imaging Meter"
config table name = "skin_tone_texture_meter_config"
result table name = "skin- tone- texture- meter- results"
analysis period (weeks) = 12
[ADL Texture SQL Database Config]

database name = "TRIA Connect ADL Texture"
config table name = "thingspeak_data_miner_config"
result table name = "thingspeak_data_miner_results"
analysis short term period (weeks) = 1
analysis long term period (weeks) = 12
[ADL Usage Routine Analyze Config]

nominal treatment period (day) = 1
nominal treatment time start hour = 16
nominal treatment time end hour = 23
short period overtreatment penalty scaling factor = 125
long period undertreatment penalty scaling factor = 17
routine index treatment period weighting factor 0.8
routine index treatment time weighting factor = 0.2
improvement index derating factor = 200
routine index short term weighting factor = 0.4
routine index long term weighting factor = 0.3
routine index improvement weighting factor = 0.3
[ADL Usage Dose Analyze Config]

nominal full face complete percent = 50
incomplete penalty scaling factor = 1
level -1 max score index 20
level-2 max score index = 75
level-3 max score index = 100
dose index percent complete weighting factor 0.6
dose index level use weighting factor = 0.4
improvement index derating factor = 200
dose index short term weighting factor = 0.4
dose index long term weighting factor = 0.3
dose index improvement weighting factor = 0.3
[ADL Usage Technique Analyze Config]

nominal treatment time efficiency percent = 90
time efficiency penalty scaling factor = 2.0
improvement index derating factor = 200
technique index short term weighting factor= 0.7
technique index long term weighting factor = 0.1
technique index improvement weighting factor = 0.2
[Skin Texture Analyze Config]

nominal texture smoothness index = 80
texture smoothness index penalty scaling factor 1.3
nominal monthly improvement points = 5
improvement index derating factor = 10
texture index smoothness weighting factor = 0.2
texture index improvement weighting factor = 0.8
[Skin Tone Analyze Config]

nominal tone uniformity index = 100
tone uniformity index penalty scaling factor = 1.0
nominal non-redness index = 100
non-redness index penalty scaling factor = 1.0
nominal radiance index = 100
radiance index penalty scaling factor = 1.0
nominal tone uniformity monthly improvement points = 10
tone uniformity improvement index derating factor = 5
nominal redness monthly improvement points = 10
redness improvement index derating factor = 5
nominal radiance monthly improvement points = 10
radiance improvement index derating factor = 5

| ADLTreatmentAnalyzerConfig |
| --- |
| nominal index weighting factor = 0.2 |
| improvement weighting factor = 0.8 |
| tone index uniformity weighting factor = 0.6 |
| tone index redness weighting factor = 0.2 |
| tone index radiance weighting factor = 0.2 |
| [Skin Collagen Analyze Config] |
| nominal mean skin mends density = 100 |
| mean mends density penalty scaling factor 1.0 |
| nominal range skin mends density = 200 |
| mean mends density penalty scaling factor 0.5 |
| mean mends density weighting factor = 0.5 |
| range mends density weighting factor = 0.5 |

At step 308, the final results may be displayed to the user at a user device 5 via a dashboard UI that can convey device usage effort and skin quality results progress. In one embodiment, the status and progress visualization are provided through a set of intuitive color association with different state (e.g., red, yellow, green), graphical icons, or other suitable indicators. The dashboard can also be personalized with key independent parameter set that the user would like to focus on. Detailed statistical results, trending chart, before-and-after images, and expert recommended usage and routine advice can also be supplied in real-time or on demand as the user explore further down the dashboard interface. With the cloud database and analytics engine, all these results can be accessed through a web browser or application at a user device 5 (phone, tablet, laptop, etc.) anytime and anywhere.

UI Dashboard

Figure 3:
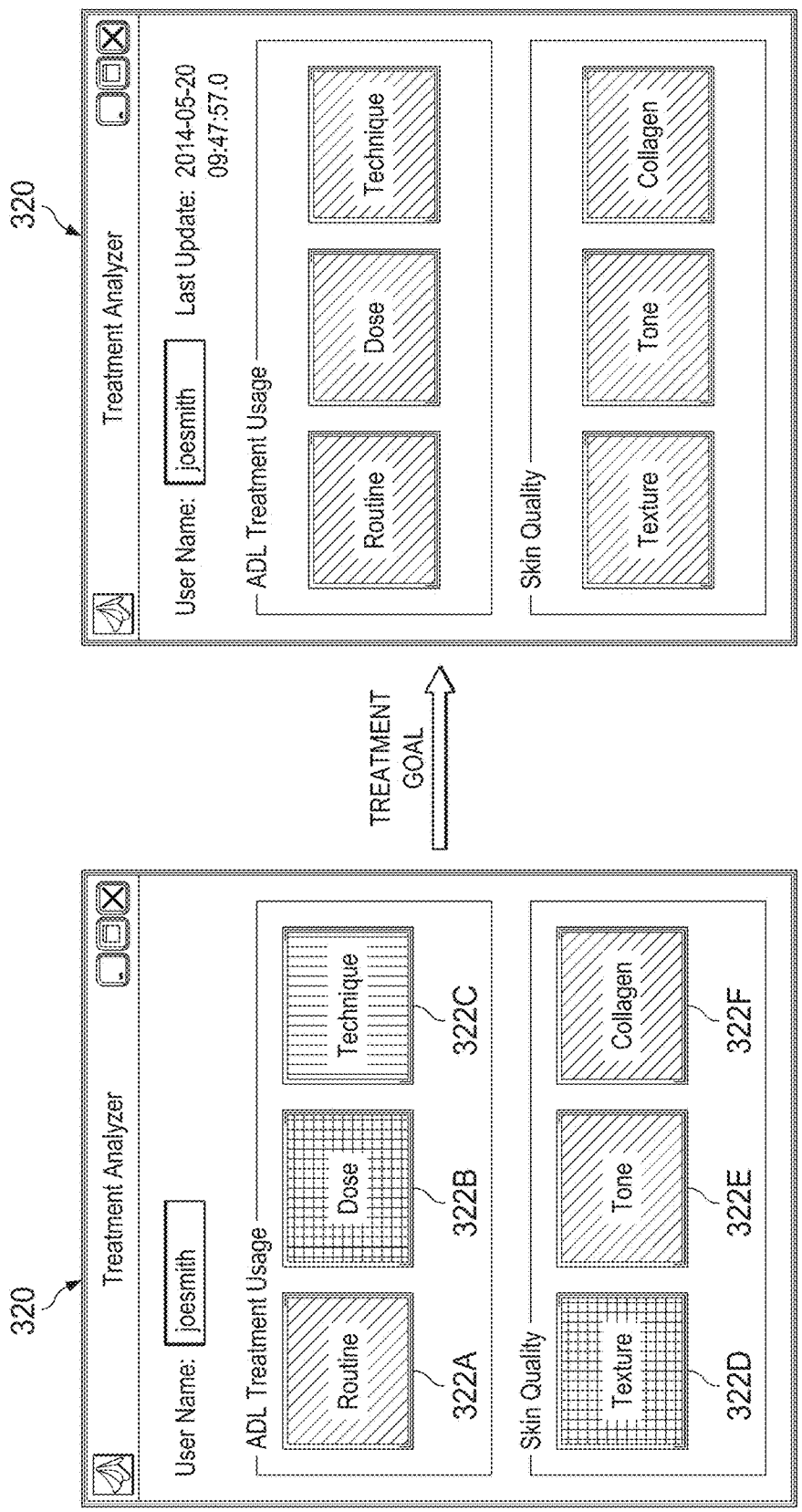
FIG. 3 illustrates an example user interface dashboard for providing user feedback regarding device usage and/or skin quality using the internet-connected system of FIG. 1, and illustrates an example current status of the feedback and a corresponding treatment goal, according to an example embodiment.

FIG. 3 illustrates an example user interface (UI) dashboard 320 for providing user feedback regarding device usage and/or skin quality using the internet-connected system of FIG. 1, according to an example embodiment. As shown, the UI dashboard 320 may be organized to convey a quick sense of device use and skin quality results. It may also be used as a motivational game for a user to achieve a personal treatment target. The example dashboard 320 includes user-selectable panels 322A-322C for three sets of device usage parameter categories and user-selectable panels 322D-322F for three sets of skin quality results parameter categories, such that each panel represents a key usage or skin quality results category. Clicking or touching each category panel 322A-322F will reveal additional details and/or advice regarding that category. The key usage categories in this example are routine, dose, and technique, corresponding to user-selectable panels 322A-322C. The key skin quality results categories in this example are texture, tone, and collagen, corresponding to user-selectable panels 322D-322F. Discrete colors are used to convey the progress of each category. In this case, red, yellow, and green are used, with red being most undesirable and green being most ideal. The treatment goal is to make all category panels turn green. Thus, the left side of FIG. 3 shows a state of dashboard 320 in which the different categories are at different levels of progression/desirability, indicated by different corresponding panel colors, while the right side of FIG. 3 shows a state of dashboard 320 in which all categories are at the top level of progression/desirability, indicated by the corresponding panel color (e.g., green).

Device Usage Screens

Figure 4A:
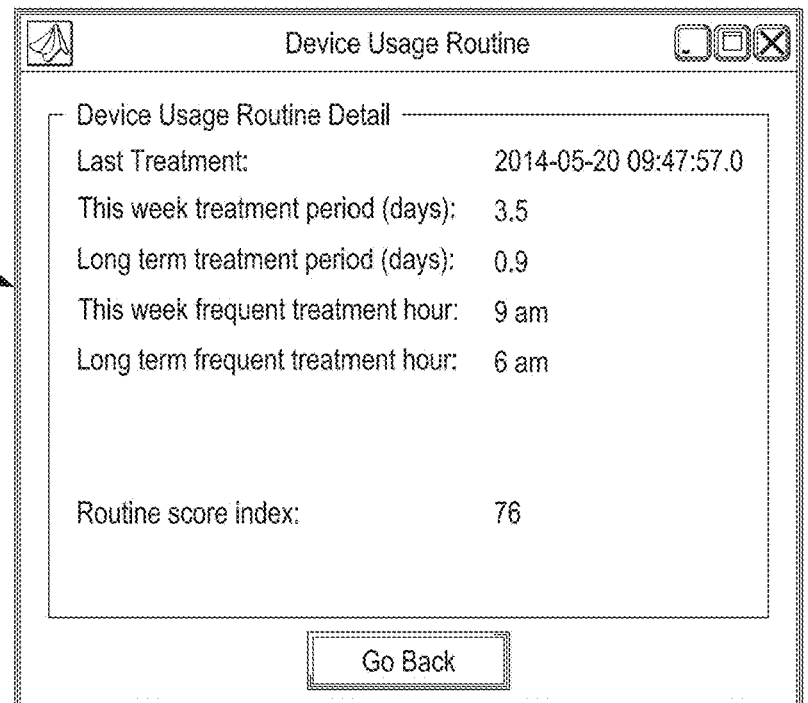
FIGS. 4A-4F illustrate six example feedback screens corresponding to the six example panels of the user interface dashboard of FIG. 10, the six feedback screens indicating data regarding the device usage routine (FIG. 4A), data regarding the device usage dose (FIG. 4B), data regarding the device usage technique (FIG. 4C), data regarding the user's skin texture (FIG. 4D), data regarding the user's skin tone (FIG. 4D), and data regarding the user's skin collagen (FIG. 4F), according to an example embodiment.
Figure 4B:
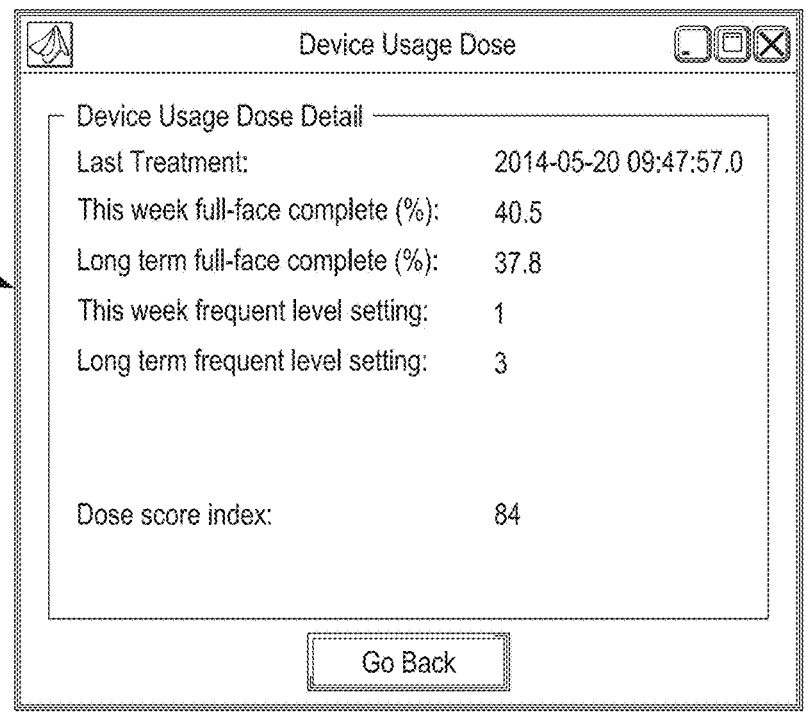
Figure 4C:
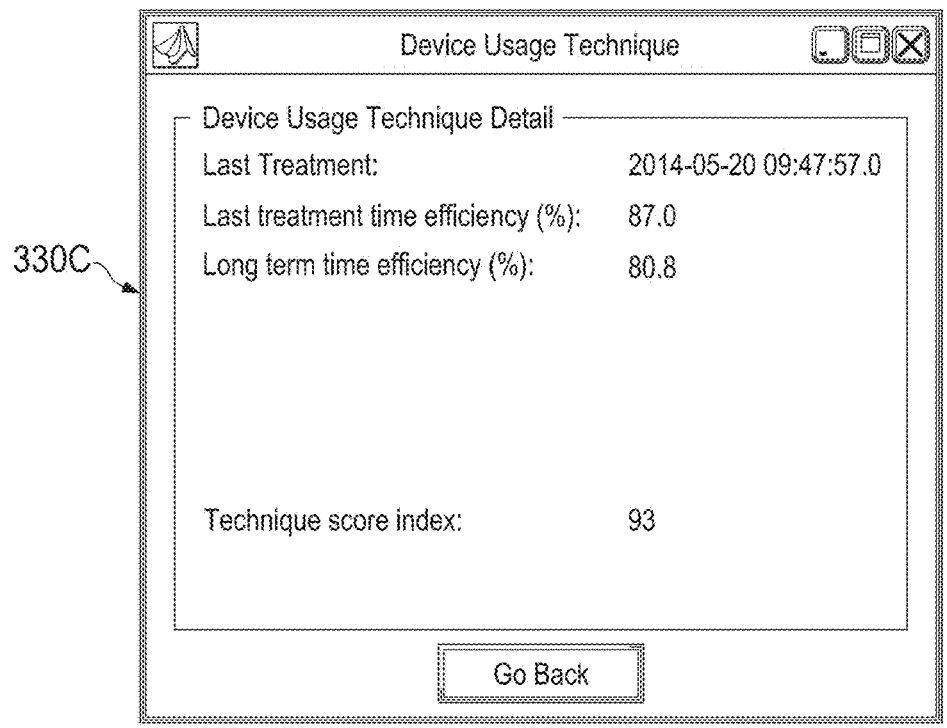
Figure 4D:
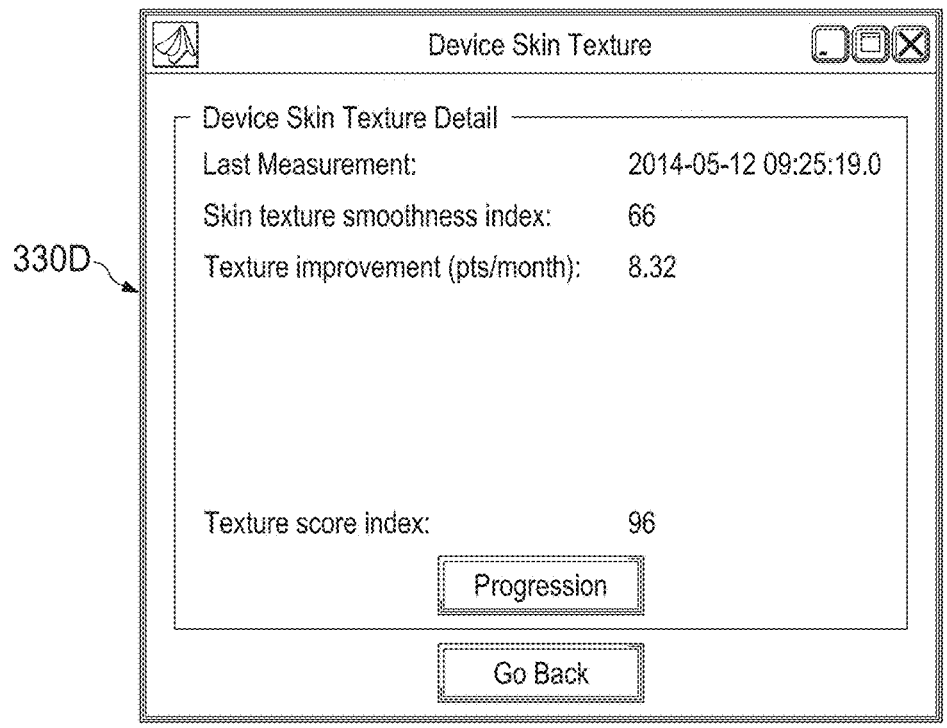
Figure 4E:
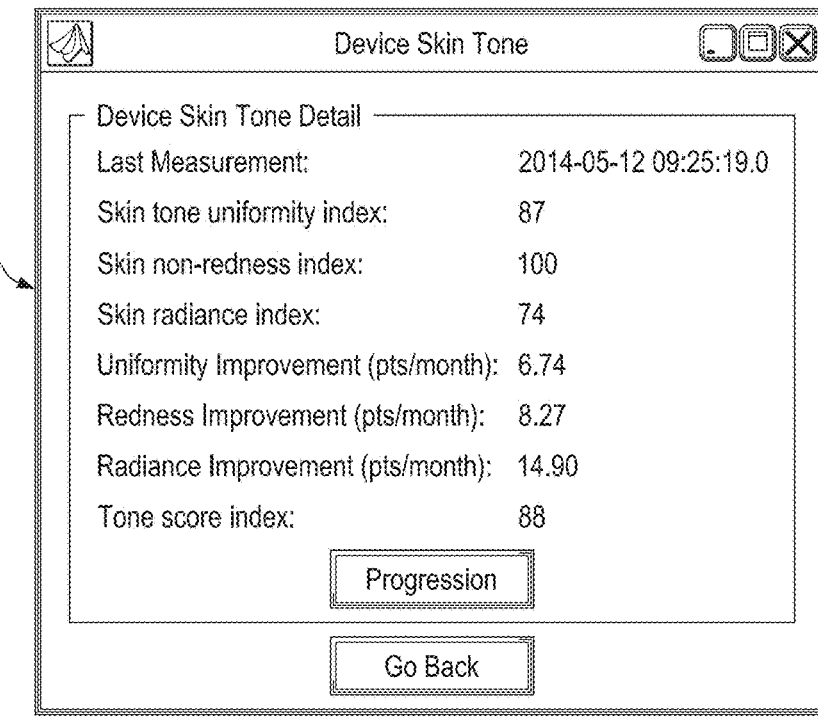
Figure 4F:
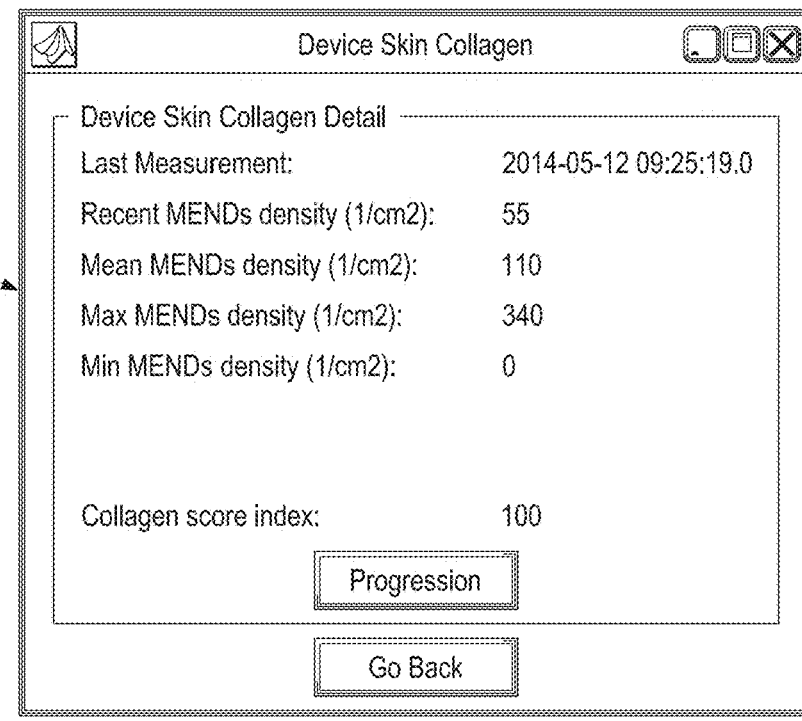

FIGS. 4A-4F illustrate example feedback screens 330A-330F that are displayed upon user selection of the corresponding dashboard panel 322A-322F, which feedback screens 330A-330F include additional details and/or advice regarding the respective device usage or skin quality category, according to an example embodiment. FIG. 4A-4C illustrate feedback screens 330A-330C regarding device usage routine, device usage dose, and device usage technique, respectively.

The usage routine screen 330A contains information such as usage period, both long term and short term, and also most frequent usage time. The dose screen 330B includes statistics on treatment power level setting, completion relative to target setting, and actual dose delivered to the user. The usage technique screen 330C contains information such as treatment efficiency obtained from the device usage sensor data. All these can be used to generate specific advice that can also be displayed on the detailed UI or delivered to the user via other channels, such as emails or other messaging services, for example.

Skin Quality Screens

FIG. 4A-4C illustrate feedback screens 330D-330F regarding the user's skin quality, in particular skin texture, skin tone, and skin collagen, respectively. The skin texture screen 330D shows a measure of a spatial roughness profile, e.g., on the scale of sub-mm size. This is often cited as the most obvious early skin quality result feedback for a non-ablative fractional laser treatment. The skin texture screen 330D may also display a separate wrinkle category based on larger scale spatial variation detected in the skin. These spatial variation profiles can be measured optically through an imaging system or a non-imaging near-field optical probe provided in device 10. Blue light source is most well suited for this purpose and can provide skin spatial resolution better than 0.2 mm.

The skin tone screen 330E indicates parameters related to skin pigmentation, e.g., including uniformity, colors, and brightness (or radiance). These can be detected, for example, by an imaging or non-imaging optical probe in device 10. One effective approach is to use a white LED light source and measure various relative spectral intensities, e.g., the ratio of green to red.

Finally the skin collagen screen 330F indicates a measure of underlying skin health. In one embodiment, measured collagen data can be derived from an optical fluorescence probe (e.g. 335-390 nm near-UV or 400-430 nm deep-blue LED source) provided in device 10. The fluorescence signals can be correlated with dermal tissue crosslinks and epidermal wound healing. It is also possible to correlate collagen health with skin moisture using a capacitive probe in device 10. A general electrical AC impedance spectroscopy can also be used for the dermal tissue correlation. As another example, an intermediate treatment marker of MENDs (Micro Epidermal Necrotic Debris) density is used to correlate with the expected subsequent collagen regrowth.

Skin Quality Trending Charts UI

In addition to the skin quality data presented via screens FIG. 4A-4C, system 4 may analyze and provide user feedback regarding historical data trends for various parameters over time.

Figure 5A:
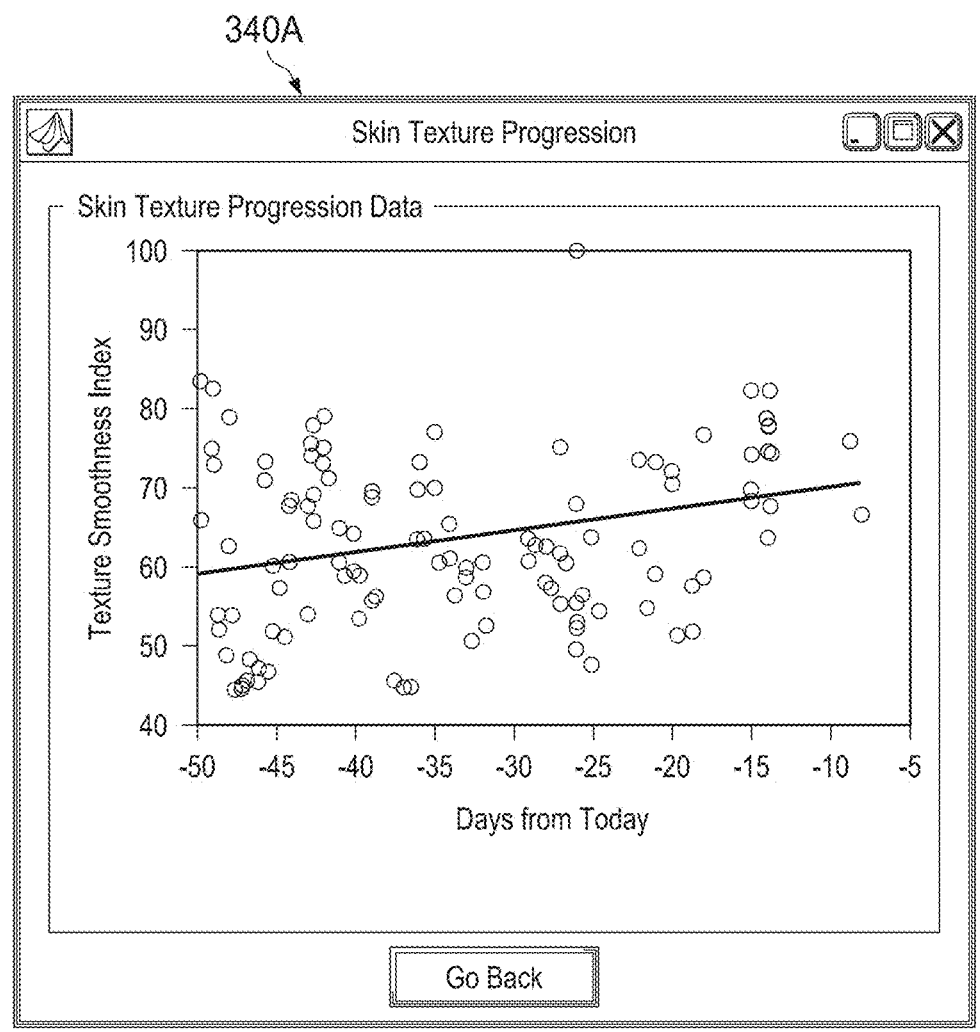
FIGS. 5A-5C illustrate three example feedback screens indicating data trends corresponding to the user's skin quality, in particular showing a measured trend of the user's skin texture (FIG. 5A); a measured trend of the user's skin tone (FIG. 5B); and a measured trend of the user's skin collagen (FIG. 5C), according to an example embodiment.
Figure 5B:
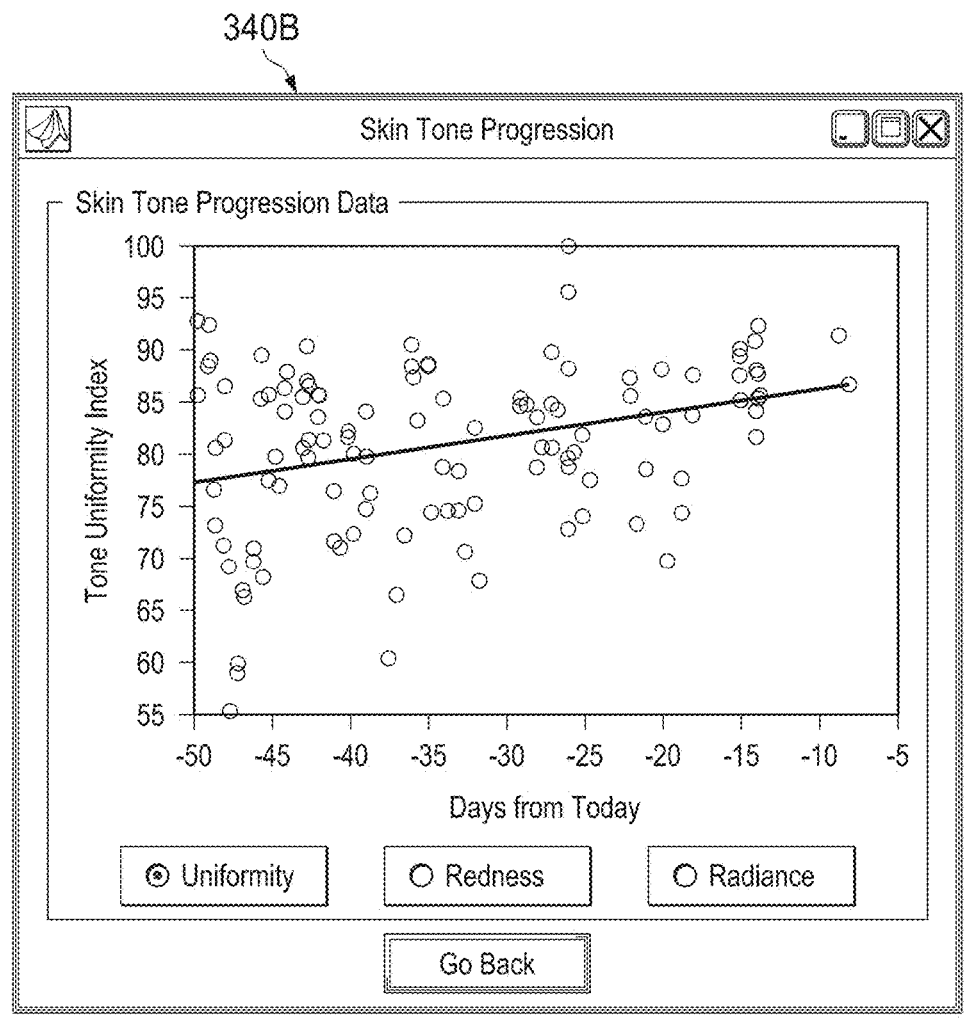
Figure 5C:
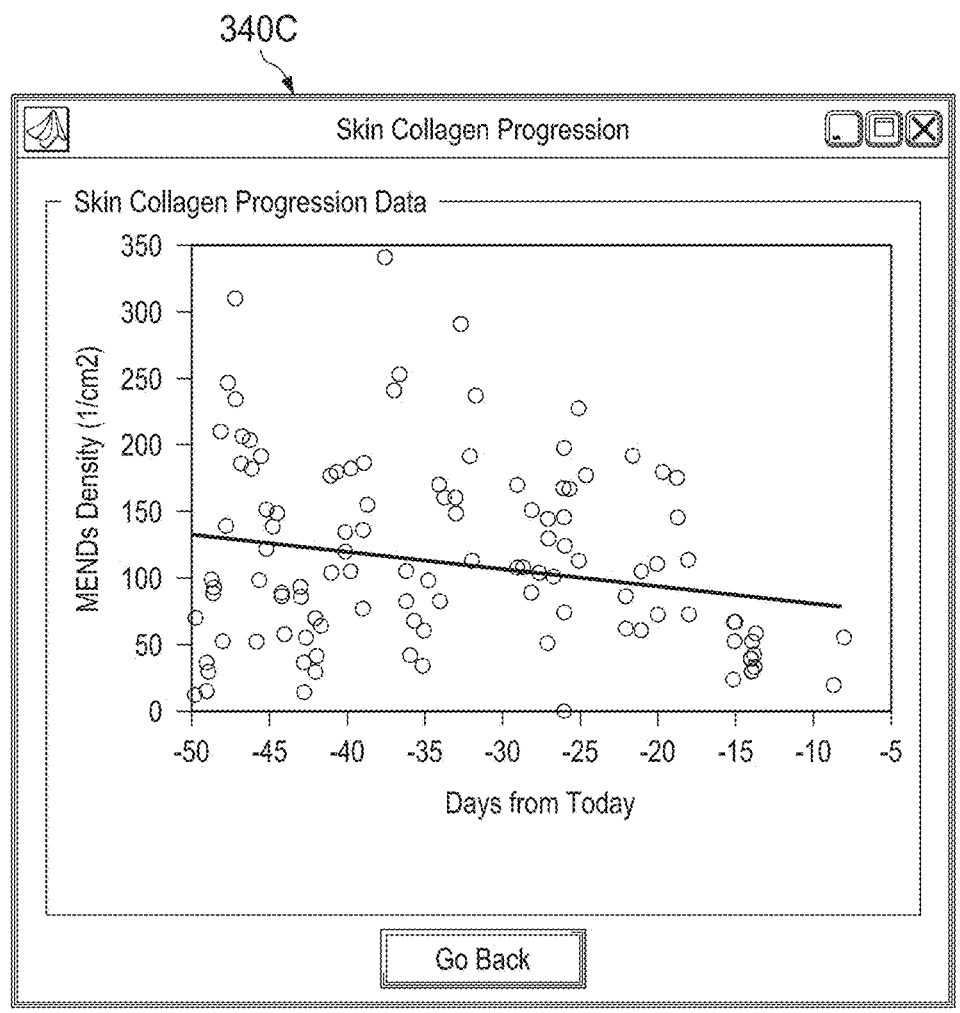

FIGS. 5A-5C illustrate example feedback screens, accessible via dashboard 320, indicating data trends corresponding to the user's skin quality, to an example embodiment. In particular, the screens include a skin texture trend screen 340A, a skin tone trend screen 340B, and a skin collagen trend screen 340C. As shown, the analyzed sensor data may be relatively noisy. This is to be expected for a realistic treatment feedback, as the results of individual treatments may be embedded in the background of larger variations caused by other normal day-to-day environmental and biological factors. Thus, analysis of the data trends over time allow the user to observe the underlying improvement statistically in a large dataset and over a long period.

Based on the above, the disclosed internet-connected, cloud-based adaptive device usage and skin quality data feedback system provides a simple intuitive user interface, e.g., to coach and motivate users to optimize their individual treatment efficacies. Besides device usage and routine coaching, the system also provides a way for the users to monitor their skin quality and health as an integral part of a treatment regimen using device 10.

Any of the concepts disclosed herein may be incorporated in or combined with any suitable dermatological treatment device 10 for providing any type of dermatological treatments, e.g., a fractional laser treatment device 10 for any suitable dermatological treatment, e.g., skin rejuvenation, wrinkle treatment, treatment of vascular lesions (e.g., spider veins, diffuse redness, etc.), treatment of cellulite, treatment of pigmented legions (e.g., age spots, sun spots, moles, etc.), tattoo removal, or other fractional treatments; a hair removal device 10 for providing hair removal treatments; an acne treatment device 10 for providing acne treatments; or any other type of radiation-based dermatological treatment device.

Some example feature and advantages of embodiments of the invention are as follows. First, the skin quality measurement is an integral part of the device treatment. The entire data collection and upload can be integrated into a self-contained hand-held treatment device. Further, multiple device usage and skin quality parameters may be captured within the same treatment session. Further, treatment usage/routine and skin quality data with device specific calibration parameters are organized in a cloud based relational database. Further, personal individualized settings may be used to adaptively adjust various score weighting factors so that the results can be presented relative to the user's starting point. Thus, the target goal setting may also be relative and personalized. Further, simple sets of independent categories with intuitive color-coded visualization may be provided via a front-end UI dashboard. This makes treatment and routine optimization easy without additional details. Further, the analyzed results of the automated large dataset over extended period enables a user to objectively discern the improvement result and establish treatment correlation. The imaging data can also be used to generate on-demand before-and-after skin comparison. Further, existing safety and treatment sensor hardware can be dual used for skin quality sensors configured to collect sensor during treatments, such as using the capacitive skin contact sensor for moisture measurement, using the skin tone/color optical sensor for tone uniformity and/or redness measurement, and using a near-field optical displacement sensor for texture and wrinkle measurement.

FIGS. 7-13 illustrate example radiation-based fractional treatment devices 10 that may be used in the internet-connected system 1 shown in FIG. 1, according to some example embodiments. Such radiation-based fractional treatment devices may include, along with any additional sensor(s) and wireless transmission capabilities disclosed herein, any of the features disclosed in U.S. patent application Ser. Nos. 13/366,202 or 13/443,717, which are hereby incorporated by reference in their entirety. However, as discussed above, in other embodiments device 10 used in the internet-connected system 1 may be any other type of dermatological treatment device for providing any type of dermatological treatments, such as a hair removal device or an acne treatment device, for example. For example, device 10 may be a hair removal device including, along with any additional sensor(s) and wireless transmission capabilities disclosed herein, any of the features disclosed in U.S. Pat. Nos. 7,250,045 or 7,452,356, which are hereby incorporated by reference in their entirety.

Figure 7:
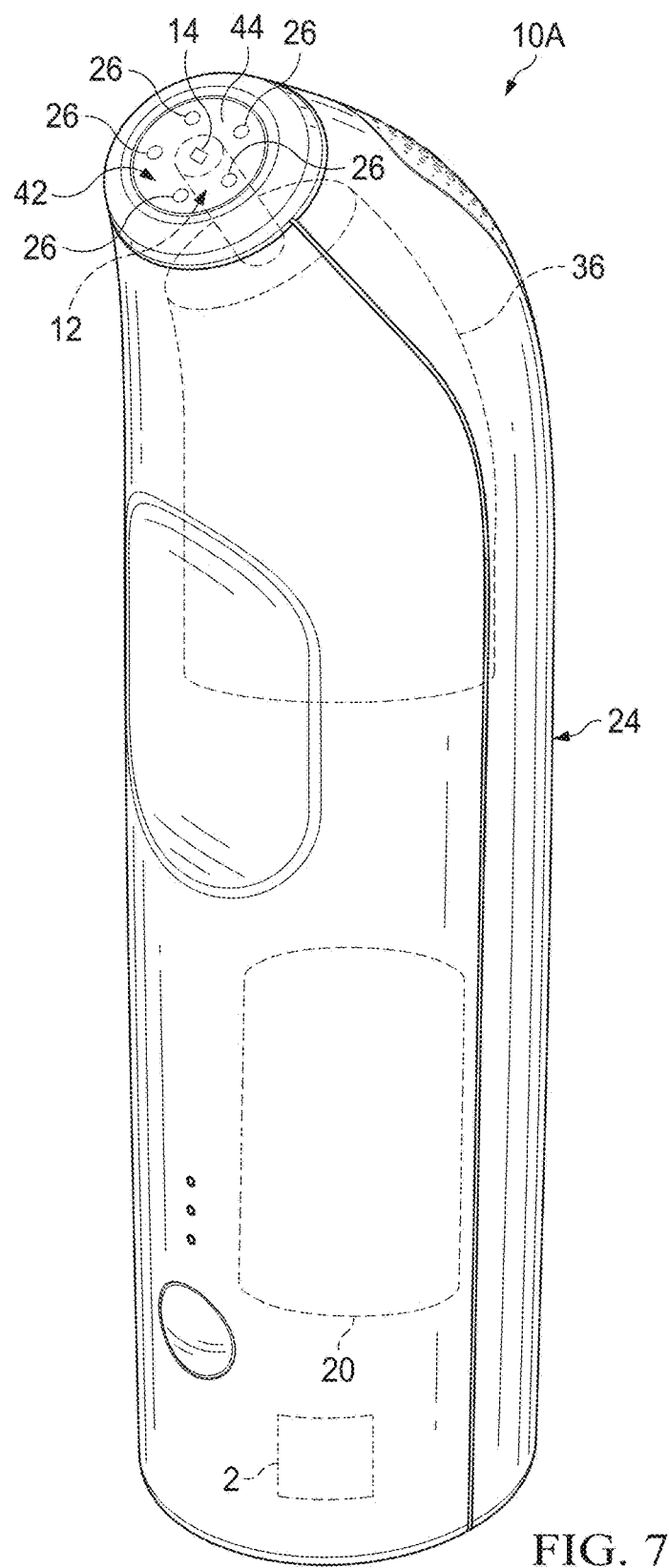
FIG. 7 shows one example configuration of the example portable radiation-based treatment device of FIG. 7, according to an example embodiment.

FIG. 7 illustrates various components of an example radiation-based fractional treatment device 10A for use in the internet-connected system 1 shown in FIG. 1, according to certain embodiments. Fractional treatment device 10A may include a radiation engine 12 including a radiation source 14 (e.g., one or more laser devices) configured to generate an energy beam 60, optics 16 for conditioning and/or delivering the energy beam 60 to a treatment area of skin 40, control systems 18, one or more power supplies 20, one or more sensors 26, and a wireless transmitter device 2.

Some embodiments of device 10A may omit optics 16 such that no significant optics are provided between radiation source 14 and the skin surface, thus providing direct radiation of the skin. Further, as discussed above, in some direct exposure embodiments, the emitting surface of radiation source 14 is located in close proximity (e.g., within 10 mm, 5 mm, 2 mm, or 1 mm) of the skin-contacting surface of the treatment tip of the device or target tissue 40.

In some embodiments, the main components of device 10A may be substantially self-contained in a held-held structure or outer housing 24. Held-held housing 24 may define an application end (or "treatment tip") 42 configured to be placed in contact with the skin (or other target surface) during treatment of a treatment area of skin 40. Application end 42 may include or house various user interfaces, including the treatment delivery interface for delivering energy beam 60 to the user, as well as one or more sensors 26 for detecting various characteristics of the skin (or other surface) and/or energy delivered by device 10A. As discussed herein, sensors 26 may include one or more dedicated skin quality sensors for detecting signals indicative of one or more skin characteristics (e.g., skin moisture, texture, tone, collagen, etc.) and/or one or more dual-use sensors configured to detect signals indicative of one or more skin characteristics as well as providing other functionality. Application end 42 may include an aperture or window 44 through which the laser beam is delivered to the target surface, or alternatively, an optical element 16 (e.g., a lens) may be located at application end 42 and configured for direct contact or close proximity with the skin during treatment. Device 10A may include any other components suitable for providing any of the functionality discussed herein or other related functionality known to one of ordinary skill in the art.

Radiation engine 12 may include one or more radiation sources 14, such as one or more lasers, LEDs, and/or flashlamps, ultrasound devices, RF devices, or microwave emitters, for example. Embodiments including lasers as the radiation source 14 may include any type or types of lasers, e.g., one or more edge emitting laser diodes (single emitter edge emitting laser diodes or multiple emitter edge emitting laser diodes), laser diode bars, VCSEL lasers (Vertical Cavity Surface Emitting Lasers), CO2 lasers, Erbium YAG lasers, pulsed dye lasers, fiber lasers, other types of lasers, or any combination thereof.

Radiation source 14 may include one or more beam source, each operable to generating a beam for delivery to the skin. In some embodiments, radiation source 14 is a laser having exactly one beam source for generating a single beam, for example (a) a single-emitter edge emitting laser diode that generates a single beam, (b) a multi-emitter edge emitting laser diode that generates a single collective beam, e.g., as described in U.S. patent application Ser. No. 13/425,995, the entire contents of which are hereby incorporated by reference, (c) a laser diode bar with high fill factor to generate a single collective beam or single beam with spatial modulation of its energy profile, e.g., as described in U.S. patent application Ser. No. 13/426,203, the entire contents of which are hereby incorporated by reference, or (d) a VCSEL laser having multiple emitters that together act as a single beam source (i.e., a single "micro-emitter zone") to generate a single combined beam, e.g., as described in U.S. patent application Ser. Nos. 13/366,202 or 13/848,460, the entire contents of which are hereby incorporated by reference. Item (b) "a multi-emitter edge emitting laser diode that generates a single collective beam" refers to an integral or monolithic laser diode structure having multiple emitter junctions formed on a substrate (such as, for example, a "multiple quantum well" (MQW) laser diode), and is thus distinguished from a laser diode bar.

In other embodiments, radiation source 14 is a laser having multiple beam sources for generating multiple discrete beams, for example (a) an laser diode bar having multiple emitters, each generating a single discrete beam, or (b) a VCSEL laser having multiple micro-emitter zones (with one or more emitter per zone), with each micro-emitter zone acting as a discrete beam source to generate a single beam discrete from the others, e.g., as described in U.S. patent application Ser. Nos. 13/366,202 or 13/848,460. Such multiple beam sources may be arranged in a row, a two-dimensional array, or otherwise.

Radiation source 14 may be configured for or operated at any suitable wavelength and energy or power level to provide the desired dermatological treatment. Further, radiation source 14 may deliver continuous wave (CW) radiation, pulsed radiation, or in any other manner, depending on the particular embodiment, application, or device setting.

As used herein, a "treatment spot" means a contiguous area of skin irradiated by a beam source—during a continuous period of irradiation or during a pulse (as defined above)—to a degree generally sufficient to provide a desired treatment in the skin at that location. For some types of beam source, including laser beam sources for example, the boundaries of the treatment spot are defined by the "$1/e^2$ width," i.e., the treatment spot includes a contiguous area of the skin surface that is irradiated by a radiation intensity equal to at least $1/e^2$ (or 0.135) times the maximum radiation intensity at any point on the skin surface. A treatment spot may include the full extent of the surface (or volume) irradiated. A treatment spot may include the full extent of the tissue being influenced by the irradiation, which may be smaller than the irradiated area or volume, or may be larger (e.g., due to thermal conductivity). Further, reference to a treatment spot "on the skin" or similar language refers to radiation pattern on the skin which generally produces a radiation pattern within the skin, whether or not it produces a treatment effect on the surface of the skin.

Certain embodiments of device 10A include one or more optics 16 downstream of radiation source 14 for directing or treating the beam 60 emitted from radiation source 14 before reaching the target surface. Optics 16 may allow for radiation source 14 to be positioned at any desired distance from the application end 42 of the device that contacts the skin during treatment (and thus at any desired distance from the target surface). Embodiments of device 10A that include optics 16 downstream of radiation engine 12 are referred to herein as "indirect exposure" embodiments.

Control systems 18 may be configured to control one or more components of device 10A (e.g., radiation engine 12, fans 34, displays 32, etc.). Control systems 18 may include, for example, any one or more of the following: a radiation source control system for controlling aspects of the generation, treatment, and delivery of energy beams 60 to the user; a displacement-based control system for controlling aspects of device 10A based on the determined displacement of device 10A across to the skin (e.g., as device is glided across the skin during treatment), e.g., relative to a prior treatment position; a temperature control system; an eye safety control system to help prevent exposure of the eyes (e.g., the corneas) to the treatment radiation (an eye safety control system may be omitted in embodiments in which the laser radiation emitted from device 10A is inherently eye-safe, e.g., certain direct exposure embodiments of device 10A); and/or a battery/power control system.

Control systems 18 may include one or more sensors 26 and/or user interfaces 28 for facilitating user interaction with device 10A, and control electronics 30 for processing data (e.g., from sensors 26 and/or user interfaces 28) and generating control signals for controlling various components of device 10A. Control electronics 30 may include one or more processors and memory devices for storing logic instructions or algorithms or other data. Memory devices may include any one or more device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms to perform at least the various functions of device 10A discussed herein. Control electronics 30 may include exclusively analog electronics or any combination of analog and digital electronics.

Control systems 18 may control components or aspects of device 10A based on feedback from sensors 26, user input received via user interfaces 28, and/or logic instructions/algorithms. For example, control systems 18 may be configured to control one or more operational parameters of device 10A. For example, control systems 18 may control the treatment level (e.g., low power level, medium power level, or high power level) or treatment mode (e.g., gliding mode vs. stamping mode; or rapid-pulse mode vs. slow-pulse mode; or initial treatment mode vs. subsequent treatment mode; etc.), the status of radiation source 14 (e.g., on/off, pulse-on time, pulse-off time, pulse duty cycle, pulse frequency, temporal pulse pattern, etc.), parameters of the radiation (e.g., radiation wavelength, intensity, power, fluence, etc.), the configuration or operation of one or more optical elements (in certain indirect exposure embodiments), and/or any other aspects of device 10A.

Control systems 18 may also be configured to control the collection, processing/pre-processing, and transmission of data collected by one or more processors and/or microcontrollers and one or more sensors 26 of device 10A, e.g., for remote processing and user feedback regarding device usage and/or skin quality parameters, as discussed above. In particular, control systems 18 may be configured to control the transmission of collected device and sensor data via a wireless transmission module 2 integrated within device 10A, or alternatively, the communication of collected device and sensor data to a wireless transmission module 2 provided in a docking/charging station 6, via a physical or wireless communication link between device 10A and the docking/charging station 6 (e.g., after each treatment session).

Control systems 18 are discussed in more detail below with reference to FIG. 13.

User interfaces 28 may include any systems for facilitating user interaction with device 10A. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touch screens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Power supplies 20 may include any one or more types and instances of power supplies or power sources for generating, conditioning, or supplying power to the various components of device 10A. For example, power supplies 20 may comprise one or more rechargeable or non-rechargeable batteries, capacitors, super-capacitors, DC/DC adapters, AC/DC adapters, and/or connections for receiving power from an outlet (e.g., 110V wall outlet). In some embodiments, power supplies 20 include one or more rechargeable or non-rechargeable batteries, e.g., one or more Li containing cells or one or more A, AA, AAA, C, D, prismatic, or 9V rechargeable or non-rechargeable cells.

FIG. 7 shows one example embodiment of the portable radiation-based treatment device 10A shown in FIG. 7, wherein the device is a single-beam laser-based fractional treatment device, according to an example embodiment. The example single-beam laser-based fractional treatment device 10A includes a single laser beam source 14, e.g., a single laser diode, high fill-factor laser diode bar, or VCSEL chip arranged just behind an output window 44 at the treatment end 42 of the device. The device 10A may include electronics configured to pulse the single laser beam source 14 to deliver, during each pulse, a single contiguous beam to the skin to generate a single treatment spot on the skin per pulse. The device 10A may be configured for manual movement across the skin to create an array of treatment spots on the skin.

Figure 8A:
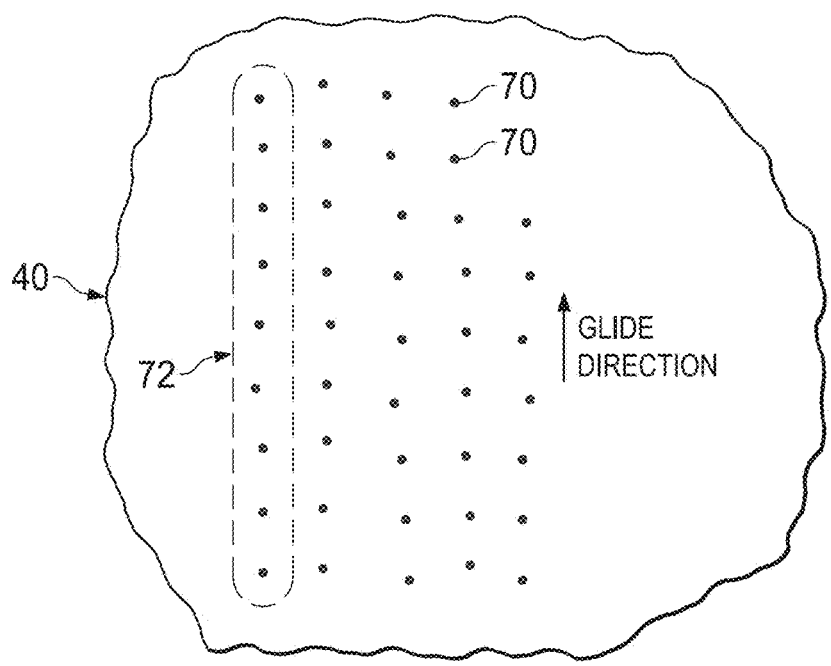
FIG. 8A illustrates an example pattern of treatment spots generated by a portable radiation-based treatment device according to FIG. 7, and including a single beam source, according to an example embodiment.

FIG. 8A illustrates an example array of treatment spots 70 generated on the skin by the device of FIG. 8. Each manual glide of the device across the skin may generate a one-dimensional array 72 of spots 70 along the glide direction.

Figure 8B:
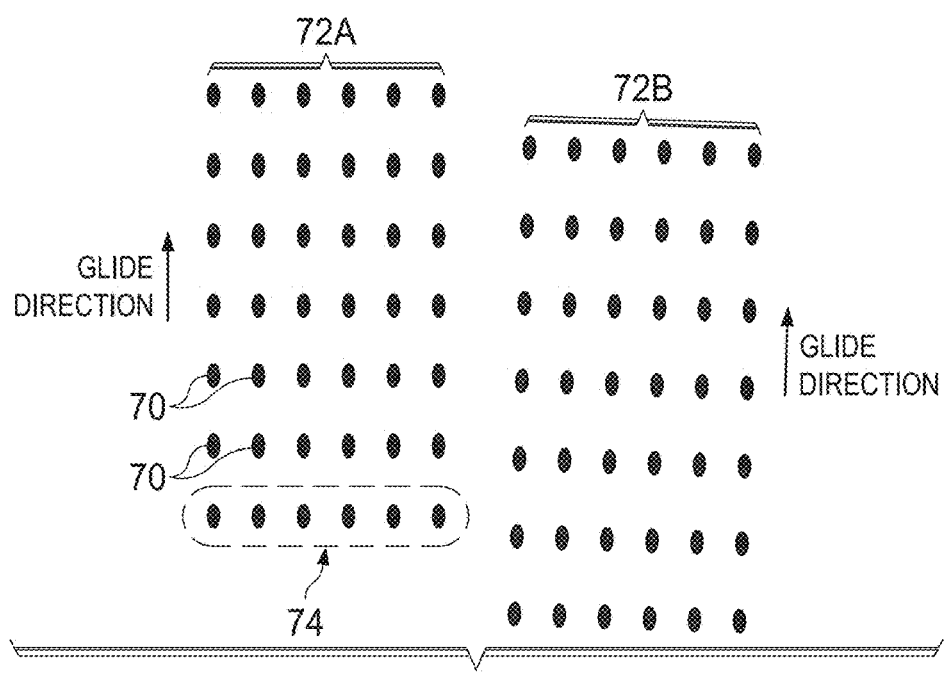
FIG. 8B illustrates an example pattern of treatment spots generated by a portable radiation-based treatment device according to FIG. 7, and including multiple simultaneously-pulsed beam sources, according to an example embodiment.

In an alternative embodiment, device 10A of FIG. 8 may include multiple beam sources, e.g., multiple laser diodes, one or more laser diode bars, or one or more VCSEL chips, configured to generate an array of treatment spots 70 during a simultaneous pulsing of the multiple radiation sources. FIG. 8B illustrates an example array of treatment spots 70 generated by a device having a row of beam sources aligned in a direction perpendicular to the glide direction of the device. Thus, each pulsing of the multiple radiation sources simultaneously generates a row 74 of spots 70, and each manual glide of the device across the skin generates a two-dimensional array 72A, 72B of spots 70.

Figure 6:
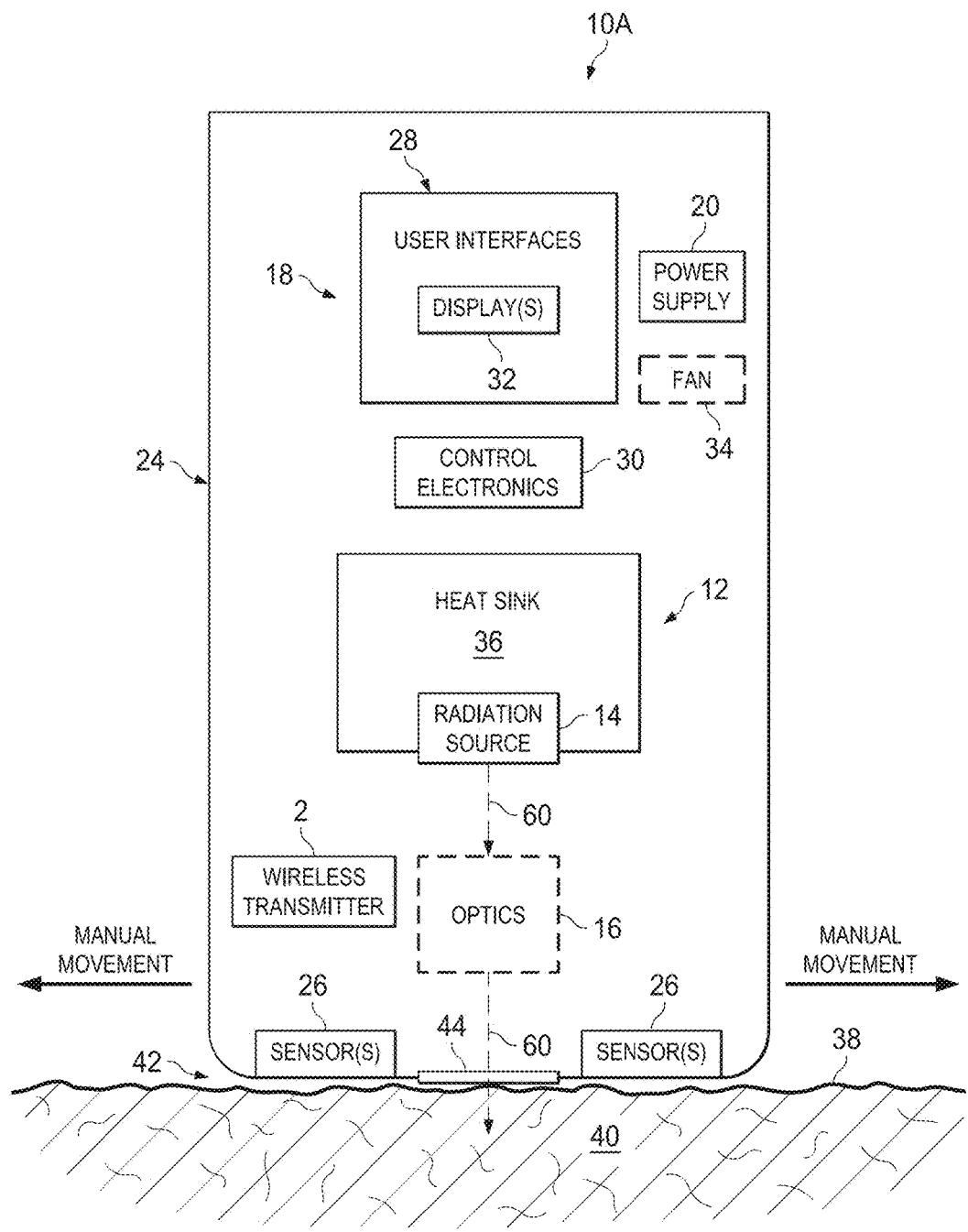
FIG. 6 is a schematic of a first example portable radiation-based treatment device for use in the internet-connected system of FIG. 1, according to an example embodiment.
Figure 9:
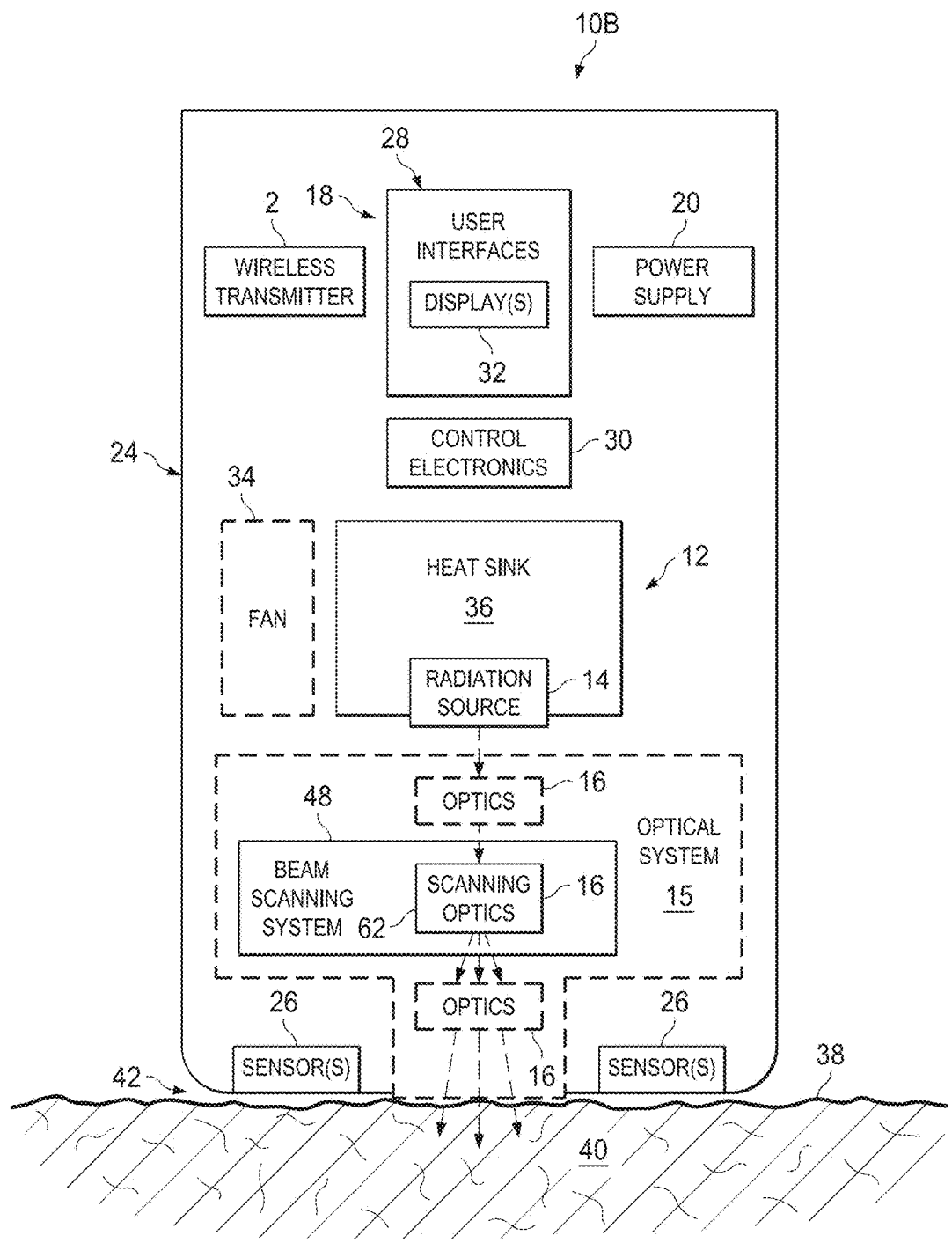
FIG. 9 is a schematic of a second example portable radiation-based treatment device for use in the internet-connected system of FIG. 1, which includes a scanning system to deliver a scanned array of beams to the skin, according to an example embodiment.

FIG. 9 illustrates another example radiation-based fractional treatment device 10B for use in the internet-connected system 1 shown in FIG. 1, according to certain embodiments. Unlike device 10A shown in FIGS. 6-7, device 10B of FIG. 9 includes an automated, motor-driven optical scanning system that scans an input beam to multiple different locations on the skin, to generate multiple discrete treatment spots 70 on the skin. Thus, in addition to the components of device 10A, device 10B may include an optical system 15 for scanning, conditioning, and/or delivering a series of scanned beams to the skin 40.

Optical system 15 is configured for scanning, delivering, conditioning, and/or otherwise controlling or affecting radiation from radiation source 14 to the target surface (e.g., the skin), and may include any number and/or type(s) of optics, or optical elements, 16 for providing such functionality. In some embodiments, optical system 15 includes (a) a beam scanning system 48 including any suitable optics 16 configured to convert, or "scan," an input beam (e.g., a pulsed or CW input beam) into a successive series of output beams for delivery to the skin, and (b) any other optical elements 16 (if any) upstream and/or downstream of the scanning system 48. The optics 16 of scanning system 48 are indicated in FIG. 9 as scanning optics 62.

Figure 10A:
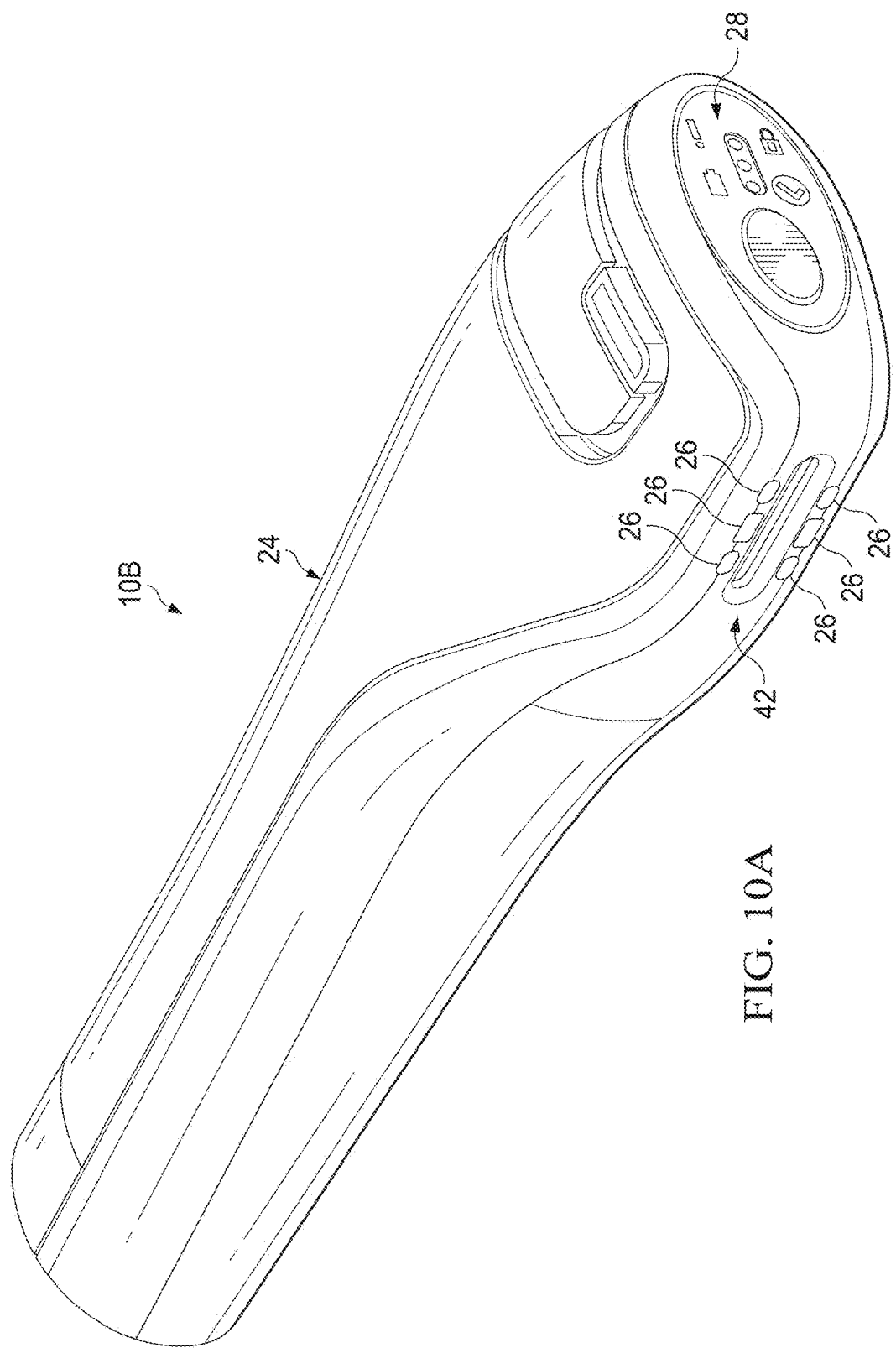
FIG. 10A is an external view of one example configuration of the example portable radiation-based treatment device of FIG. 9, according to an example embodiment.
Figure 10B:
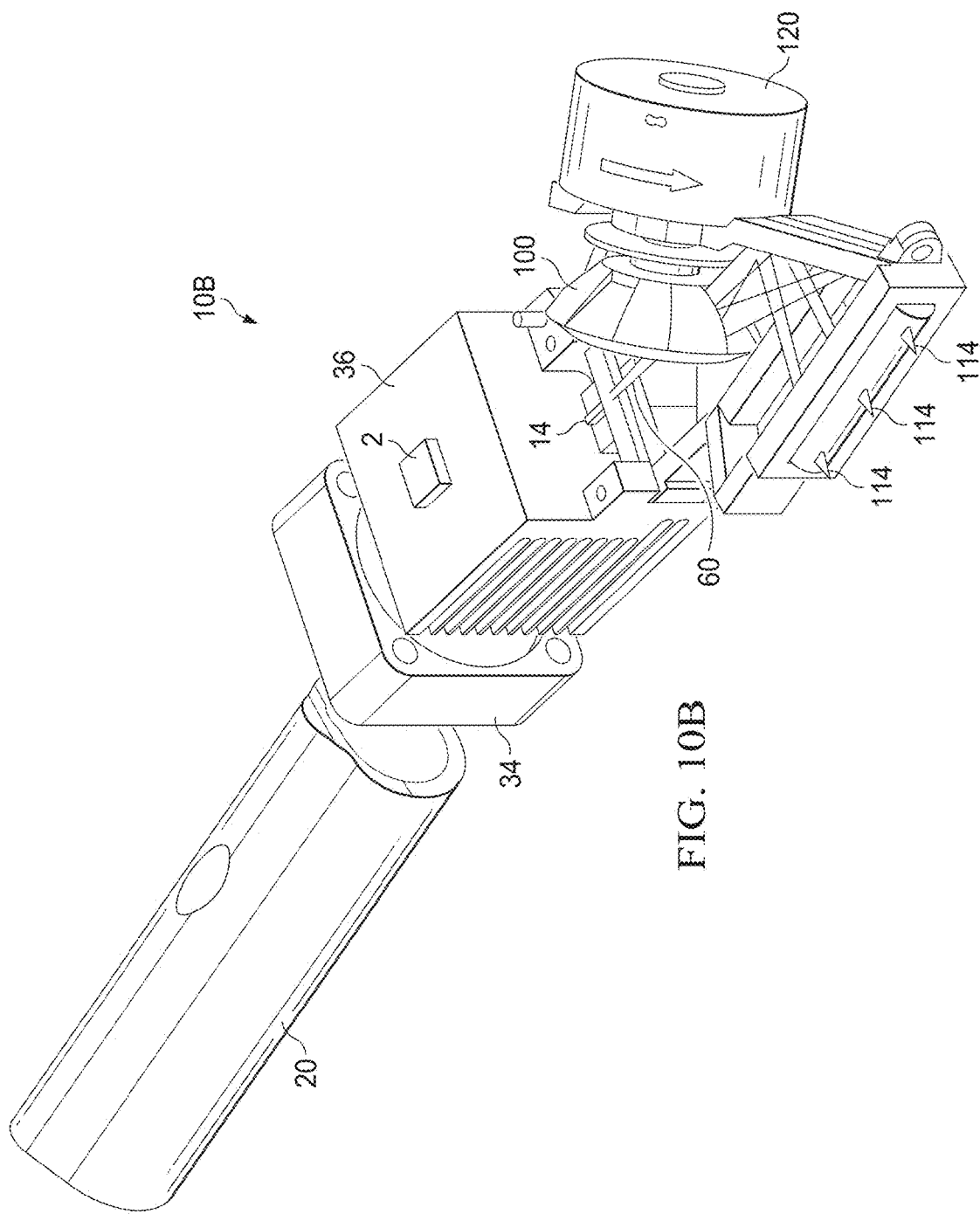
FIG. 10B illustrates the configuration of internal components of the example device shown in FIG. 10A, including the beam scanning system, according to an example embodiment.

FIGS. 10A-10B shows one example embodiment of the portable radiation-based treatment device 10B shown in FIG. 9, wherein the device is a "scanning" fractional treatment device that scans an input laser beam to provide a series of scanned output beams that generate an array of spaced-apart treatment spots 70 on the skin. FIG. 10A shows an exterior view of the scanning fractional treatment device 10B, while FIG. 10B shows the arrangement of various internal components of the device 10B.

As shown, the example scanning fractional treatment device 10B may include a laser beam source 14, e.g., a laser diode, laser diode bar, or VCSEL chip that emits a beam 60 toward a rotating optical scanning element 100 (e.g., lens) driven by a motor 120. The rotating scanning element 100 includes multiple sectors, or "lenslets," around the circumference of the element 100, wherein each lenslet deflects the received input beam 60 by a different amount, such that as the scanning element 100 rotates, the input beam is sequentially deflected by the different lenslets, resulting in a sequential generation of output beams 114 delivered to the skin 70. Each output beam 114 generates a discrete, spaced-apart treatment spot 70 in the skin. The multiple output beams 114 are aligned along a beam scanning direction, and the device 10B is manually glided by the user along a glide direction generally perpendicular to the beam scanning direction, thereby generating a two-dimensional array of spots 70 on the skin for each manual glide of the device.

Figure 11A:
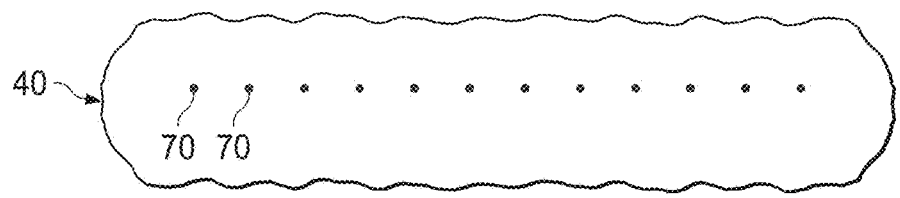
FIG. 11A illustrates an example pattern of treatment spots generated by the beam scanning system of a portable radiation-based treatment device according to FIGS. 10A-10B, with the device held stationary on the skin.
Figure 11B:
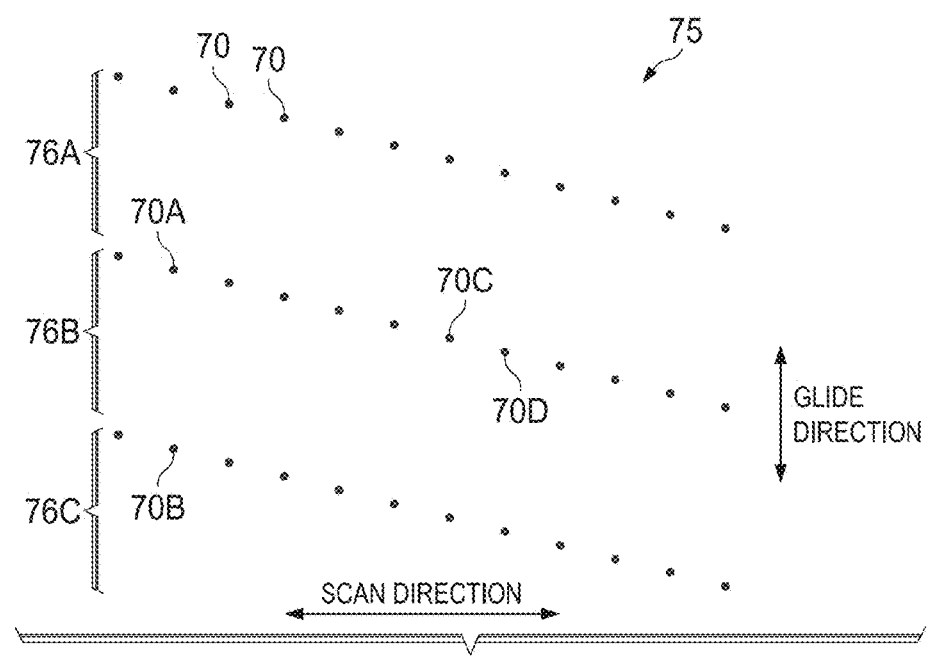
FIG. 11B illustrates an example pattern of treatment spots generated by the beam scanning system of a portable radiation-based treatment device according to FIGS. 10A-10B, with the device being manually glided across the surface of the skin.

FIG. 11A illustrates an example array of treatment spots 70 generated on the skin by the device of FIG. 10B being held stationary in the skin, for one rotation of the rotating scanning element 100. FIG. 11B illustrates a two-dimensional array of spots 70 generated on the skin by manually gliding device 10B across the skin, where each rotation of the scanning element 100 generates a row 76A, 76B, 76C of spots 70.

Figure 12:
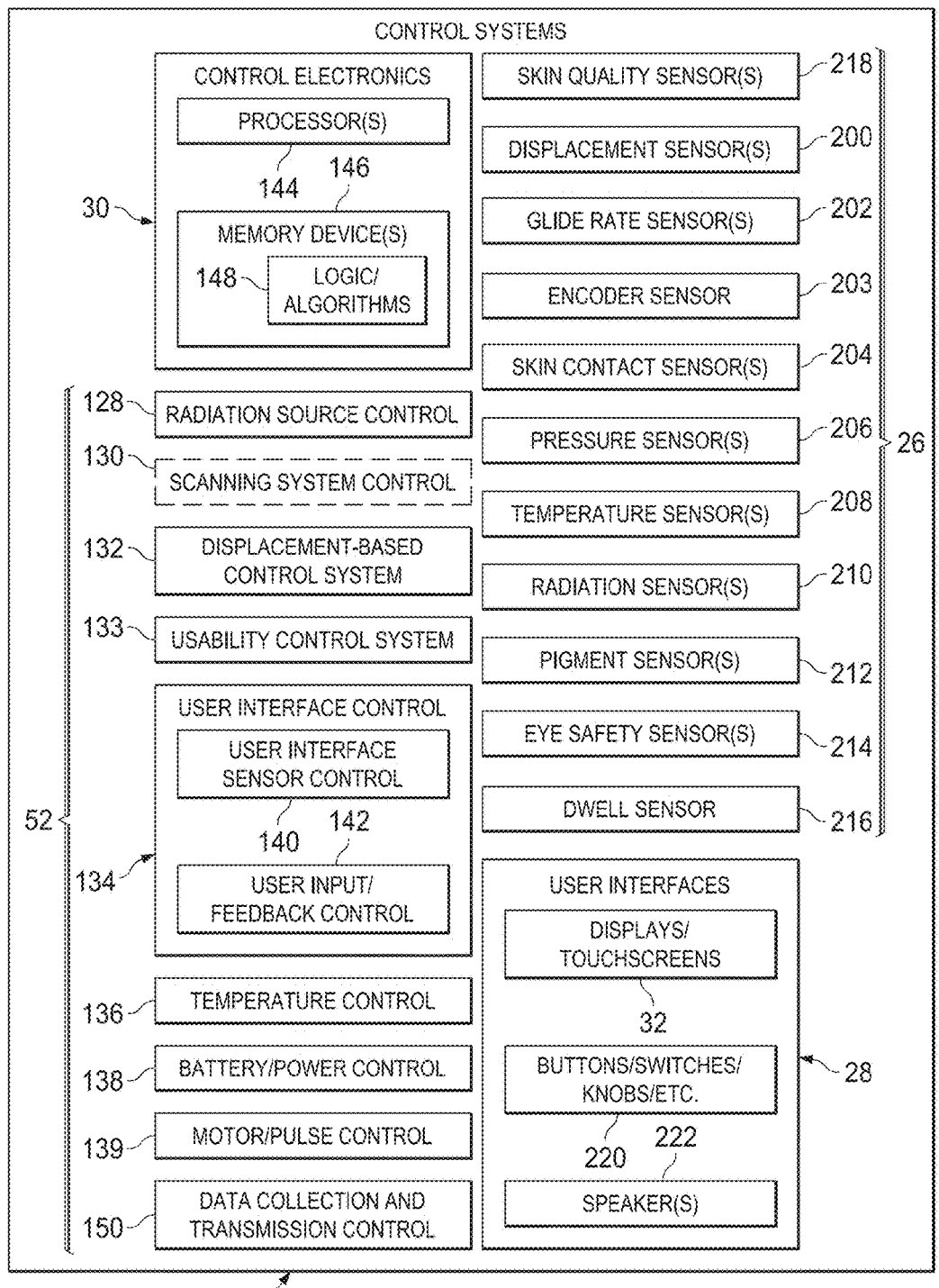
FIG. 12 illustrates an example control system for a portable treatment device, e.g., the portable treatment device as shown in FIG. 6-7 or the portable treatment device as shown in FIGS. 9-10B, according to example embodiments.

FIG. 12 illustrates example components of control systems 18 for controlling aspects of any respective device 10, e.g., device 10A or 10B discussed above, according to certain embodiments. Control systems 18 may include control electronics 30, sensors 26, user interfaces 28, and a number of control subsystems 52. Control subsystems 52 are configured to control one or more components of device 10 (e.g., radiation source 14, fans 34, displays 32, etc.). In some embodiments, control subsystems 52 may include any or all of a radiation source control system 128, a scanning system control system 130, a displacement-based control system 132, a usability control system 133, a user interface control system 134, a temperature control system 136, a battery/power control system 138, a motor/pulse control system 139, a data collection and transmission control system 150, and/or any other suitable control systems for controlling any of the functionality disclosed herein. User interface control system 134 may include a user interface sensor control system 140 and a user input/display/feedback control system 142.

Each control subsystem 52 may utilize any suitable control electronics 30, sensors 26, user interfaces 28, and/or any other components, inputs, feedback, or signals related to device 10. Further, any two or more control subsystems 52 may be at least partially integrated. For example, the functionality of control subsystems 52 may be at least partially integrated, e.g., such that certain algorithms or processes may provide certain functionality related to multiple control subsystems 52.

Control electronics 30 may include one or more processing devices 144 and memory device 146 for storing logic instructions or algorithms 148 or other data. Memory devices 146 may include any one or more device for storing electronic data (including logic instructions or algorithms 148), such as any type of RAM, ROM, Flash memory, or any other suitable volatile and/or non-volatile memory devices. Logic instructions or algorithms 148 may be implemented as hardware, software, firmware, or any combination thereof. Processing devices 144 may include any one or more devices, e.g., one or more microprocessors and/or microcontrollers, for executing logic instructions or algorithms 148 to perform at least the various functions of device 10 discussed herein. Control electronics 30 may include exclusively analog electronics or any combination of analog and digital electronics.

Sensors 26 may include any one or more sensors or sensor systems for sensing or detecting data regarding device 10, the user's skin, the operating environment, or any other relevant parameters. For example, sensors 26 may include one or more of the following types of sensors:

(a) At least one displacement sensor 200 for detecting, measuring, and/or calculating the displacement of device 10 relative to the skin 40, or for generating signals from which the displacement is determined. In some embodiments, displacement sensor 200 may be a single-pixel sensor configured to determine a displacement of device 10 by identifying and counting intrinsic skin features in the skin. In particular embodiments, a single-pixel displacement sensor 200 may double as a skin texture sensor, e.g., as discussed below. For example, a dual-use displacement sensor/skin texture sensor may include an LED emitter and detector separated by an opaque barrier and placed in close proximity with the skin without any intervening optics. In other embodiments, displacement sensor 200 may be a multiple-pixel sensor, such as a mouse-type optical imaging sensor utilizing a two-dimensional array of pixels.

(b) At least one motion/speed sensor 202 for detecting, measuring, and/or calculating the rate, speed, or velocity of device 10 moving across the treatment area 40 (the "manual glide speed"), or for generating signals from which the manual glide speed is determined;

(c) At least one encoder sensor 203 for detecting the rotation and/or position of an encoder fixed to a scanning system motor 120, e.g., in a scanning fractional device such as device 10B discussed above.

(d) At least one skin-contact sensor 204 for detecting contact between device 10 and the skin or treatment area 40. For example, device 10 may include one or more capacitive contact sensors 204 for detecting contact with the user's skin. As discussed below regarding skin quality sensors 218, one or more capacitive contact sensors 204 may double as a skin moisture sensor, as the coupling capacitance between the capacitive stack and the skin is sensitive to skin moisture content, wherein higher moisture yields higher capacitance.

(e) At least one pressure (or force) sensor 206 for detecting the pressure (or force) of device 10 against the skin or treatment area 40.

(f) At least one temperature sensor 208 for detecting the temperature of the treatment area 40, a region of the treatment area 40 (such as the treatment spot 70 before, during, and/or after treatment), components of device 10, or other object.

(g) At least one radiation sensor 210 for detecting levels or other parameters of radiation delivered to the treatment area 40 or indicative of the radiation delivered to the treatment area 40 (e.g., per light pulse, per individual beam/treatment spot, per delivered array of scanned beams/treatment spots 70, per a specific number of individual delivered beams/treatment spots 70 or scanned arrays of beams/treatment spots 70, or per a specific time period). For example, device 10 may include a photodiode to measure the pulse duration of the treatment beam.

(h) At least one color/pigment sensor 212 for detecting the color or level of pigmentation in the treatment area 40, e.g., to provide a safety feature by enabling the radiation source 14 only when the detected skin color/pigment meets predefined condition(s).

(i) At least one eye safety sensor 214 for helping to prevent unwanted eye exposure to light from the treatment radiation source 14. Example eye safety sensors 214 are discussed below with reference to FIGS. 48-51.

(j) At least one dwell sensor 216 for detecting whether device 10 is stationary or essentially stationary with respect to the skin.

(k) At least one skin quality sensor 218 configured to detect various signals indicative of one or more parameters of the user's skin. Example skin quality sensors include the following:

Skin moisture sensor. As discussed above, device 10 may use one or more capacitive skin sensors as skin contact sensors 204 to control the activation or triggering of treatment energy source (e.g., laser), e.g., to prevent unwanted radiation delivery for eye safety, overtreatment, or other reason. In some embodiments, this capacitive sensor or sensors can also be used to measure skin moisture. For example, a capacitive sensor may be formed by a thin insulator (e.g., <1 mm thick plastic) on top of an electrode (e.g., a metallic block or PCB metal trace). The AC signal discharge time is determined by the skin coupling capacitance (typically on the order of several pF) when the stack is placed against the user's skin. This coupling capacitance is sensitive to skin moisture content, wherein higher moisture yields higher capacitance. Fore example, when moisturizer or lotions are applied to skin, the coupling capacitance can be more than doubled. Thus, device 10 may record data and transmit data collected by one more capacitive sensors, e.g., during a treatment session of device 10, which data may be analyzed statistically (e.g., by system 4) to determine a measure of skin moisture content.

Skin tone and redness sensor. Device 10 may include one or more skin tone color sensors. For example, a skin tone sensor may detect optical reflective spectrometry using a photo detector and a set of discrete LEDs of different wavelengths in the visible to near-IR range (~400-~900 nm). Such sensors has previously been integrated in skin care devices as a safety lock to prevent misuse by non-indicated skin types. In some embodiments, system 1 may collect and analyze data from one or more of skin tone color sensors integrated in device 10 in order to analyze the user's skin tone over time. In some embodiments, the skin tone sensor(s) are activated between laser treatment pulses while the device is still placed against the skin, wherein the skin tone sensor(s) acquire reflectance data and process statistics for their variation across the treated area (or transmit the collected sensor data for remote processing by system 4). A time progression of the mean and/or variation of the measured skin tone can be correlated with treatment results.

Skin texture and wrinkle sensor. Skin texture roughness or wrinkle features can be detected using a near-field optical probe, such as the single pixel displacement sensor disclosed in pending application U.S. Ser. No. 13/443,717, filed Apr. 10, 2012, which teachings regarding a single pixel displacement sensor 200 are herein incorporated by reference. Thus, displacement sensor 200 discussed above may double as a skin texture roughness or wrinkle detection sensor. The displacement sensor/skin texture sensor may include an LED emitter and detector separated by an opaque barrier and placed in close proximity with the skin without any intervening optics (or in an alternative embodiment, including a lens located between one or both of the LED emitter and detector and the skin). The detected signals correspond to the peaks and valleys of the skin features, such that device 10 or system 4 can correlate the overall signal RMS value with the skin roughness. Another alternative is to incorporate a CMOS imager and perform image processing to calculate a roughness and wrinkle index.

Skin thickness, firmness, and aging sensor. This set of skin quality parameters may be measured by optical scattering (with emitter/detector pair and a reference for background subtraction), fluorescence spectroscopy (with deep blue LED excitation), electrical impedance spectroscopy (with inter-digitated electrode pattern of controlled spacing excited by different ac frequencies similar to the drawings in John Beale's note page shown in the previous section), or mechanical impedance measurement (with a vibrator excitation and an accelerometer measuring the phase and amplitude at different frequencies).

User interfaces 28 may include any systems for facilitating user interaction with device 10, e.g., displaying data or providing feedback to a user visually and/or audibly, and/or palpably (e.g., via vibration), and receiving commands, selections, or other input from the user. For example, user interfaces 28 may include one or more displays 32 (one or more of which may be interactive touch screens), one or more manual devices 220 (e.g., buttons, switches, knobs, sliders, touch screens, keypads, etc.), one or more speakers 222, and/or any other devices for providing data, information, or feedback to a user or receiving input or information from a user.

Control subsystems 52 may be configured to control one or more controllable operational parameters of device 10, based on feedback from sensors 26, user input received via user interfaces 28, and/or execution of logic instructions/algorithms 148. As used herein, "controllable operational parameters" may include any aspects or parameters of device 10 that may be controlled by any of control subsystem 52.

Radiation source control system 128 may monitor and control various aspects of radiation source 14. Scanning control system 130 may monitor and control various aspects of laser scanning system 48, e.g., motor 120. User interface control system 134 may include a user interface sensor control system 140 for monitoring and controlling displacement sensor 200, skin contact sensors 204, eye safety sensor 214, and/or other sensors 26. For example, system 134 may receive signals detected by each sensor, and send control signals to each sensor. User interface control system 134 may include a user input/display/feedback control system 142 for monitoring and controlling user interfaces 28 and displays 32. For example, system 134 may receive user input data from various user interfaces 28, and control information communicated to the user via displays 32 (e.g., visually, audibly, tangibly (e.g., by vibration), palpably, etc.). Scanning control system 130 may communicate data or signals with, or otherwise cooperate with, other control subsystems, e.g., radiation source control system 128, scanning control system 130, displacement-based control system 132, usability control system 133, temperature control system 136, battery/charger control system 138, and/or motor/pulse control system 139.

Temperature control system 136 may be configured to monitor and control the temperature of one or more components of device 10, e.g., radiation source 14, motor 120 of scanning system 48, battery 20, etc. Battery/charger control system 138 may be configured to monitor and control the charging of battery 20. Motor/pulse control system 139 may monitor and control various aspects of radiation source 14 and/or scanning system 48.

Data collection and transmission control system 150 is configured to (a) collect data from processing device(s) 144 regarding the usage or operation of device 10 and/or sensor data collected by any of the sensors 26, including any skin quality sensors 218, (b) process or pre-process the collected device usage and/or sensor data, and (c) transmit the collected (and/or processed/pre-processed) device usage and/or sensor data via wireless transmitting device 2, e.g., WiFi module or Bluetooth module, e.g., in real-time or upon the completion of each treatment session. Alternatively, in embodiments in which wireless transmitting device 2 is located in a cradle/docking station 6 rather than being integrated in device 10, data collection and transmission control system 150 may control the transmission of collected (and/or processed/pre-processed) device usage and/or sensor data to the wireless transmitting device 2 upon docking of device 10 in the cradle/docking station 6, e.g., via a wired or short-range wireless communication link.

Any of the skin quality sensors 218 discussed herein may have any suitable optical, electrical, and mechanical hardware implementations. Some example implementations are discussed below.

Optical Skin Sensors

Figure 13:
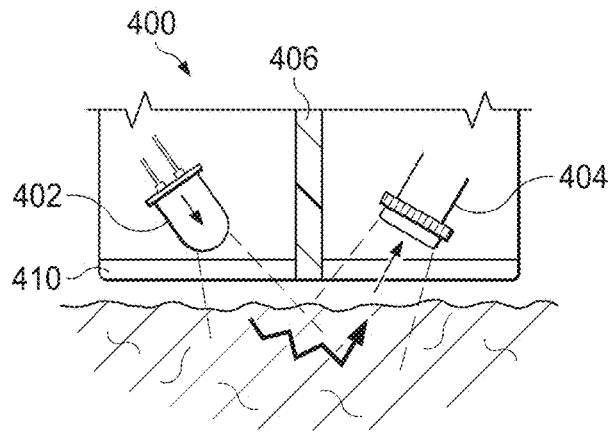
FIG. 13 shows an example optical sensor, according to an example embodiment.

FIG. 13 shows an example optical sensor 400, according to an example embodiment. Sensor 400 includes an light source (e.g., LED) 402 and a detector 404 separated by an opaque barrier 406, and may be arranged behind a window or film 410, which may be placed against the surface of the skin during operation. Detector 404 may be designed to detect radiation at the specific wavelength of light source 402, e.g., to distinguish from treatment radiation or ambient light. The detected radiation signal may indicate a level of absorption for the wavelength of the emitting light source 402.

The opaque barrier 406 is intended to ensure that all light from light source 402 detected by detector 404 actually passes through the skin, i.e., by entering the skin and backscattering toward detector 404. The separation between the light source 402 and detector 404 defines the mean or range of penetration depth of the light passing through the skin before backscattering toward detector 404. Thus, device 10 may include multiple sensors 400 having different light source/detector separations to collect data corresponding to different penetration depths, which data may be collectively analyzed to determine one or more skin quality metrics using any suitable algorithm. In some embodiments, the width of opaque barrier 406 may define an effective separation between light source 402 and detector 404.

In addition, device 10 may include multiple optical sensors 400 using different wavelength light sources 402 (e.g., different color LEDs), to measure the absorption at multiple different wavelengths, which data may be collectively analyzed to determine one or more skin quality metrics using any suitable algorithm.

Figure 14:
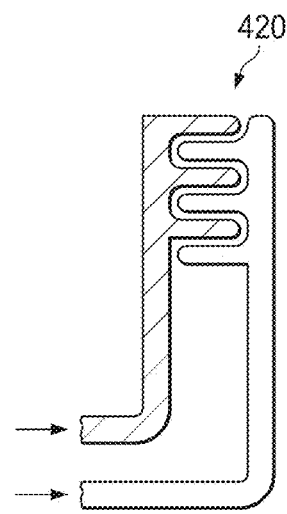
FIG. 14 shows an example interdigitated electrode capacitive sensor, according to an example embodiment.

FIG. 14 shows an example interdigitated electrode capacitive sensor 420, according to an example embodiment. Interdigitated electrode capacitive sensor 420 may be provided via a flex cable arranged in immediate proximity to the skin, and may be configured to detect surface permittivity of the skin.

Figure 15A:
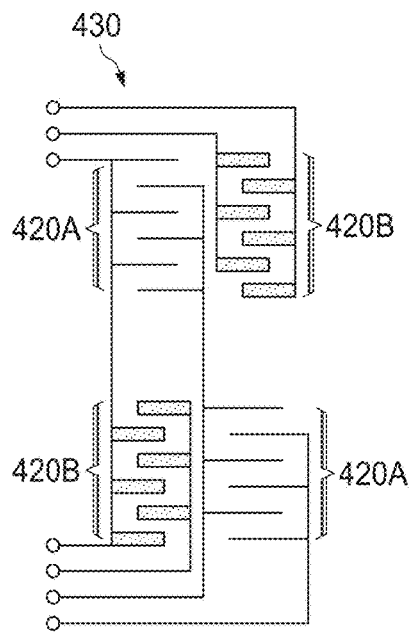
FIGS. 15A and 15B shows an example array of interdigitated electrode capacitive sensors having different spacing patterns, according to an example embodiment.
Figure 15B:
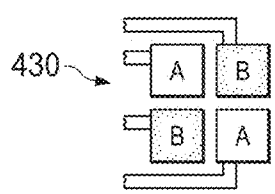

FIGS. 15A and 15B shows an example array of interdigitated electrode capacitive sensors 420 having different spacing patterns, corresponding to different frequencies, according to an example embodiment. The example array includes a first pair of interdigitated electrode sensors 420A having a first spacing pattern arranged in an alternating manner with a second pair of interdigitated electrode sensors 420B having a second spacing pattern larger than the first spacing pattern of sensors 420A. The ratio of capacitance measured by the different-spaced sensors, i.e., capacitance measured by sensors 420A/capacitance measured by sensors 420B (referred to as the capacitance ratio) may provide useful metric(s) or characteristic(s) regarding the skin. For example, the sensor array 430 may be designed such that capacitance ratio is sensitive to small surface variations while controlling for large-scale variations.

Figure 16:
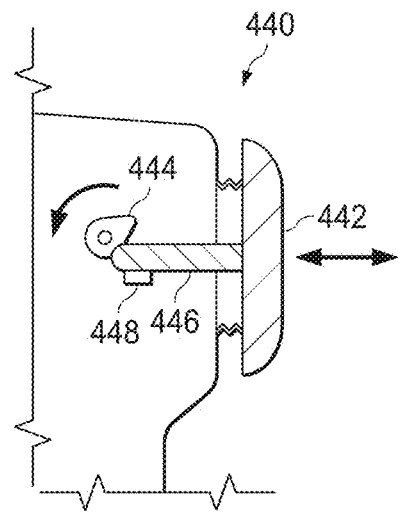
FIG. 16 shows an example mechanical impedance sensor, according to an example embodiment.

FIG. 16 shows an example mechanical impedance sensor 440, according to an example embodiment. The mechanical impedance sensor 440 includes a skin contact tip 442 that is flexibly coupled to the device body 24 (e.g., via springs as shown) and coupled to a motor-driven rotating cam 444 via a connecting member 446, which may also be flexible. An acceleration sensor 446 is coupled to the skin contact tip 442 or connecting member 446. The rotating cam 44 vibrates the skin contact tip 442 along the direction indicated by the arrow. When the tip 442 is placed against the skin, the contact between the tip and skin affects the vibrational movement of the tip 442, which is measured by the acceleration sensor 446. For example, the phase and amplitude of the detected signals can be analyzed and correlated to mechanical properties of the skin.

Gliding-Based Non-Imaging Spectral Sensors

Device 10 may include one or more integrated compact skin color-tone sensors. Some example implementations are discussed below.

FIG. 17A is a side view of a first example configuration of a skin color/tone sensor 460A, according to an example embodiment, and FIG. 17B is a cross-sectional view taken along line A-A shown in FIG. 17A. The sensor 460A includes a light source 462, e.g., a white LED or single-wavelength LED, and a detector 464, e.g., an integrated color-sensing detector which may simultaneously measure red, green, blue and/or infrared wavelength ranges of light. The light source 462 and detector 464 are arranged behind a lens 466, for example a cylindrical lens (or "rod lens"). The lens 466 allows the light to propagate along the axial direction of the lens, as shown in FIG. 17A, but focuses the light emitted by light source 462 into the skin in the direction perpendicular to the axial direction of the lens, and then after reflecting/remitting from the skin, into the detector 464 along that same direction, as shown in FIG. 17B.

In one embodiment, the emitter 462 and detector 464 use the same lens 466 (e.g., rod lens) that is used for focusing treatment light originating from the device radiation source 14 onto the skin. An opaque barrier 470A between the emitter and detector prevents direct passage of light from the emitter 462 to the detector 464 without reflecting/remitting from the skin. In addition, the lens 466 may be arranged between, or partially surrounded by, opaque or reflective structures 472, as shown in FIG. 17B.

FIG. 18 shows an alternative configuration of example configuration of the skin color/tone sensor, indicated at 460B, in which the opaque barrier 470B extend through the lens 466 such that are lens is divided into two separate sections 466A dna 466B. The separate lens arrangement prevents unwanted internal reflections of the source light within the lens from increasing the baseline offset of the detector 464 when no skin is present.

Figure 19A:
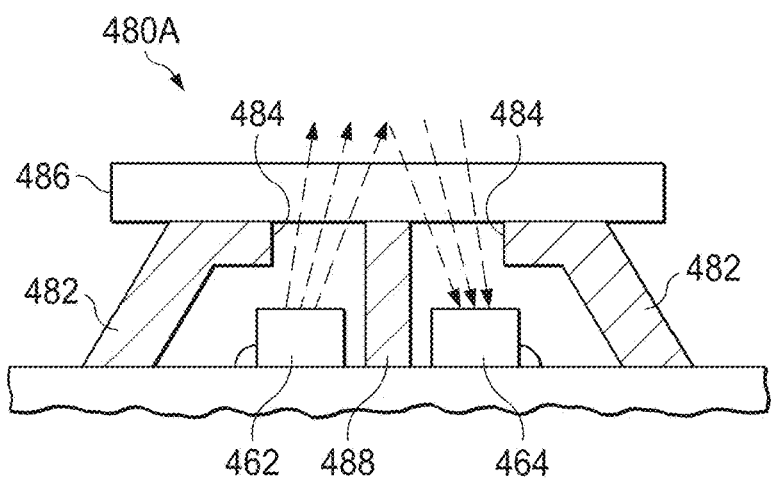
FIG. 19A is a cross-sectional view of an example configuration of a skin color/tone sensor including a window but no optics, according to an example embodiment.

FIG. 19A is a cross-sectional view of another example embodiment of a skin color/tone sensor 480A, according to an example embodiment. In this embodiment, the light source 462 and detector 464 are arranged behind an opaque cap 482 that includes one or two apertures 484 and a planar transparent window or film 486 arranged over the cap 482. Using two apertures reduces the internally-reflected light. As discussed above, an opaque barrier 488 may be arranged between the light source 462 and detector 464.

Figure 19B:
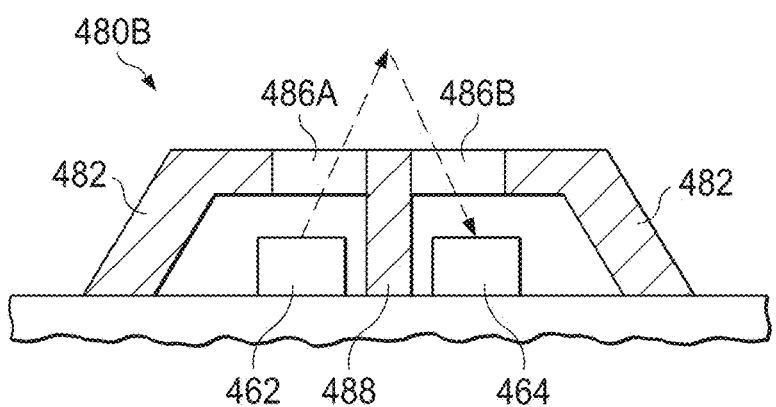
FIG. 19B is a cross-sectional view of an example configuration of a skin color/tone sensor including a cap with integrally formed windows, but no optics, according to an example embodiment.

FIG. 19B illustrates another embodiment another example embodiment of a skin color/tone sensor 480B, wherein the transparent window is integrated into the opaque cap as window portions 486A and 486B, for example in a co-molding process.

Figure 20:
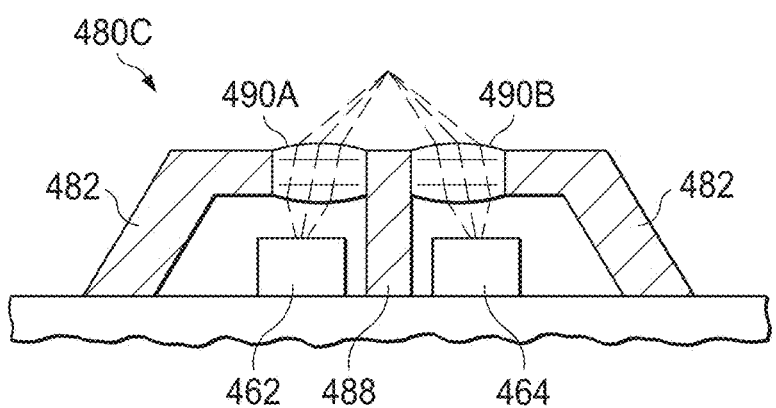
FIG. 20 is a cross-sectional view of an example configuration of a skin color/tone sensor including separate lenses for the light source and the detector, according to an example embodiment.

FIG. 20 illustrates another embodiment another example embodiment of a skin color/tone sensor 480C, wherein powered optics (e.g. lenses) 490A and 490B are used in place of the planar windows to collect more of the source light into the detector 464, and also to decrease the illuminated and/or sensed region of the skin, which may increase the spatial resolution of the system, thereby giving color reflectance information on a smaller length scale.

Gliding-Based Dielectric Property Sensor

As another example, sensors 218 may include an electronic sensor that measures dielectric properties to determine skin parameters such as relative skin thickness, elasticity, and moisture. The dielectric properties of cutaneous and subcutaneous tissue may be non-invasively measured by one or more electrodes which are applied either in contact with, or some distance above, the surface of the skin. These electrodes need not make direct electrical contact with the skin, as DC and AC electric fields extend through electrically insulating layers. They can acquire measurements of local material properties as the sensor is moving over the surface of the skin.

The dielectric properties of the volume probed by the electric fields may be measured by determining the effective capacitance and dissipation of the electrode structure. In general the dielectric permittivity can be expressed as a complex number with the real part representing polarizability, which determines the effective capacitance, and the imaginary part representing dissipation or energy loss, which can be modeled as a resistive element either in series or parallel with the effective capacitance caused by polarization. The complex permittivity of a material is a function of the frequency of the applied field.

There are several physical mechanisms contributing to permittivity including electronic and atomic polarization, and dipole and ionic relaxation. The latter two relaxation mechanisms contribute measurable responses in the frequency range of kHz and MHz, which is conveniently measured by capacitive electrodes.

The electrical permittivity, and especially the dissipation or loss tangent as a function of frequency in the kHz and MHz frequency range, can be used as a probe of the material composition of tissue. It is a function of the chemical composition of the material and ionic concentration, as well as local viscosity. It is also affected by temperature and other factors, but with temperature held constant, a change in measured permittivity can be used as a measure of a change in the tissue properties.

The real portion of the permittivity, measured as capacitance, is a combined function of the distance separating the electrodes and the skin, as well as the material properties of the skin tissue itself. Using a differential measurement which compares the sensed values between electrode patterns having different geometry and inter-element spacing, optionally in conjunction with other contact or distance sensors, the capacitance contribution of electrode-skin distance and intrinsic skin properties may be separated. With the capacitance contribution of the electrode to skin surface a known value, additional changes in the capacitance value may be interpreted as differences in skin thickness as well as moisture content. Water has a very high dielectric constant, and so dry skin has a lower capacitance value.

Capacitance sensors applied to skin are in general sensitive to the amount of pressure applied. This is more pronounced over softer tissue areas, and less so over bony areas. The reason is that the compliant skin is formed around the shape of the device containing the sensing electrode and thus its dielectric intercepts more of the electric field lines. The capacitance change due to applied force may be distinguished from a change due to intrinsic skin properties by using more than one capacitive sensor electrode as discussed below.

Figure 21A:
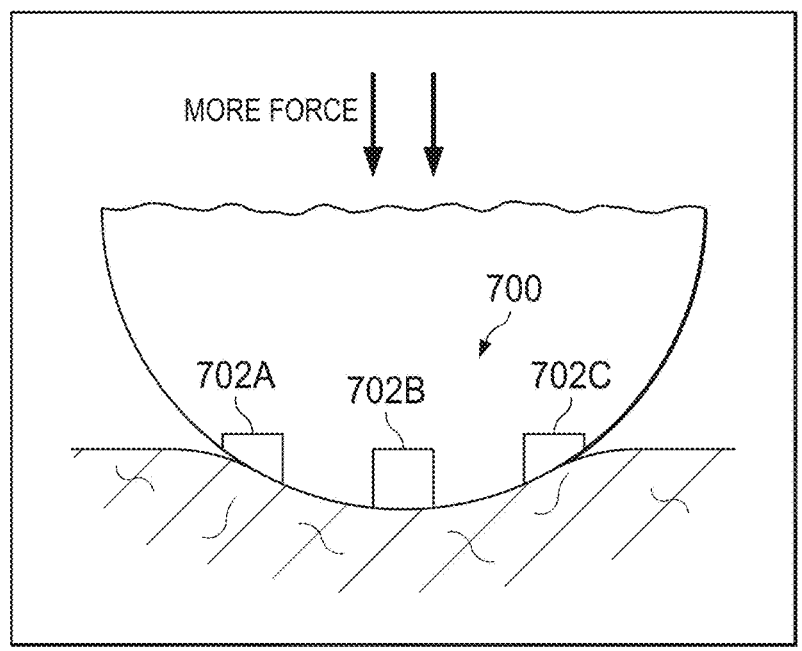
FIGS. 21A and 21B illustrate a dielectric sensor having multiple electrodes arranged on a non-planar surface, according to an example embodiment.
Figure 21B:
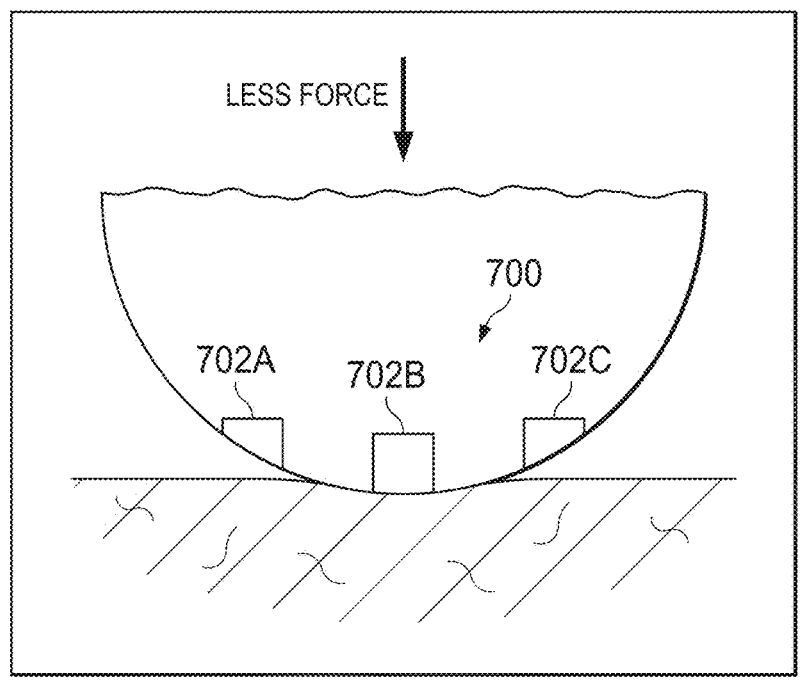

FIGS. 21A and 21B illustrate a dielectric sensor 700 having multiple electrodes arranged on a non-planar surface, according to an example embodiment. In this example, a probe with a rounded tip shape contains three electrodes 702A-702C. The central electrode 702B will detect a larger value in comparison to peripheral electrodes 702A and 702C when there is light pressure against the skin and only 702B is in close proximity. With heavier pressure, the skin surrounds more of the probe tip surface and electrodes 702A and 702C, now being in closer proximity to the skin see a capacitance value which becomes closer to electrode 702B.

Device 10 or data analysis system 4 may implement a suitable algorithm that collectively analyzes the separately measured capacitances from the electrodes 702A-702C to remove or reduce the effect of probe contact area variation from skin deflection on the overall measured capacitance, thus providing an improved measure of underlying variations due to skin properties as the tip is moved laterally across the skin surface, and between different skin regions or even different individuals.

One advantage of this sensor embodiment is that the active surface of the probe is composed of a pattern of electrical conductors (electrodes) which create an electric field, but need not make direct electrical (galvanic) contact with the skin. This eliminates some electrical hazards to both the device and the user, and permits the sensor to be concealed behind an opaque surface so that it does not affect the aesthetics of the device. Another advantage is that using a non-contact probe one can evaluate skin health based on measurements that are related to skin thickness, moisture content and elasticity. This hardware implementation is especially useful for compact and low-cost integration onto a portable dermatological treatment device. Still another advantage is that lab measurement of the single parameter of skin thickness using electrical impedance spectroscopy has been shown in the lab, but not previously in a method practical for a home use treatment system. Thus, the sensor provides a compact and easy to use probe, suitable for integration into a handheld home-use device 10, and capable of measuring multiple useful skin properties.

CMOS Imaging Spectral Sensor

Another type of skin quality sensor 218 that may be integrated into device 10 is an imaging sensor or imaging device. For example, a CMOS imaging chip can be integrated with a white light source and appropriate imaging optics to provide a spectral imaging map of a larger skin area.

Figure 22:
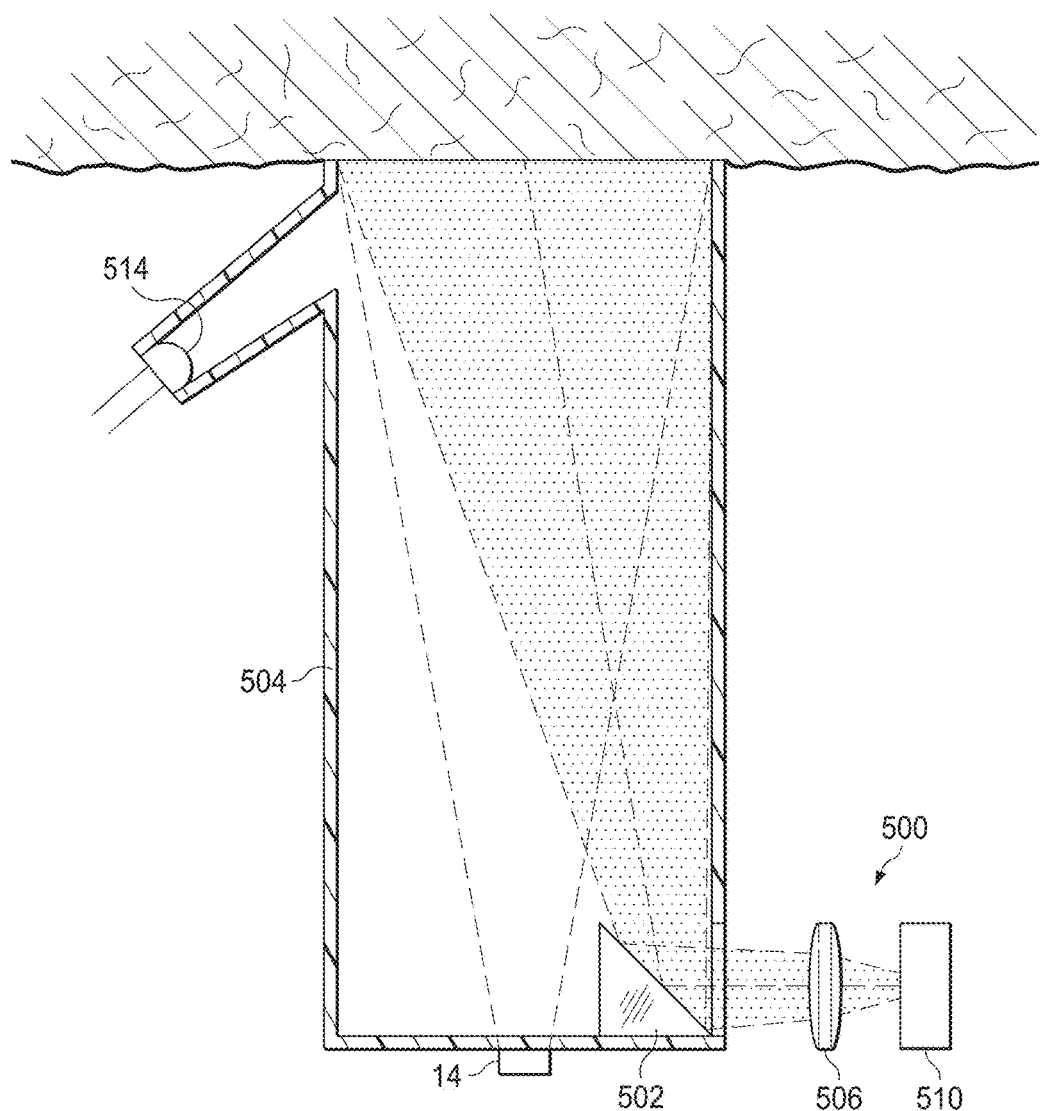
FIG. 22 illustrates a cross-sectional side view of a light delivery structure including an integrated imaging sensor configured to provide a spectral imaging map of a skin area, according to an example embodiment.
Figure 23:
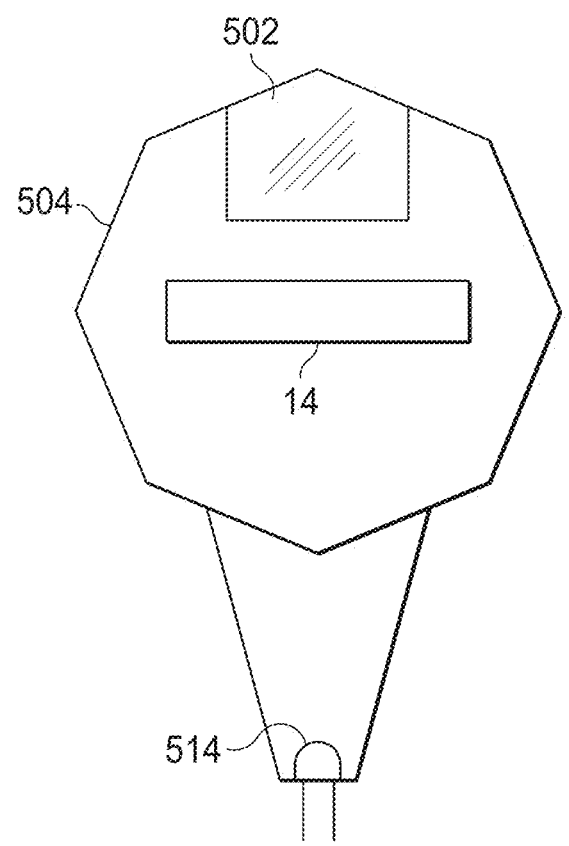
FIG. 23 illustrates an end-view of the light delivery structure of FIG. 22, from the perspective of the skin, according to an example embodiment.

FIGS. 22 and 23 illustrate a CMOS imaging device 500 for use in a hair removal device 10, according to an example embodiment. However, it should be understood that a similar CMOS imaging device may be integrated into a fractional treatment device 10 or any other type of dermatological device 10. FIG. 22 is a side cross-sectional view of the CMOS imaging device 500 arranged against the skin, and FIG. 23 is an end view of device 500 from the perspective of the skin.

As shown, CMOS imaging device 500 includes a reflective element 502 arranged within a light pipe 504 used for delivery of treatment radiation from a laser diode bar 14 to the skin (in this example, an octagonal glass or clear plastic lightpipe). The CMOS imaging device 500 also includes focusing optics 506 configured to focus an image of the skin onto a CMOS imaging chip 510. Thus, the imaging chip 510 is capable of imaging the same area of skin currently under treatment or ready for treatment from laser diode bar 14. In this example, the reflective element 502 is a small right-angle prism set into a notch in the lightpipe 504, which turns the optical path to look toward the output end of the lightpipe in contact with the skin. A white LED 514 is mounted near the other end of the lighpipe 504 to provide visible light illumination to improve the imagine and/or allow imagining when the laser diode bar 14 is inactive.

As discussed below with reference to FIGS. 24-28B, images captured by CMOS imaging device 500 can be processed using different algorithms to calculate multiple different skin quality metrics, such as skin texture smoothness/roughness and skin color/tone, for example.

Figure 24:
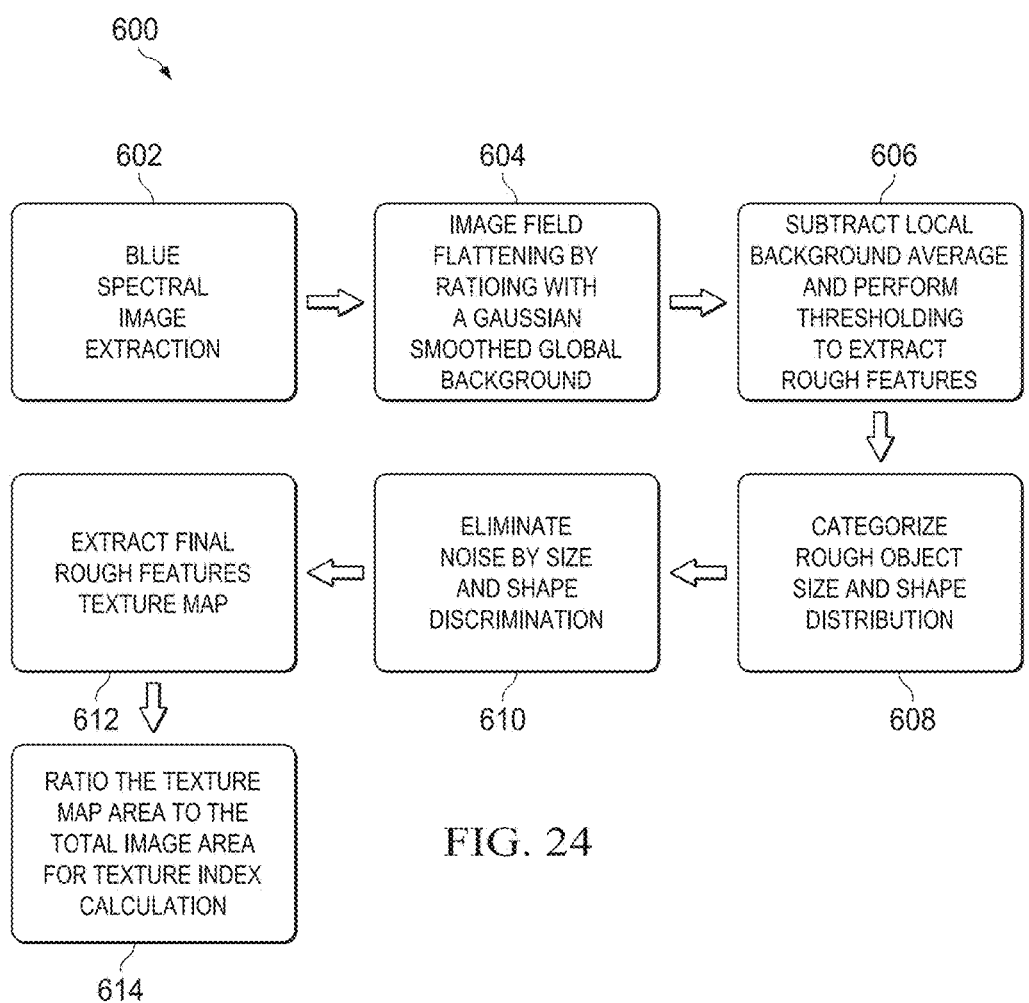
FIG. 24 is a process flow of a spectral analysis algorithm for analyzing skin texture, according to an example embodiment.

FIG. 24 is a process flow of a spectral analysis algorithm 600 for analyzing skin texture based on an image of the skin, e.g., captured by CMOS imaging device 500 or other type of imaging sensor 218, according to an example embodiment. The three primary colors used for spectral analysis are red (~615 nm), green (~525 nm), and blue (~465 nm). It has been discovered that the blue color is most sensitive and provides the highest spatial resolution for skin texture detection. Thus, the algorithm 600 begins at step 602 by performing a blue spectral image extraction from the captured image. At step 604, the effect of illumination non-uniformity is reduced by performing a field flattening process with a Gaussian image smoothing algorithm. At step 606, the same Gaussian image convolution is performed on a more local region to extract local roughness by background average signal subtraction and thresholding. This initial roughness map is further categorized by categorizing/binning the rough feature sizes and shapes at step 608 and then performing a size and shape discrimination process (e.g., by thresholding) to reduce or remove unwanted noise, which results in a rough feature map, indicated at 612. The rough feature map can then be used to compute a skin smoothness index for the entire region, as indicated at 614.

Figures 25A, 25B:
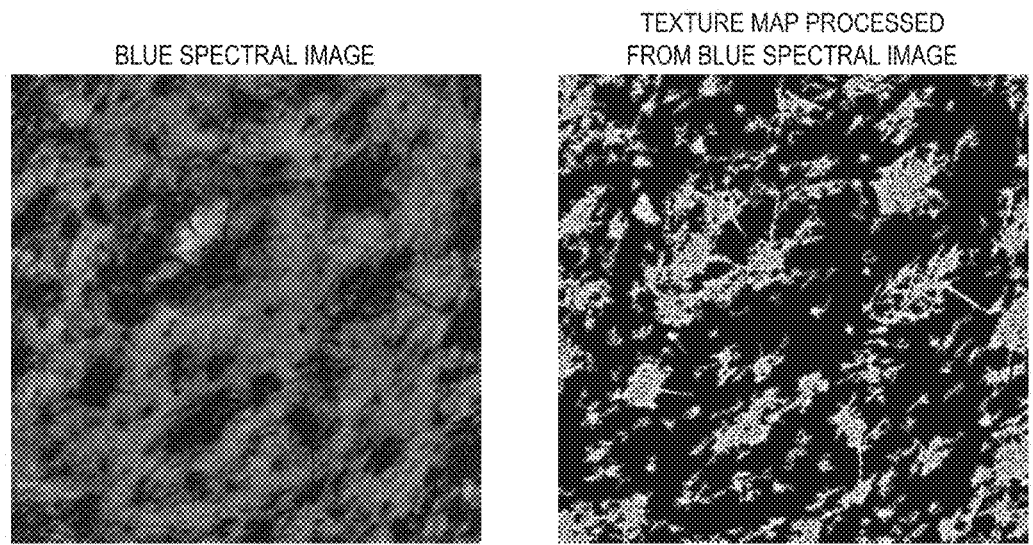
FIGS. 25A and 25B illustrate a blue spectral image for an example skin area and a texture map generated from the blue spectral image according to the algorithm shown in FIG. 24, according to an example embodiment.

FIGS. 25A and 25B illustrate a blue spectral image extracted from an image of an example skin area (e.g., captured by CMOS imaging device 500 or other type of imaging sensor 218) and a texture map generated from the blue spectral image according to the algorithm 600 shown in FIG. 24, according to an example embodiment. The texture contrast is significantly enhanced in the blue spectral image, as compared with the original captured image (e.g., illuminated by a white LED). As shown in FIG. 25B, the texture map processed from the blue spectral image clearly shows the major roughness features. This texture map may then be used to calculate a final skin smoothness index, as discussed above.

Figure 26:
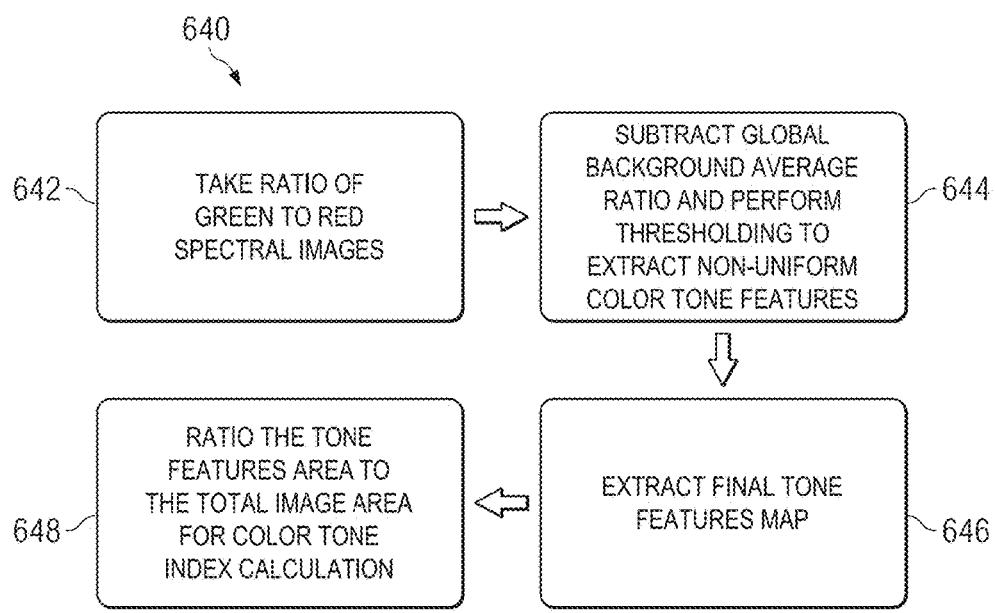
FIG. 26 is a process flow of a spectral analysis algorithm for analyzing skin color/tone, according to an example embodiment.

FIG. 26 is a process flow of a spectral analysis algorithm 640 for analyzing skin color/tone based on an image of the skin, e.g., captured by CMOS imaging device 500 or other type of imaging sensor 218, according to an example embodiment, according to an example embodiment. It has been determined that the best skin tone signal contrast is obtained from the ratio of green to red spectral signals. Thus, the algorithm 640 begins at step 642 by extracting green and red spectral images from the captured image, and calculating a map of the green to red image ratio. At step 644, non-uniform color tone features are extracted from the green/red ratio map by performing a background average signal subtraction and thresholding, which results in a final tone features map, indicated at 646. A skin color tone index can then be calculated from the final tone features map, e.g., by determining an area of the tone features (from the final tone features map) and calculating a ratio of the tone features area to the total image area.

Figure 27A:
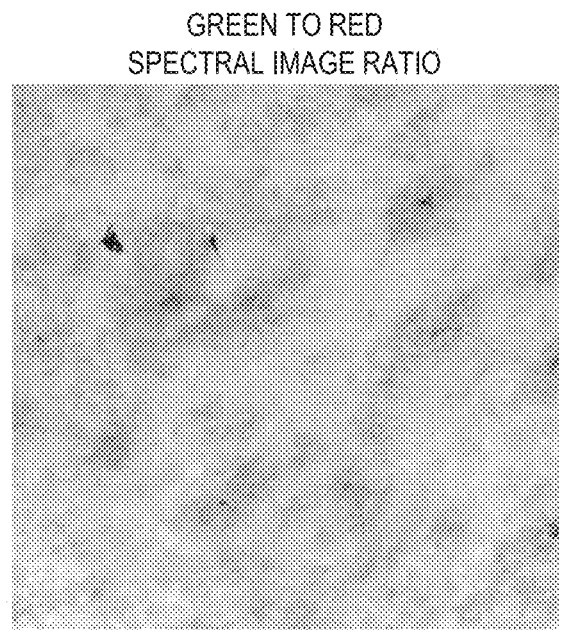
FIGS. 27A and 27B illustrate a green-to-red spectral image ratio for an example skin area and a tone feature map generated from the green-to-red spectral image ratio according to the algorithm shown in FIG. 26, according to an example embodiment.
Figure 27B:
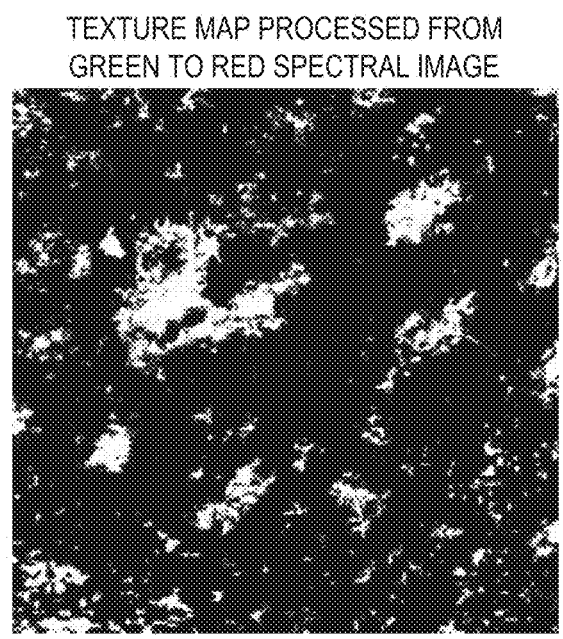

FIGS. 27A and 27B illustrate a green-to-red spectral image ratio extracted from an image of an example skin area (e.g., captured by CMOS imaging device 500 or other type of imaging sensor 218) and a tone feature map generated from the green-to-red spectral image ratio according to algorithm 640 shown in FIG. 26, according to an example embodiment. The contrast of all tone non-uniform regions is significantly enhanced in the green-to-red spectral image ratio, as compared with the original captured image (e.g., illuminated by a white LED). The same spectral ratio technique can be used to enhance contrast and perform global skin background subtraction for automatic hair counting to evaluate the hair removal device efficacy.

The spectral optical sensors and the skin image/signal processing algorithms discussed above may address the problem of providing multiple skin quality parameters feedback in a compact form that can be integrated with any dermatological treatment device 10. This may be especially useful for home use devices when coupled with treatment usage and routine advice using the sensors feedback data for trending analysis, e.g., via the internet-connected system of FIG. 1, for example.

Figure 28A:
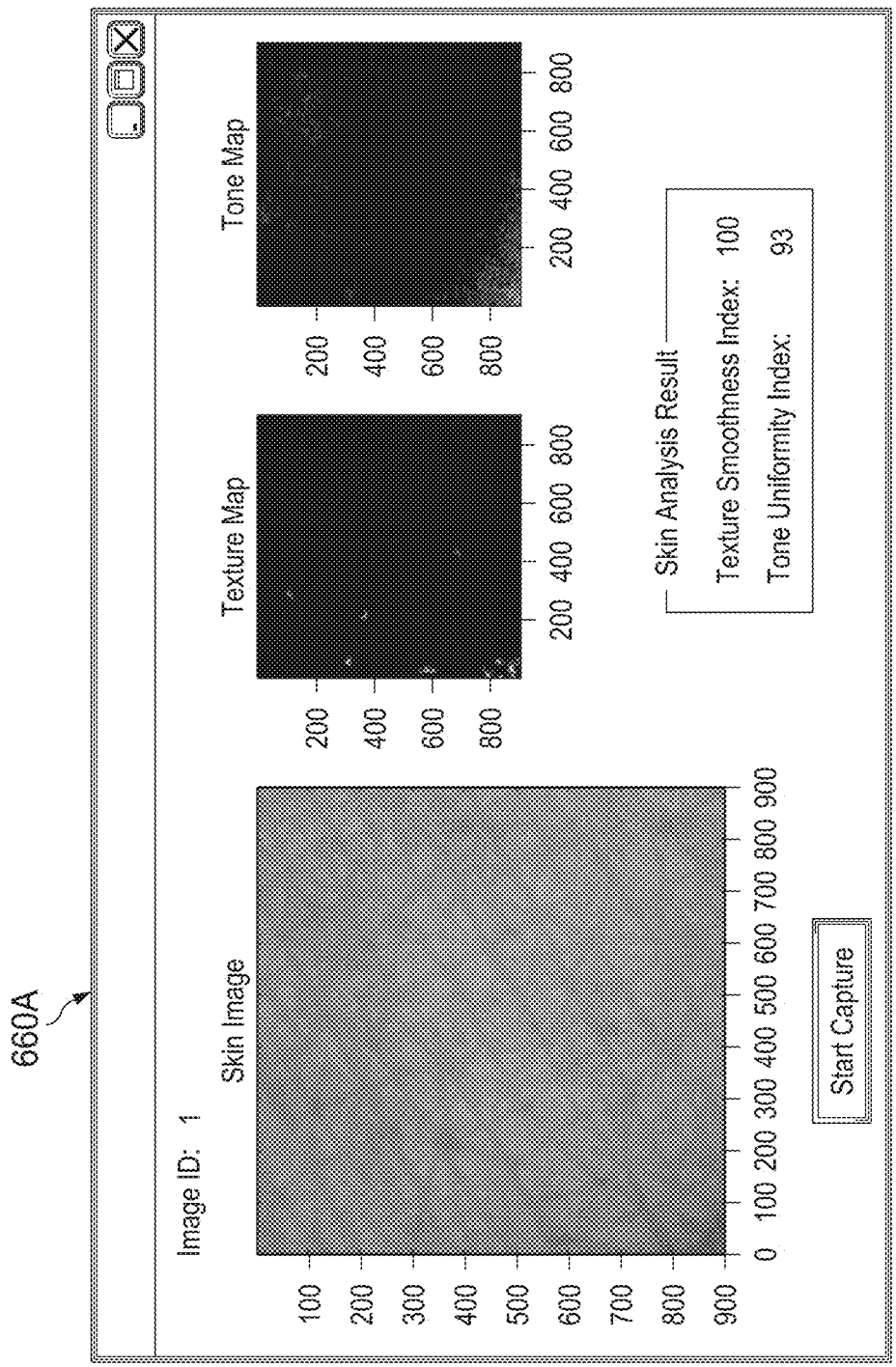
FIGS. 28A and 28B illustrate a texture map and tone feature map generated according to the algorithms shown in FIGS. 23 and 25, for a highly smooth and uniform tone skin area (FIG. 28A) and a less smooth and less uniform tone skin area (FIG. 28B), according to an example embodiment.
Figure 28B:
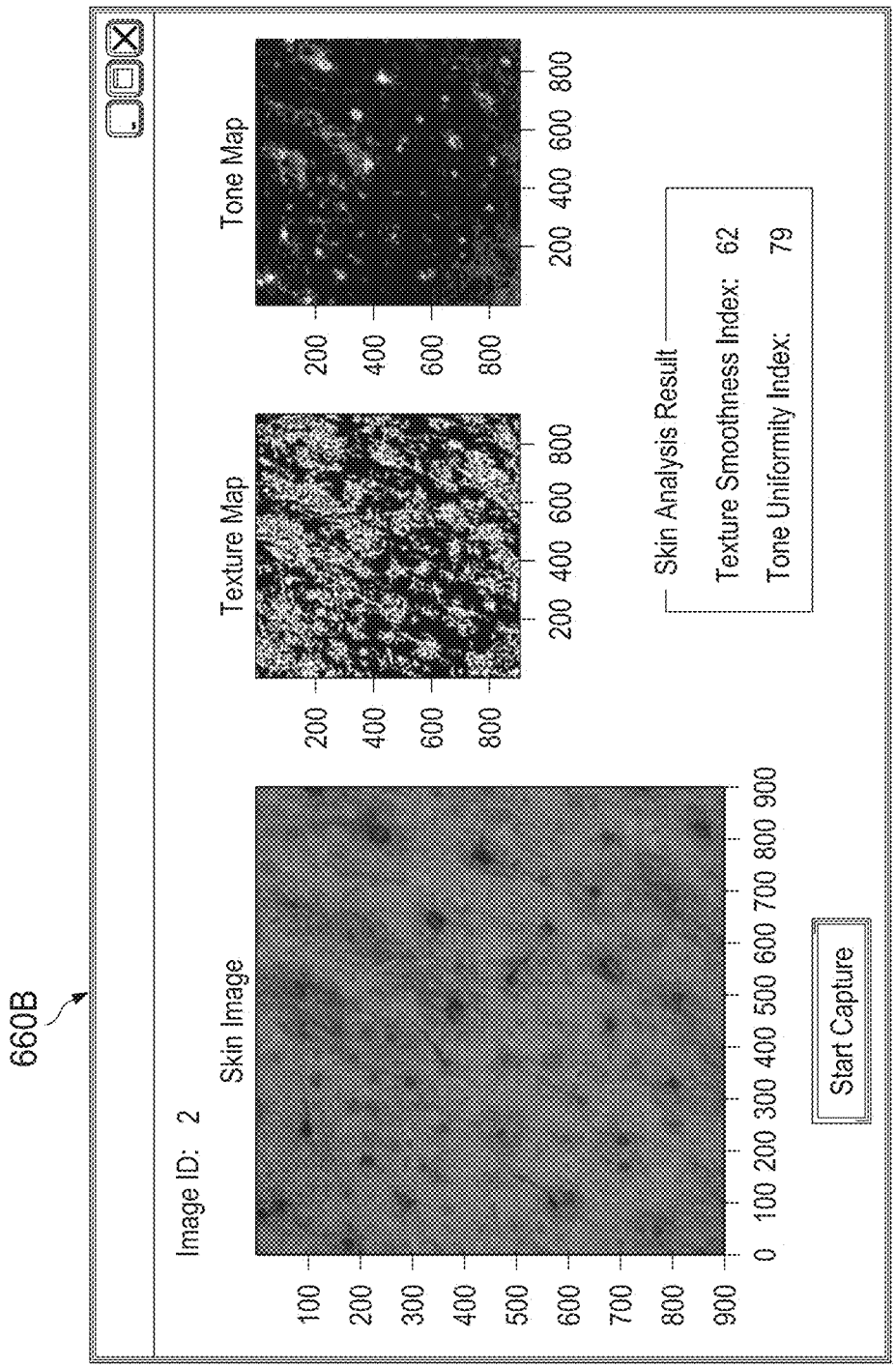

FIGS. 28A and 28B illustrate user feedback displays 660A and 660B including texture maps and tone feature maps generated from captured skin images (by CMOS imaging device 500 or other type of imaging sensor 218) according to algorithms 600 and 640 shown in FIGS. 24 and 26. In particular, FIG. 28A shows a texture map and tone feature map generated from a highly smooth and uniform color tone skin area, while FIG. 28B shows a texture map and tone feature map generated from a less smooth and less uniform color tone skin area. User feedback displays 660A and 660B also indicate a texture smoothness index and tone uniformity index, e.g., calculated according to algorithms 600 and 640. In some embodiments, user feedback displays 660A and 660B (including the underlying texture and tone feature map and respective indexes) may be calculated by remote analysis system 4 based on a image data received from device 10, and made available to a user as feedback via any suitable user device 5, e.g., via a browser or application hosted on such device 5.

MENDs Detection and Mapping

The wound healing process after a surgery or laser-based treatments is complicated and can leave behind evidence of recent tissue alteration such as scabs and scars. In laser-based fractional photothermolysis or "laser resurfacing", the epidermis and dermis are heated to a point where cellular breakdown and protein coagulation occur, killing cells in the epidermis and homogenizing collagen in the dermis. The damaged epidermis form microscopic epidermal necrotic debris (MENDs). If pigment is present, such as melanin, the MEND will adapt a dark brown color and appear as micro dot on the skin. Many MENDs in the same area will often appear to darken the skin. These MENDs eventually slough off with the natural skin renewal process. On the face, this can take a week before they are removed.

Based on a review of non-ablative fractional treated skin images captured by a custom skin texture meter using a blue light illuminated CMOS imager, the inventors observed the MENDs byproducts. Thus, the inventors developed systems and methods for identifying treatment areas and densities, e.g., from a fractional photothermolysis treatment (e.g., using a fractional treatment device 10 such as disclosed herein, within the context of or separate from an internet-connected analysis and feedback system), during the period before the resulting MENDs are naturally removed from the skin.

In some embodiments, a captured or live image is taken or a live visual inspection of a patient's treatment area is made. The resolution of the captured or live image should be sufficient enough to distinguish an individual MEND on the skin. This process can be aided by tools such as a camera for image processing or dermascope for live visual inspection. After an image is taken, the image is then processed to outline the treatment border and/or its relation to the treatment target. The mapped treatment area can then be compared to the live subject or an image of the subject to facilitate the treatment regimen. Analysis of the map can be used to determine where the treatment has occurred and whether the treatment area or treatment regimen needs to be adjusted to best optimize treatment results.

Figure 29A:
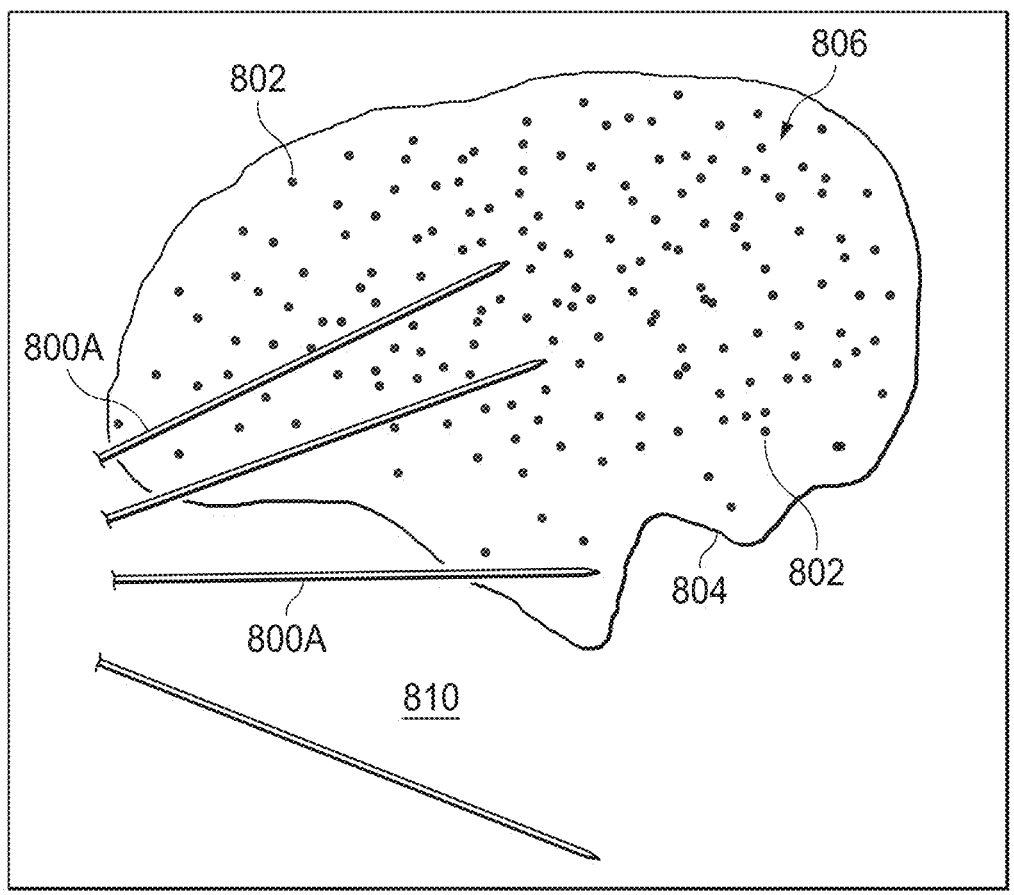
FIG. 29A illustrates an example pattern of microscopic epidermal necrotic debris (MENDs) resulting from a fractional treatment applied to target area of wrinkles.

FIG. 29A illustrates an example pattern of microscopic epidermal necrotic debris (MENDs) resulting from a fractional treatment applied to target area of wrinkles 800A. The dots 802 represent MENDs and are mapped to mark out the treated area, indicated by the border 804. An area 806 is identified where unnecessary treatment has occurred and another area 810 where no treatment has been made. Further treatments using device 10 can be controlled or adjusted, e.g., automatically controlled or adjusted by a control system of device 10, so that subsequent treatments are delivered to the intended target (wrinkles) 800A.

Figure 29B:
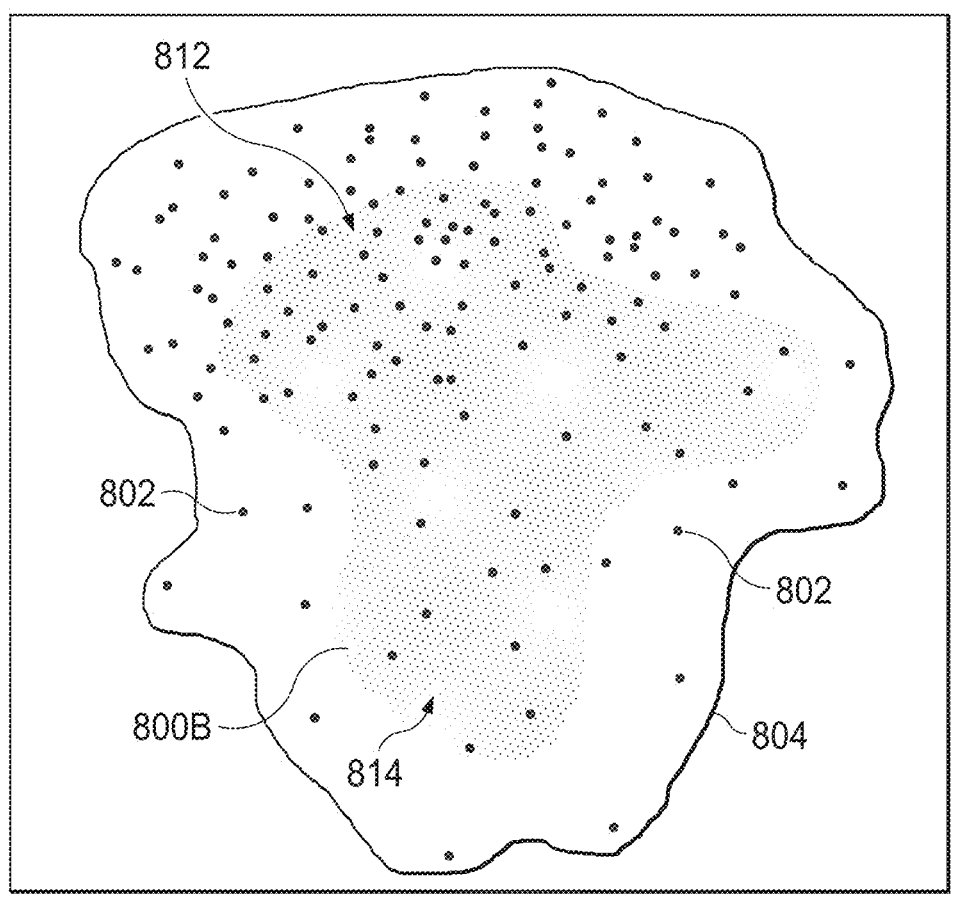
FIG. 29B illustrates an example pattern of MENDs resulting from a fractional treatment applied to target area of pigmentation.

FIG. 29B illustrates an example pattern of MENDs resulting from a fractional treatment applied to target area of pigmentation 800B. Again, dots 802 represent MENDs and are mapped to mark out the treated area, indicated by the border 804. An area 812 of high MENDs density and an area 814 of low MENDs density may be identified, e.g., by device 10. Further treatments using device 10 can be controlled or adjusted, e.g., automatically controlled or adjusted by a control system of device 10, so that subsequent treatments are delivered to the intended target area 800B with a uniform MENDs density.

The identification of MENDs can help the user focus on areas for treatment to potentially increase efficacy of the treatment, and can be used with any surgical or laser-based procedure that causes damage or change to tissue that can be detected visibly, spectroscopically, chemically, or any other form that can be detected or be enhanced for detection. Tissue alteration can be physical, thermal, chemical, or any other form that changes the characteristics of tissue. These concepts can be incorporated into a medical imaging system (such as the Canfield VISIA CR system) for doctors or software for computer or smart device as an app for consumers. The software is designed to process images captured from the image capturing system and give recommendation for treatment adjustments, or the user can evaluate the images for determining treatment adjustments.

The functionality disclosed above can also be incorporated into a laser treatment device 10, e.g., a battery-powered handheld fractional treatment device, which may include control electronics 30 to automatically map and analyze treated areas, e.g., by identifying and determining the number or density of MENDs in different areas, and automatically control operational aspects of the device 10, such as enabling/disabling the laser 14, or controlling an intensity, pulse duration, or other parameter of delivered laser radiation, based on the MENDs analysis (e.g., already treated vs. non-treated, local MENDs density) of the underlying skin, e.g., to prevent over-treatment and enhance treatment uniformity.

Over-treatment is a significant concern in fractional laser skin treatment, especially for a home use device where there is no professional supervision. It is also believed that some resting period is also beneficial to skin recovery and regrowth from the fractional treatment. Currently most devices accomplish the prevention of over-treatment by treatment time lock-out. A more desirable control may be to detect the actual skin treatment results and adjust the treatment density accordingly. It is well known that MENDs are the natural byproducts of a fractional laser skin treatment. The skin ejects excess melanin pigment through each microscopic laser treated spot. They are on the order of 50-300 µm size and appear dark. These natural labels usually appear 1-2 days after treatment, which is ideal for the normal recommended home use treatment frequency. A simple blue light CMOS imager with some magnification and automatic MENDs pattern extraction can provide local treatment density feedback and enable the device to adjust its real-time laser treatment density. This same MENDs density information can also be used to provide user feedback for treatment efficacy and progress.

Figure 30:
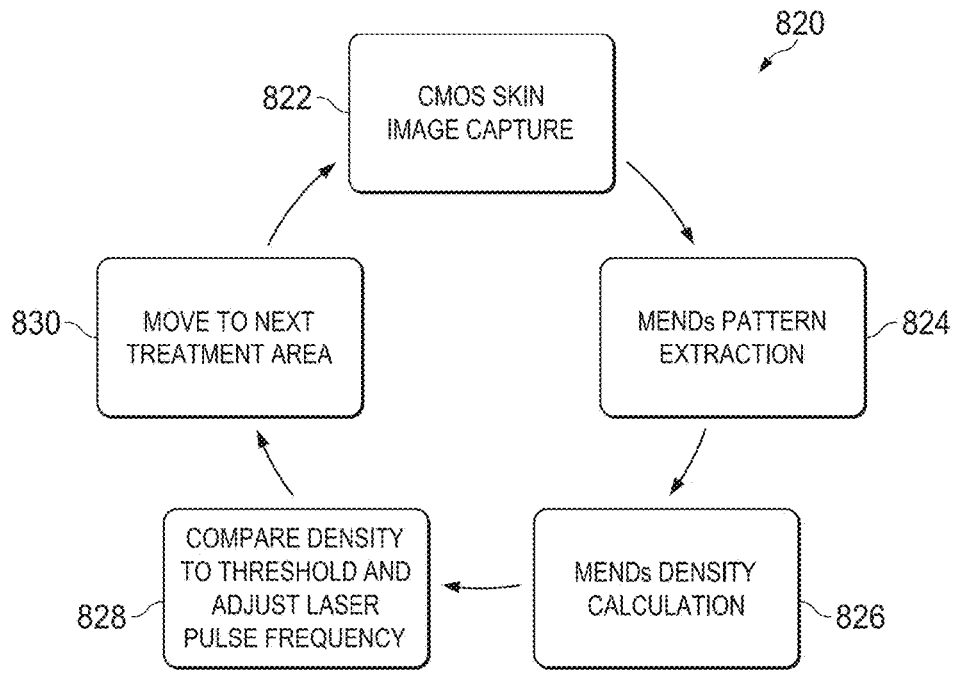
FIG. 30 a process flow for automatically controlling a dermatological treatment based on detection of MENDs in the skin, according to an example embodiment.

FIG. 30 shows an example feedback control loop 820 for automatically controlling a laser-based fractional treatment based on detection of MENDs in the skin, according to an example embodiment. The feedback control loop 820 (except for step 830, which may involve manual movement of the device by the user) may be executed automatically in real-time by control electronics 30 and a control system 52 of device 10.

Turning to feedback control loop 820, the skin image capture in the first step 822 of the control loop can be accomplished, for example, by a 2D CMOS image array with a simple 5-10× magnification optics. The image array may be illuminated by a blue light source such as one or more ~470-nm blue-light LEDs. Blue light enhances the skin surface contrast, as compared to longer wavelength visible or IR source. At step 824, device 10 converts the captured image to a gray scale intensity 2D image to extract the pattern of MENDs in the skin. At step 826, device 10 calculates the local MENDs density from the extracted pattern. At step 828, device 10 compares the calculated MENDs density to a predefined threshold and automatically controls one or more operational aspects of the device 10, such as enabling/disabling the laser 14, or controlling an intensity, pulse duration, or other parameter of delivered laser radiation, based on the calculated MENDs density/densities for the treatment area of skin being treated/about to be treated. For example, the laser pulsing frequency is determined and adjusted based on the determined local MENDs density, wherein an increased MENDs density results in a downward adjustment of the laser pulsing frequency, and vice versa. Thus the treatment density becomes more uniform and always controlled to be less than the over-treatment threshold. At step 830 the device 10 is moved to a new treatment area and the feedback loop continues.

Figure 31:
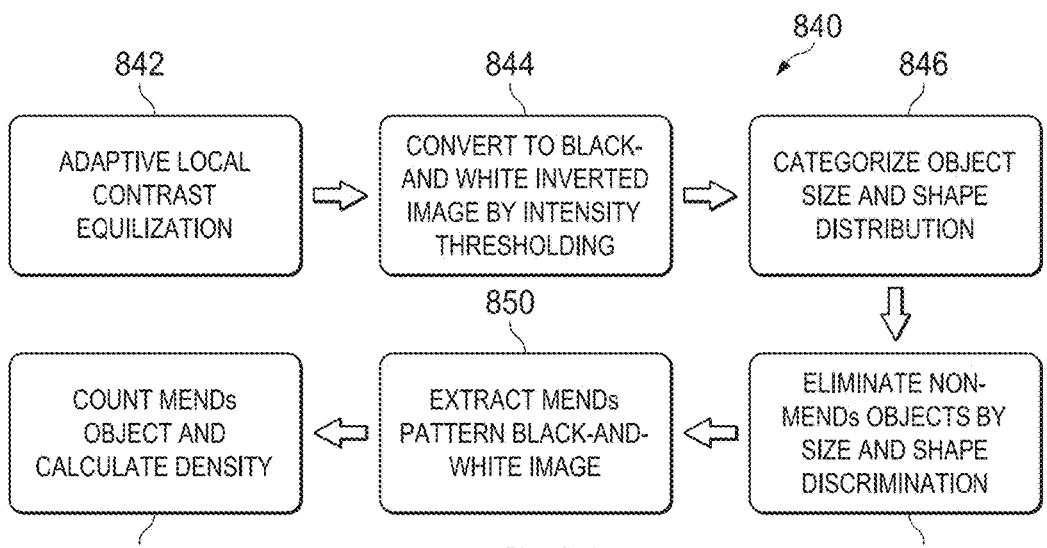
FIG. 31 a process flow of an algorithm for extracting a MENDs pattern and density in a region of skin, according to an example embodiment.

FIG. 31 a process flow of an algorithm 840 for MENDs pattern recognition algorithm and density extraction in a region of skin, e.g., for steps 824 and 826 of algorithm 820 discussed above, according to an example embodiment. Before the MENDs pattern extraction, at step 842 the 2D gray scale image is first contrast adjusted locally to make the entire intensity contrast profile more uniform. This is followed by applying a simple intensity thresholding and inversion to extract the dark objects from the gray scale image, at step 844. Some of these dark objects are due to other natural pigmentation or large skin texture changes. Their sizes and shape tend to be significantly different than the laser treatment induced MENDs. Therefore, the next step in the image analysis is to categorize the sizes and shapes of these objects at step 846 and selectively filter out those that are not within the expected range of MENDs at step 848. The result of the filtering process is the extracted MENDs pattern in a black-and-white image, indicated at 850, which can then be used by device 10 to count and estimate the MENDs density at step 852. Algorithm 840 may be executed automatically in real-time by control electronics 30 and a control system 52 of device 10.

In one example embodiment, a fractional treatment device 10 includes a MENDs analysis and control system 52 that including a CMOS imager 26 with magnifying optics and illumination source, a main controller/processor 144 for image analysis and laser feedback control, and a fractional laser treatment subsystem, all integrated in a self-contained handheld device 10.

The CMOS imager is preferably illuminated by a blue LED source for enhanced surface contrast. The optical system resolution should be sufficient to image a 50 µm sized MEND. Ideally each MEND should image to be at least 3-pixel wide. The main controller/processor should be able to capture and process each 1 $cm^2$ image frame within 0.25 s. and make laser control decision. This will allow normal device gliding speed up to 4 cm/s.

The fractional laser treatment subsystem is also controlled by the main controller/processor 144, which may be configured to modulate the laser pulsing frequency and thus the treatment density (i.e., density of treatments spots 70 generated on the skin) For a home use device, this fractional laser spot density normally ranges from 30 to 150 MTZs/$cm^2$.

Such system may be used to control a fractional laser dermatological device treatment density depending on the post treatment natural MENDs density. It can also be used to assess and provide user feedback for treatment efficacy and progress, as MENDs are usually the required result for an effective fractional laser treatment.

Some novel aspects of this system include the following. First, the system uses natural post treatment indicators for preventing subsequent over-treatment. Second, the system is capable of providing treatment efficacy and progress feedback for home users. Third, the system includes a fast image analysis algorithm for extracting MENDs pattern and density.

Some advantages of the invention include providing a compact, inexpensive, manufacturable device that uses readily available parts. The CMOS imager is commercially available in many consumer electronics. Both the over-treatment prevention and the efficacy and progress feedback may be particularly beneficial for home device users without professional supervision.

Testing Results

The inventors completed the initial work of prototyping a compact CMOS skin imager and tested the MENDs pattern extraction algorithm 840 described above.

Figure 32A:
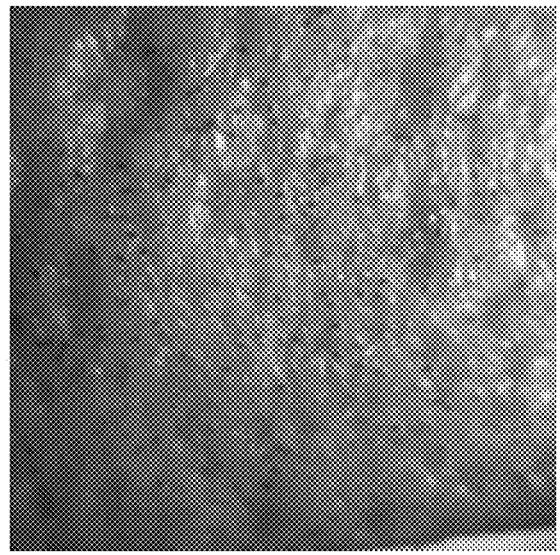
FIGS. 32A and 32B illustrate an image of a skin region treated by a fractional treatment device, and a corresponding pattern of MENDs automatically extracted using the algorithm of FIG. 31, according to an example embodiment.
Figure 32B:
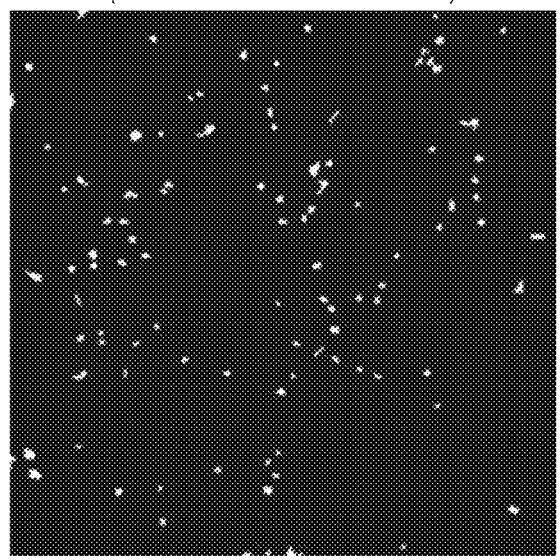

FIG. 32A is an image of a skin region treated by a fractional treatment device, with the image taken one day post treatment. The individual the MENDs, corresponding to treatment spots 70, can be seen scattered throughout the same skin area. FIG. 32B shows a corresponding pattern of MENDs automatically extracted from the image of FIG. 32A using algorithm 840 of FIG. 31, according to an example embodiment. The MENDs can then be counted from the extracted pattern to calculate the density.

Thus, some embodiments provide a method including imaging an area of skin using an imaging system; analyzing the imaged area of skin to identify detectable imprints or markings caused by a surgical procedure; mapping a treated area based on the identified imprints or markings; and adjusting a treatment or treatment regimen based on the mapped treated area. In a further embodiment, the detectable imprints or markings caused by a surgical procedure comprise MENDs caused by a fractional laser treatment. In a further embodiment, adjusting a treatment or treatment regimen based on the mapped treated area comprises automatically adjusting one or more operational aspects of a laser treatment device based on the mapped treated area. In a further embodiment, mapping a treated area comprises highlighting or outlining the treated area.

Another embodiment provides a device comprising a laser; an imaging system configured to image an area of skin; and a control system comprising logic instructions embodied in memory and executable by a processor to analyze the imaged area of skin to identify detectable imprints or markings caused by a surgical procedure, map a treated area based on the identified imprints or markings, and automatically adjust a treatment or treatment regimen based on the mapped treated area. In a further embodiment, automatically adjusting a treatment or treatment regimen based on the mapped treated area comprises automatically adjusting one or more operational aspects of the laser treatment based on the mapped treated area. In a further embodiment, the device is a battery-powered, handheld fractional treatment device.

Fractional Treatment Using Non-Water Chromophores in the Skin

Conventional water absorption based fractional laser treatment uses water as the main chromophore for generating micro thermal zones in skin. Each micro thermal zone (MTZ) on the order of several hundred microns in width and depth stimulates skin's natural cellular repair response to eject excess pigment and grow new collagen. Due to the small fraction (typically on the order of 1% for home used device and up to 30% for professional device) of laser treated skin, the key benefit of the fractional laser treatment is lower side effect and faster recovery.

Water makes up 50-70% of skin tissue and is universal for all skin type, it is most obvious to use water as the chromophore for laser absorption in general skin treatment. However, InP based water absorbing laser is relatively still high cost and deficient in power conversion efficiency. For a broader home used device market, it is desirable to have an alternative laser source that is less expensive and more efficient. GaAs based melanin absorbing laser is such a candidate.

The goal of a fractional treatment is to create multitude of micro thermal zones on skin. MTZs can be created by any type of laser tissue interaction that results in energy absorption and the heating of the treated area. The chart below shows the absorption characteristics of different key skin tissue components as a function of the laser wavelength. The water absorption peak near 1400-nm typically used in an InP based fractional laser treatment has an absorption coefficient of about 10 cm-1. The melanin absorption coefficient is on the order of 100's cm-1 near 800-nm. Although the melanin concentration in skin tissue is significantly lower than water and is dependent on the natural skin type, it is possible to achieve the same MTZs with GaAs based laser near 800-nm, especially on regions with excess pigment due to sun damage or aging.

Figure 33:
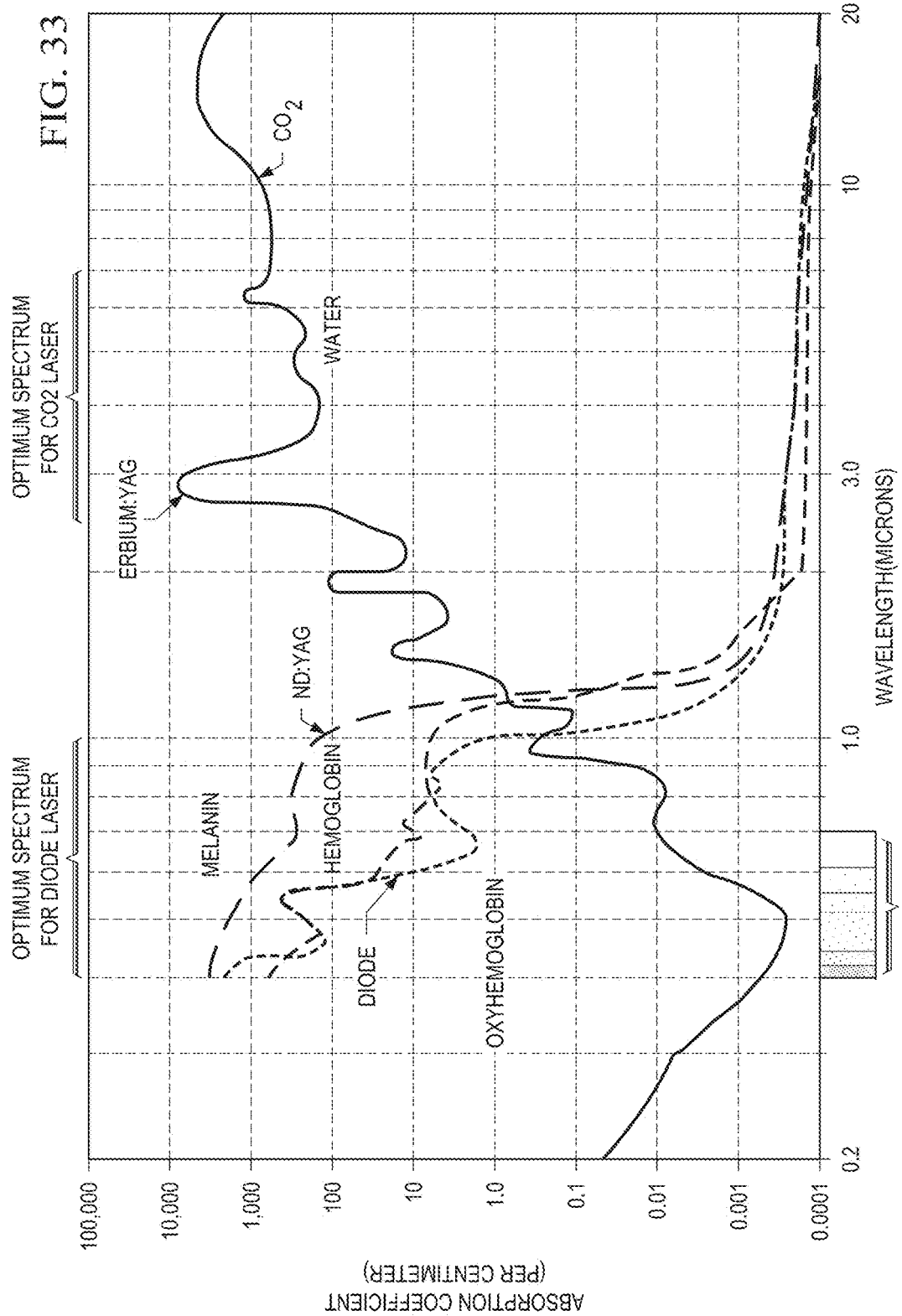
FIG. 33 illustrates the absorption characteristics of various chromophores at various wavelengths.

FIG. 33 illustrates the absorption characteristics of various chromophores at various wavelengths. Known professional non-ablative fractional laser treatment devices use wavelength in the range of 1300 to 2000 nm, all based on water absorption. Various home use fractional devices are also based on 14xx-nm InP water-absorbing laser.

In contrast, present embodiments involve using a non-water absorbing chromophore for fractional laser skin treatment. For example, an 808-nm melanin absorbing multi-emitters laser bar can be used for age spot and pigmented lesion fractional treatment. The structure used in the first prototype is a direct exposure of the laser bar emitters without any intervening shaped optics. Only a protective flat window was used. See figure below for the direct exposure structure concept sketch.

FIG. 34 illustrates an example laser package 900 including a GaAs laser diode bar 902 for use in a portable dermatological treatment device 10, according to one embodiment. As shown, the GaAs laser diode bar 902 may be mounted to a CuW submount 904, which is mounted to a heatsink 906, which provides the laser cathode contact, via a metallized BeO ceramic layer 908, which provides the laser anode contact. A sapphire window 910 may be arranged over the laser bar 902, e.g., spaced from the laser bar 902 by a Kapton spacer 912, which may define an air or vacuum filled region 914 between the laser bar 902 and window 910.

The laser bar 902 is a GaAs based multi-emitter semiconductor laser with near-IR wavelength output typically in the range of 790 to 920 nm. The laser bar length is typically 5 to 10 mm. Bar thickness is typically 100 to 200 μm. Bar height or laser cavity length is typically 1.0 to 1.5 mm. Each 10-mm long bar usually can accommodate 15 to 60 emitters, with each emitter sized about 50 to 150 μm in the slow axis direction and about 5 μm in the fast axis direction.

FIG. 35 illustrates an example pattern of treatment spots 70 formed on the skin by a single pulse of a GaAs laser bar 902 at 808-nm, with the laser in close proximity to the skin, according to an example embodiment. Each micro-emitter of the laser bar 902 forms a discrete spaced-apart MTZ/treatment spot 70 on the skin, due to the very close proximity of the laser bar 902 to the skin, e.g., less than 10 mm, less than 5 mm, less than 2 mm, or less than 1 mm. The MENDs (Microscopic Epidermal Necrotic Debris) generated by each fractional treatment spot 70 is also very similar to the conventional water absorbing fractional laser treatment.

There are several key distinguishing features from conventional systems. One is the non-water absorbing wavelength. Another is the direct contact exposure from a multi-emitter laser bar. In this particular implementation, an 808-nm melanin absorbing 19-emitter GaAs laser bar was used to generate the fractional laser treatment spots. Each fractional treatment spot size is less than 200 μm wide, similar to a conventional water-absorbing fractional treatment. However, 19 concurrent fractional treatment spots are applied to the treatment area in a single pulse without any optical scanning element, or in some embodiment, without any optics at all (wherein the planar window 910 is not an optic). It is also possible to apply the same technique for radiation absorption by hemoglobin in the wavelength range of 400 and 650 nm, e.g., about 580 nm, or radiation absorption by fat in the appropriate wavelength range.

This concept can be used to target treatment of pigment lesions or related skin aging issues such as age spots, for example. The fractional laser treatment technique enables faster recovery and less undesirable side effect. Once possible advantages is that the cost of GaAs based non-water absorbing laser is significantly lower than water absorbing InP base laser. For example, the cost of an 808-nm GaAs laser is currently about $0.20/W, whereas a 1450-nm InP laser is currently about $6/W, a factor of 30× difference. GaAs based laser is also much more widely available and produced in greater volume.

Further, the power efficiency performance of GaAs based non-water absorbing laser is significantly better than InP based water absorbing laser. For example, an 808-nm or 915-nm GaAs laser has a typical power conversion efficiency in excess of 50%, whereas the InP water absorbing laser has an efficiency typically less than 30%, close to a factor of 2× difference. This is especially important for battery power home used devices.

Still further, for skin pigment related treatment, melanin absorption targeted fractional treatment is significantly less painful than broadly absorbing water based fractional treatment. For example, the relatively small water absorption of an 808-nm GaAs laser will have little effect on non-pigmented light skin area.

One application is in home-use battery powered fractional laser treatment device for pigment related skin problems, such as pigmented lesions, benign nevi, and age spots. For darker skin type (e.g., Fitzpatrick Type III to VI), the laser can also be integrated with smart pigment sensor to control the appropriate laser power and energy dose for general skin aging treatment for fine lines, wrinkles, and skin texture roughness.

Various embodiments may use laser radiation of various wavelengths that are absorbed by different types of chromophores. For example, some example embodiments are listed below in Table 1.

TABLE 1

| Absorbing chromophores for different laser radiation wavelengths | | | | |
|---|---|---|---|---|
| Laser type | Wavelength range | Example wavelengths | Energy delivered to skin surface, per microemitter/ microbeam | Absorbing Chromophore(s) |
| GaAs single-emitter diode laser | 790-920 nm | 808 or 915 nm | 100-500 mJ | melanin |
| GaAs multi-emitter laser bar | 790-920 nm | 808 or 915 nm | 20-300 mJ | melanin |
| Ytterbium fiber laser | 480-670 nm | 580 nm | 5-50 mJ | hemoglobin |
| GaN laser diode | 360-480 nm | 445 nm | 5-50 mJ | melanin and hemoglobin |

The concepts disclosed above may be incorporated in any suitable dermatological treatment device for providing a fractional laser treatment for any suitable dermatological treatment, e.g., skin rejuvenation, wrinkle treatment, treatment of vascular lesions (e.g., spider veins, diffuse redness, etc.), treatment of cellulite, treatment of pigmented legions (e.g., age spots, sun spots, moles, etc.), tattoo removal, and various other treatments.

What is claimed is:

1. A dermatological treatment and analysis system, comprising:
   a handheld treatment device, comprising:
      a handheld body;
      a treatment radiation source housed in the handheld body;
      electronics configured to control the treatment radiation source to deliver radiation to the skin to provide a dermatological treatment that forms microscopic epidermal necrotic debris (MENDs) in the skin;
      at least one skin sensor housed or integrated in the handheld body and configured to generate signals indicative of one or more properties of the skin; and
      a processor configured to:
         analyze the signals from the at least one skin sensor to identify a plurality of discrete MENDs formed by the radiation delivered to the skin by the handheld treatment device;
         calculate a quantity or density of identified MENDs in at least one area of the skin; and
         generate skin-related data based at least on the calculated quantity or density of identified MENDs;
      a wireless transmitter integrated in the handheld treatment device, wherein the wireless transmitter is configured to wirelessly transmit the skin-related data for remote analysis or display of the skin-related data;

such that the handheld treatment device is configured to both (a) deliver radiation to the skin to provide the dermatological treatment and (b) wirelessly transmit skin-related data, detected by the at least one sensor of the handheld treatment device, for remote analysis or display of the skin-related data.

2. The dermatological treatment and analysis system of claim 1, further comprising a remote data analysis system configured to:

receive the skin-related data transmitted by the wireless transmitter via a communications network;

analyze the received skin-related data to generate skin analysis data; and communicate the skin analysis data to a user via a display device or via the communications network.

3. The dermatological treatment and analysis system of claim 2, wherein the remote data analysis system is configured to:

identify previously received skin-related data associated with the same treatment device or user as the currently received skin-related data;

analyze the currently received skin-related data and previously received skin-related data to generate skin-related trend data associated with the treatment device or user, the skin-related trend data indicating trends in one or more skin-related parameter over time; and communicate the skin-related trend data to the user via the communications network.

4. The dermatological treatment and analysis system of claim 2, wherein the remote data analysis system is configured to:

identify previously received device usage data associated with the same treatment device or user as the currently received device usage data;

analyze the currently received device usage data and previously received device usage data to generate device usage trend data associated with the treatment device or user, the device usage trend data indicating trends in the usage of the treatment device over time; and communicate the device usage trend data to the user via the communications network.

5. The dermatological treatment and analysis system of claim 2, wherein:

the handheld treatment device further includes electronics configured to generate device usage data related to the usage of the handheld treatment device by a user;

the wireless transmitter is further configured to wirelessly transmit the device usage data to the communications network; and the remote data analysis system is configured to:

receive the device usage data transmitted by the wireless transmitter via the communications network;

analyze the received device usage data to generate device usage analysis data; and communicate the device usage analysis data to the user via the communications network.

6. The dermatological treatment and analysis system of claim 2, further comprising a user device comprising a display and configured to:

receive the skin analysis data transmitted by the remote data analysis system via the communications network; and display the skin analysis data to a user via the display.

7. The dermatological treatment and analysis system of claim 6, wherein the handheld treatment device, remote data analysis system, and user device are configured to cooperate such that the skin analysis data is displayable via the user device in real time or substantially in real time (a) during a treatment session using the handheld treatment device, or (b) upon the completion of a treatment session using the handheld treatment device.

8. The dermatological treatment and analysis system of claim 6, wherein the handheld treatment device, remote data analysis system, and user device are configured to cooperate such that the skin analysis data is displayable via the user device in real time or substantially in real time upon a connection of the handheld treatment device with a docking device.

9. The dermatological treatment and analysis system of claim 6, wherein the handheld treatment device, remote data analysis system, and user device are configured to cooperate such that the device usage analysis data is displayable via the user device in real time or substantially in real time (a) during a treatment session using the handheld treatment device, (b) upon the completion of a treatment session using the handheld treatment device, or (c) upon the handheld treatment device being removably connected to a docking device.

10. A dermatological treatment and analysis system, comprising:

a handheld treatment device, comprising:

a handheld body;

a treatment radiation source housed in the handheld body;

electronics configured to control the treatment radiation source to deliver radiation to the skin to provide a dermatological treatment that forms microscopic epidermal necrotic debris (MENDs) in the skin;

at least one skin sensor housed or integrated in the handheld body and configured to generate signals indicative of one or more properties of the skin; and a wireless transmitter configured to receive skin-related data comprising the signals from the at least one skin sensor and/or information derived from such signals, and to wirelessly transmit the received data to a communications network for remote analysis of the skin-related data;

such that the handheld treatment device is configured to both (a) deliver radiation to the skin to provide the dermatological treatment and (b) wirelessly transmit skin-related data, detected by the at least one sensor of the handheld treatment device, for remote analysis of the skin-related data; and a remote data analysis system including at least one processor configured to:

receive the skin-related data transmitted by the wireless transmitter via the communications network;

analyze the received skin-related data to identify a plurality of discrete MENDs formed by the radiation delivered to the skin by the handheld treatment device;

calculate a quantity or density of identified MENDs in at least one area of the skin;

generate skin-related data that is dependent on the calculated quantity or density of identified MENDs; and communicate the skin skin-related data to a user via a display device or via the communications network.

11. The dermatological treatment and analysis system of claim 10, further comprising a user device comprising a display and configured to:
  receive the skin analysis data transmitted by the remote data analysis system via the communications network; and
  display the skin analysis data to a user via the display.

12. The dermatological treatment and analysis system of claim 10, wherein the wireless transmitter is integrated in the handheld treatment device.

13. A dermatological treatment and analysis system, comprising:
  a handheld treatment device, comprising:
    a handheld body;
    a treatment radiation source housed in the handheld body;
    electronics configured to control the treatment radiation source to deliver radiation to the skin to provide a dermatological treatment that forms microscopic epidermal necrotic debris (MENDs) in the skin;
    at least one skin sensor housed or integrated in the handheld body and configured to generate signals indicative of one or more properties of the skin; and
  a processor configured to:
    receive the signals from the at least one skin sensor;
    analyze the signals from the at least one skin sensor to identify a plurality of discrete MENDs formed by the radiation delivered to the skin by the handheld treatment device;
    calculate a quantity or density of identified MENDs in at least one area of the skin;
    using the calculated quantity or density of identified MENDs to generate skin-related data; and
    display via a display device or wirelessly transmit the skin-related data for remote analysis or display of the skin-related data.

14. The dermatological treatment and analysis system of claim 13, wherein the processor is provided in the handheld treatment device.

15. The dermatological treatment and analysis system of claim 13, wherein the processor is provided in a device distinct from the handheld treatment device.

16. The dermatological treatment and analysis system of claim 1, wherein:
  the handheld treatment device is configured to provide a fractional treatment to the skin by delivering laser radiation to an array of spaced apart locations on the skin to thereby create an array of spaced-apart microthermal zones (MTZs) in the skin;
  wherein the array of MTZs form a corresponding array of MENDs in the skin.

17. A handheld treatment device, comprising:
  a handheld body;
  a treatment radiation source housed in the handheld body;
  electronics configured to control the treatment radiation source to deliver radiation to the skin to provide a fractional treatment by delivering laser radiation to an array of spaced apart locations on the skin to thereby create an array of spaced-apart microthermal zones (MTZs) in the skin;
  wherein the array of MTZs form a corresponding array of microscopic epidermal necrotic debris (MENDs) in the skin;
  at least one skin sensor housed or integrated in the handheld body and configured to generate sensor signals indicative of one or more properties of the skin; and
  a control system including at least one processor configured to:
    analyze the sensor signals to identify a plurality of discrete MENDs formed by the radiation delivered to the skin by the handheld treatment device;
    calculate a quantity or density of identified MENDs in at least one area of the skin; and
    control the treatment radiation source as a function of calculated quantity or density of identified MENDs.

* * * * *